(12) United States Patent
Seehra et al.

(10) Patent No.: US 12,331,124 B2
(45) Date of Patent: Jun. 17, 2025

(54) ALK2 ANTIBODIES AND METHODS OF USE THEREOF

(71) Applicant: Keros Therapeutics, Inc., Lexington, MA (US)

(72) Inventors: Jasbir S. Seehra, Lexington, MA (US); Jennifer Lachey, Lincoln, MA (US)

(73) Assignee: Keros Therapeutics, Inc., Lexington, MA (US)

( * ) Notice: Subject to any disclaimer, the term of this patent is extended or adjusted under 35 U.S.C. 154(b) by 1092 days.

(21) Appl. No.: 17/237,240

(22) Filed: Apr. 22, 2021

(65) Prior Publication Data

US 2021/0253720 A1 Aug. 19, 2021

Related U.S. Application Data

(63) Continuation of application No. PCT/US2019/057679, filed on Oct. 23, 2019.

(60) Provisional application No. 62/749,463, filed on Oct. 23, 2018.

(51) Int. Cl.
| | |
|---|---|
| *A61P 19/00* | (2006.01) |
| *A61P 7/06* | (2006.01) |
| *A61P 19/10* | (2006.01) |
| *C07K 16/28* | (2006.01) |
| *A61K 39/00* | (2006.01) |

(52) U.S. Cl.
CPC ............ *C07K 16/2863* (2013.01); *A61P 7/06* (2018.01); *A61P 19/00* (2018.01); *A61P 19/10* (2018.01); *A61K 2039/505* (2013.01); *C07K 2317/565* (2013.01); *C07K 2317/92* (2013.01)

(58) Field of Classification Search
CPC .................................................. C07K 16/2863
USPC ........................................................ 424/173.1
See application file for complete search history.

(56) References Cited

U.S. PATENT DOCUMENTS

| | | | |
|---|---|---|---|
| 8,338,377 | B2 | 12/2012 | Seehra |
| 10,260,068 | B2 | 4/2019 | Hino et al. |
| 10,428,148 | B2 | 10/2019 | Katagiri et al. |
| 2010/0062001 | A1 | 3/2010 | Reiter et al. |
| 2011/0182904 | A1 | 7/2011 | Zimmerman et al. |
| 2013/0089560 | A1 | 4/2013 | Chartier-Courtaud et al. |
| 2016/0075772 | A1 | 3/2016 | Hatsell et al. |
| 2018/0118835 | A1 | 5/2018 | Katagiri et al. |
| 2018/0180614 | A1 | 6/2018 | Crowe, Jr. et al. |
| 2021/0393605 | A1 | 12/2021 | Seguy et al. |
| 2023/0372390 | A1 | 11/2023 | Seehra et al. |
| 2023/0398118 | A1 | 12/2023 | Seehra et al. |
| 2023/0406956 | A1 | 12/2023 | Seehra et al. |

FOREIGN PATENT DOCUMENTS

| | | |
|---|---|---|
| EP | 3252074 A1 | 12/2017 |
| WO | WO-2012/065059 A2 | 5/2012 |
| WO | WO-2016/039796 A2 | 3/2016 |
| WO | WO-2020/118011 A1 | 6/2020 |
| WO | WO-2021/163170 A1 | 8/2021 |
| WO | WO-2022/240948 A1 | 11/2022 |

OTHER PUBLICATIONS

Rudikoff et al. (Proceedings of the National Academy of Sciences, 1982, 79:1979-1983).*
Casset et al. (Biochemical and Biophysical Research Communications, 2003, 307:198-205).*
Holm et al. (Molecular Immunology, 2007: 1075-1084).*
Asshoff et al., "Momelotinib inhibits ACVR1/ALK2, decreases hepcidin production, and ameliorates anemia of chronic disease in rodents," Blood. 129(13):1823-1830 (Mar. 2017).
Kaplan et al., "From mysteries to medicines: drug development for fibrodysplasia ossificans progressiva," Expert Opin Orphan Drugs. 1(8):637-649 (Aug. 2013).
Pang et al., "ACVR1-Fc suppresses BMP signaling and chondro-osseous differentiation in an in vitro model of Fibrodysplasia ossificans progressiva," Bone. 92:29-36 (Aug. 2, 2016).
Santa Cruz Biotechnology, Inc., Datasheet for "ACTR-I (C-5): sc-374523," <https://datasheets.scbt.com/sc-374523.pdf>, retrieved on May 25, 2018 (1 page).
Santa Cruz Biotechnology, Inc., Datasheet for "ACTR-Ia (Y0311): sc-73676," <https://datasheets.scbt.com/sc-73676.pdf>, retrieved on May 23, 2018 (1 page).
Aykul et al. "Anti-ACVR1 antibodies exacerbate heterotopic ossification in fibrodysplasia ossificans progressiva (FOP) by activating FOP-mutant ACVR1," J Clin Invest. 132(12): (14 pages) (Published Jun. 15, 2022).
Harth et al. "A Selection Fit Mechanism in BMP Receptor IA as a Possible Source for BMP Ligand-Receptor Promiscuity," PLoS One. 5(9): 1-13 (Published Sep. 28, 2010).
Katagiri et al., "Development of blocking monoclonal antibodies against ALK2, which is a type I receptor for BMPs," Annual Meeting of the American Society for Bone and Mineral Research, Colorado Convention Center, Denver, CO, USA—Sep. 8-11, 2017, Abstract 1094. 32(S1):S33 (2017).

(Continued)

*Primary Examiner* — Sean E Aeder
(74) *Attorney, Agent, or Firm* — Clark & Elbing LLP

(57) ABSTRACT

The invention features ALK2 antibodies and antigen binding fragments thereof (e.g., ALK2 binding fragments). The invention also features pharmaceutical compositions and methods of using the ALK2 antibodies or antigen binding fragments thereof to treat bone disease or damage, low red blood cell levels (e.g., anemia or blood loss), heterotopic ossification (e.g., heterotopic ossification resulting from fibrodysplasia ossificans progressiva), Sjogren's syndrome (e.g., dry eye associated with Sjogren's syndrome), multiple osteochondroma, diffuse intrinsic pontine glioma, posterior capsule opacification, or cardiac hypertrophy and/or cardiac fibrosis.

13 Claims, 16 Drawing Sheets

Specification includes a Sequence Listing.

(56) References Cited

OTHER PUBLICATIONS

Sun et al., "Mucus binding protein [Lactobacillus kitasatonis DSM 16761 = JCM 1039]," <www.ncbi.nlm.nih.gov/protein/KRM05866, retrieved Jan. 29, 2020 (2 pages).
Olsen et al., "BMPR2 inhibits activin- and BMP-signaling via wild yype ALK2," J Cell Sci 131(11):jcs213512 (2018) (39 pages).
International Search Report and Written Opinion for International Application No. PCT/US2019/057679, dated Feb. 20, 2020 (19 pages).
Fujimoto, Mai, et al. "Establishment of a novel model of chondrogenesis using murine embryonic stem cells carrying fibrodysplasia ossificans progressiva-associated mutant ALK2." Biochemical and biophysical research communications 455.3-4 (2014): 347-352.12.12.2014.

* cited by examiner

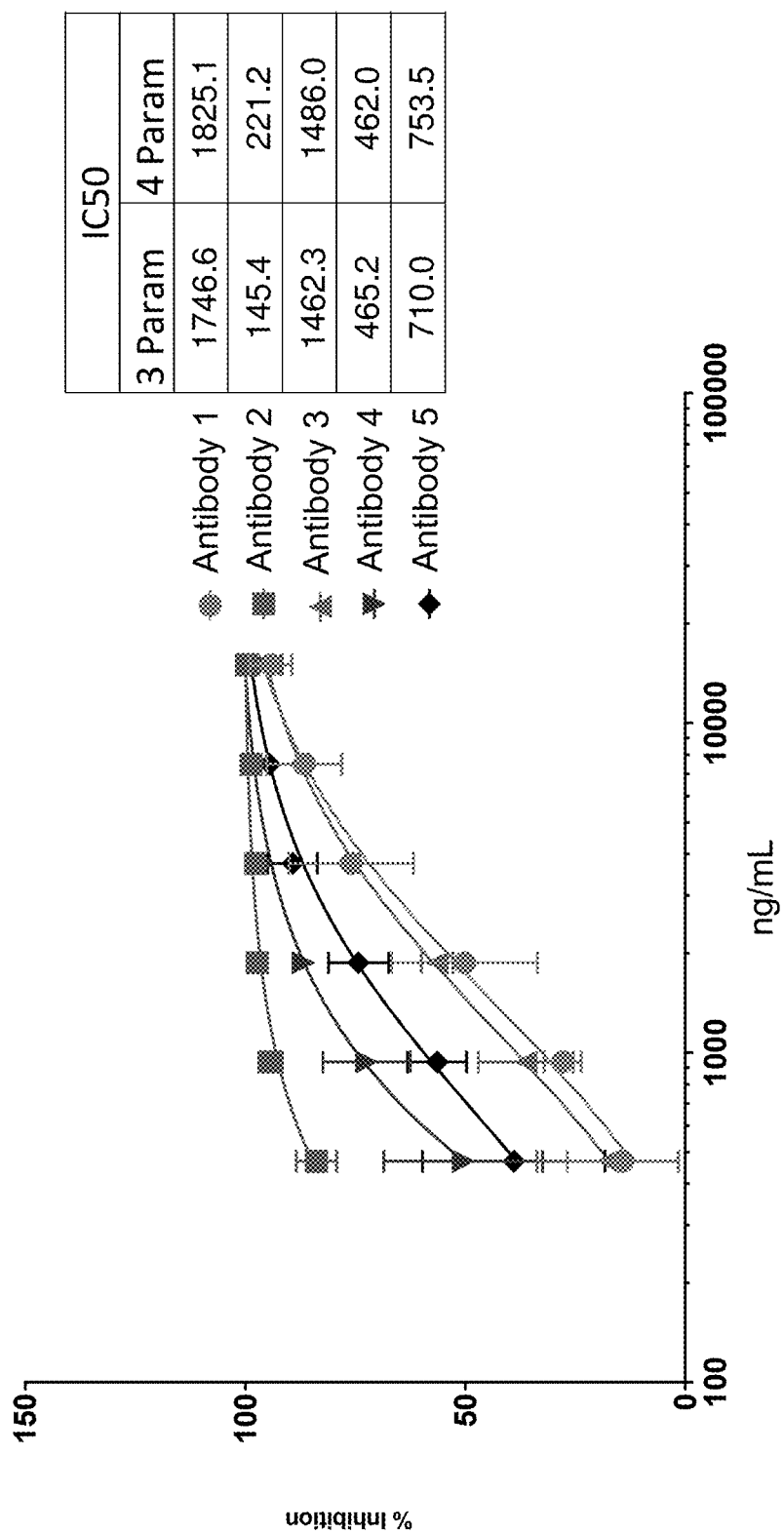

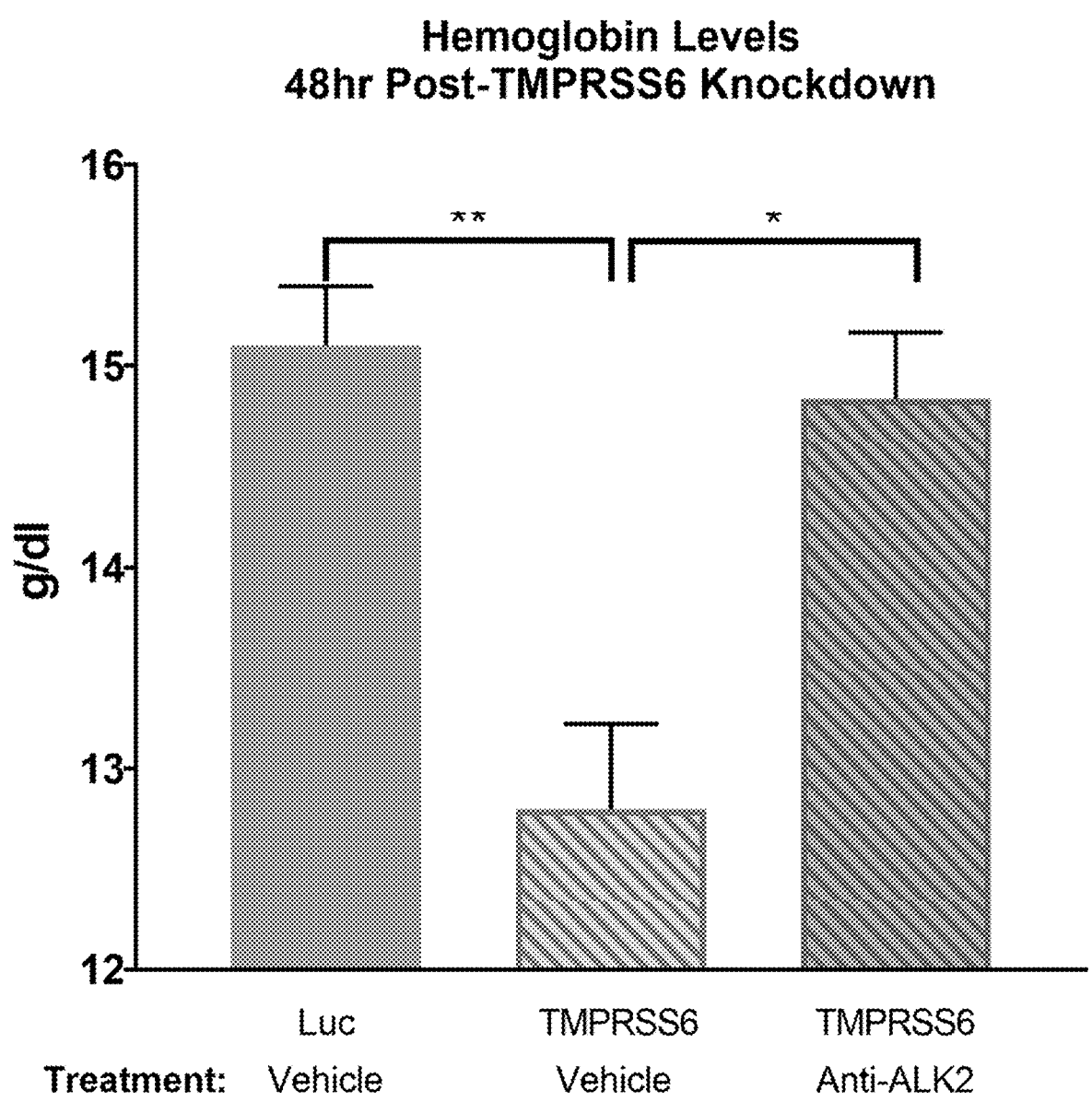

FIG. 5

```
FEATURES                                          Location/Qualifiers
        Region          1..112
                                                  /label=Vl1_5a
        Region          113..215
                        /label=CL lambda
                        /note="Human C lambda 1 domain, Genbank P01842"
        Region          217..332
                        /label=VH1A_4
        Region          333..434
                        /label=CH1
                        /note="Human IgG1 CH1 domain, Genbank A49444"
        Region          435..436
                        /label=EcoRI linker
                        /note=-
        Region          437..444
                        /label=M2Flag tag
                        /note=8 amino acid tag recognized by the M2 antibody
        Region          445..447
                        /label=Tag linker I
                        /note=-
        Region          448..453
                        /label=His6 tag
                        /note=6 amino acid Histidin tag
        Region          23..35
                        /label=VL CDR1
        Region          47..57
                        /label=VL CDR2
        Region          90..99
                        /label=VL CDR3
        Region          242..251
                        /label=VH CDR1
        Region          263..282
                        /label=VH CDR2
        Region          315..321
                        /label=VH CDR3
ORIGIN
       1 DIVLTQPPSV SGAPGQRVTI SC░░░░░░░ ░░░░░WYQQL PGTAPK░░░ ░░░░░░░GVP
      61 DRFSGSKSGT SASLAITGLQ AEDEADYYC░ ░░░░░░░░V FGGGTKLTVL GQPKAAPSVT
     121 LFPPSSEELQ ANKATLVCLI SDFYPGAVTV AWKADSSPVK AGVETTTPSK QSNNKYAASS
     181 YLSLTPEQWK SHRSYSCQVT HEGSTVEKTV APTEA*QVQL VQSGAEVKKP GSSVKVSCKA
     241 S░░░░░░░ ░WVRQAPGQG LE░░░░░░ ░░░░░░░░░ ░RVTITADE STSTAYMELS
     301 SLRSEDTAVY YCAR░░░░░ ░WGQGTLVTV SSASTKGPSV FPLAPSSKST SGGTAALGCL
     361 VKDYFPEPVT VSWNSGALTS GVHTFPAVLQ SSGLYSLSSV VTVPSSSLGT QTYICNVNHK
     421 PSNTKVDKKV EPKSEFDYKD DDDKGAPHHH HHH (SEQ ID NO: 67)
//
```

FIG. 6

```
FEATURES             Location/Qualifiers
    Region           1..110
                     /label=Vl3_4
    Region           111..213
                     /label=CL lambda
                     /note="Human C lambda 1 domain, Genbank P01842"
    Region           215..333
                     /label=VH3_15_1
    Region           334..435
                     /label=CH1
                     /note="Human IgG1 CH1 domain, Genbank A49444"
    Region           436..437
                     /label=EcoRI linker
                     /note=-
    Region           438..445
                     /label=M2Flag tag
                     /note=8 amino acid tag recognized by the M2 antibody
    Region           446..448
                     /label=Tag linker I
                     /note=-
    Region           449..454
                     /label=His6 tag
                     /note=6 amino acid Histidin tag
    Region           23..33
                     /label=VL CDR1
    Region           45..55
                     /label=VL CDR2
    Region           88..97
                     /label=VL CDR3
    Region           240..249
                     /label=VH CDR1
    Region           261..282
                     /label=VH CDR2
    Region           315..322
                     /label=VH CDR3
ORIGIN
      1 DIELTQPPSV SVSPGQTASI TC------ ---WYQQKPG QAPV------ ------GIPER
     61 FSGSNSGNTA TLTISGTQAE DEADYYC--- --------VFG GGTKLTVLGQ PKAAPSVTLF
    121 PPSSEELQAN KATLVCLISD FYPGAVTVAW KADSSPVKAG VETTTPSKQS NNKYAASSYL
    181 SLTPEQWKSH RSYSCQVTHE GSTVEKTVAP TEA*EVQLVE SGGGLVKPGG SLRLSCAAS-
    241 --------W VRQAPGKGLE -------- -------- --RFTISRDD SKNTLYLQMN
    301 SLKTEDTAVY YCAR------ --WGQGTLVT VSSASTKGPS VFPLAPSSKS TSGGTAALGC
    361 LVKDYFPEPV TVSWNSGALT SGVHTFPAVL QSSGLYSLSS VVTVPSSSLG TQTYICNVNH
    421 KPSNTKVDKK VEPKSEFDYK DDDDKGAPHH HHHH (SEQ ID NO: 68)
//
```

FIG. 7

```
FEATURES             Location/Qualifiers
    Region           1..110
                     /label=V13_4
    Region           111..213
                     /label=CL lambda
                     /note="Human C lambda 1 domain, Genbank P01842"
    Region           215..334
                     /label=VH3_15_1
    Region           335..436
                     /label=CH1
                     /note="Human IgG1 CH1 domain, Genbank A49444"
    Region           437..438
                     /label=EcoRI linker
                     /note=-
    Region           439..446
                     /label=M2Flag tag
                     /note=8 amino acid tag recognized by the M2 antibody
    Region           447..449
                     /label=Tag linker I
                     /note=-
    Region           450..455
                     /label=His6 tag
                     /note=6 amino acid Histidin tag
    Region           23..33
                     /label=VL CDR1
    Region           45..55
                     /label=VL CDR2
    Region           88..97
                     /label=VL CDR3
    Region           240..249
                     /label=VH CDR1
    Region           261..282
                     /label=VH CDR2
    Region           315..323
                     /label=VH CDR3
ORIGIN
        1 DIELTQPPSV SVSPGQTASI TC        WYQQKPG QAPV              GIPER
       61 FSGSNSGNTA TLTISGTQAE DEADYYC         VFG GGTKLTVLGQ PKAAPSVTLF
      121 PPSSEELQAN KATLVCLISD FYPGAVTVAW KADSSPVKAG VETTTPSKQS NNKYAASSYL
      181 SLTPEQWKSH RSYSCQVTHE GSTVEKTVAP TEA*EVQLVE SGGGLVKPGG SLRLSCAAS
      241          W VRQAPGKGLE                            RFTISRDD SKNTLYLQMN
      301 SLKTEDTAVY YCAR          WGQGTLV TVSSASTKGP SVFPLAPSSK STSGGTAALG
      361 CLVKDYFPEP VTVSWNSGAL TSGVHTFPAV LQSSGLYSLS SVVTVPSSSL GTQTYICNVN
      421 HKPSNTKVDK KVEPKSEFDY KDDDDKGAPH HHHHH (SEQ ID NO: 69)
//
```

FIG. 8

```
FEATURES            Location/Qualifiers
     Region         1..109
                    /label=Vl3_4
     Region         110..212
                    /label=CL lambda
                    /note="Human C lambda 1 domain, Genbank P01842"
     Region         214..333
                    /label=VH1A_4
     Region         334..435
                    /label=CH1
                    /note="Human IgG1 CH1 domain, Genbank A49444"
     Region         436..437
                    /label=EcoRI linker
                    /note=-
     Region         438..445
                    /label=M2Flag tag
                    /note=8 amino acid tag recognized by the M2 antibody
     Region         446..448
                    /label=Tag linker I
                    /note=-
     Region         449..454
                    /label=His6 tag
                    /note=6 amino acid Histidin tag
     Region         23..33
                    /label=VL CDR1
     Region         45..55
                    /label=VL CDR2
     Region         88..96
                    /label=VL CDR3
     Region         239..248
                    /label=VH CDR1
     Region         260..279
                    /label=VH CDR2
     Region         312..322
                    /label=VH CDR3
ORIGIN
        1 DIELTQPPSV SVSPGQTASI TC........ ..WYQQKPG QAPV..... .....GIPER
       61 FSGSNSGNTA TLTISGTQAE DEADYYC... ......VFGG GTKLTVLGQP KAAPSVTLFP
      121 PSSEELQANK ATLVCLISDF YPGAVTVAWK ADSSPVKAGV ETTTPSKQSN NKYAASSYLS
      181 LTPEQWKSHR SYSCQVTHEG STVEKTVAPT EA*QVQLVQS GAEVKKPGSS VKVSCKAS..
      241 ........WV RQAPGQGLE. ......... ........R VTITADESTS TAYMELSSLR
      301 SEDTAVYYCA R......... .WGQGTLVT VSSASTKGPS VFPLAPSSKS TSGGTAALGC
      361 LVKDYFPEPV TVSWNSGALT SGVHTFPAVL QSSGLYSLSS VVTVPSSSLG TQTYICNVNH
      421 KPSNTKVDKK VEPKSEFDYK DDDDKGAPHH HHHH (SEQ ID NO: 70)
//
```

FIG. 9

```
FEATURES            Location/Qualifiers
    Region          1..110
                    /label=Vl3_4
    Region          111..213
                    /label=CL lambda
                    /note="Human C lambda 1 domain, Genbank P01842"
    Region          215..338
                    /label=VH3_23_4
    Region          339..440
                    /label=CH1
                    /note="Human IgG1 CH1 domain, Genbank A49444"
    Region          441..442
                    /label=EcoRI linker
                    /note=-
    Region          443..450
                    /label=M2Flag tag
                    /note=8 amino acid tag recognized by the M2 antibody
    Region          451..453
                    /label=Tag linker I
                    /note=-
    Region          454..459
                    /label=His6 tag
                    /note=6 amino acid Histidin tag
    Region          23..33
                    /label=VL CDR1
    Region          45..55
                    /label=VL CDR2
    Region          88..97
                    /label=VL CDR3
    Region          240..249
                    /label=VH CDR1
    Region          261..280
                    /label=VH CDR2
    Region          313..327
                    /label=VH CDR3
ORIGIN
      1 DIELTQPPSV SVSPGQTASI TC░░░░░░░ ░░WYQQKPG QAPV░░░░░ ░░░░░GIPER
     61 FSGSNSGNTA TLTISGTQAE DEADYYC░░░ ░░░░░░░VFG GGTKLTVLGQ PKAAPSVTLF
    121 PPSSEELQAN KATLVCLISD FYPGAVTVAW KADSSPVKAG VETTTPSKQS NNKYAASSYL
    181 SLTPEQWKSH RSYSCQVTHE GSTVEKTVAP TEA*EVQLLE SGGGLVQPGG SLRLSCAAS░
    241 ░░░░░░░░W VRQAPGKGLE ░░░░░░░░░ ░░░░░░░░░ RFTISRDNSK NTLYLQMNSL
    301 RAEDTAVYYC AR░░░░░░░ ░░░░░░░WGQ GTLVTVSSAS TKGPSVFPLA PSSKSTSGGT
    361 AALGCLVKDY FPEPVTVSWN SGALTSGVHT FPAVLQSSGL YSLSSVVTVP SSSLGTQTYI
    421 CNVNHKPSNT KVDKKVEPKS EFDYKDDDDK GAPHHHHHH (SEQ ID NO: 71)
//
```

FIG. 10

```
FEATURES             Location/Qualifiers
     Region          1..110
                     /label=Vk1_5
     Region          111..215
                     /label=CL kappa
                     /note="Human C kappa light chain constant region,
Genbank P01834"
     Region          217..345
                     /label=VH3_23_4
     Region          346..447
                     /label=CH1
                     /note="Human IgG1 CH1 domain, Genbank A49444"
     Region          448..449
                     /label=EcoRI linker
                     /note=-
     Region          450..457
                     /label=M2Flag tag
                     /note=8 amino acid tag recognized by the M2 antibody
     Region          458..460
                     /label=Tag linker I
                     /note=-
     Region          461..466
                     /label=His6 tag
                     /note=6 amino acid Histidin tag
     Region          24..35
                     /label=VL CDR1
     Region          47..57
                     /label=VL CDR2
     Region          90..97
                     /label=VL CDR3
     Region          242..251
                     /label=VH CDR1
     Region          263..282
                     /label=VH CDR2
     Region          315..334
                     /label=VH CDR3
ORIGIN
       1 DIQMTQSPSS LSASVGDRVT ITC                WYQQK PGKAPK            GVP
      61 SRFSGSGSGT DFTLTISSLQ PEDFATYYC              TFG QGTKVEIKRT VAAPSVFIFP
     121 PSDEQLKSGT ASVVCLLNNF YPREAKVQWK VDNALQSGNS QESVTEQDSK DSTYSLSSTL
     181 TLSKADYEKH KVYACEVTHQ GLSSPVTKSF NRGEA*EVQL LESGGGLVQP GGSLRLSCAA
     241 S            WVRQAPGKG LE                         RFTISRDN SKNTLYLQMN
     301 SLRAEDTAVY YCAR                      WGQGTL VTVSSASTKG PSVFPLAPSS
     361 KSTSGGTAAL GCLVKDYFPE PVTVSWNSGA LTSGVHTFPA VLQSSGLYSL SSVVTVPSSS
     421 LGTQTYICNV NHKPSNTKVD KKVEPKSEFD YKDDDDKGAP HHHHHH (SEQ ID NO: 72)
//
```

FIG. 11

```
FEATURES             Location/Qualifiers
    Region           1..108
                     /label=Vl3_4
    Region           109..211
                     /label=CL lambda
                     /note="Human C lambda 1 domain, Genbank P01842"
    Region           213..328
                     /label=VH3_23_4
    Region           329..430
                     /label=CH1
                     /note="Human IgG1 CH1 domain, Genbank A49444"
    Region           431..432
                     /label=EcoRI linker
                     /note=-
    Region           433..440
                     /label=M2Flag tag
                     /note=8 amino acid tag recognized by the M2 antibody
    Region           441..443
                     /label=Tag linker I
                     /note=-
    Region           444..449
                     /label=His6 tag
                     /note=6 amino acid Histidin tag
    Region           23..33
                     /label=VL CDR1
    Region           45..55
                     /label=VL CDR2
    Region           88..95
                     /label=VL CDR3
    Region           238..247
                     /label=VH CDR1
    Region           259..278
                     /label=VH CDR2
    Region           311..317
                     /label=VH CDR3
ORIGIN
        1 DIELTQPPSV SVSPGQTASI TC        WYQQKPG QAPV              GIPER
       61 FSGSNSGNTA TLTISGTQAE DEADYYC        VFGGG TKLTVLGQPK AAPSVTLFPP
      121 SSEELQANKA TLVCLISDFY PGAVTVAWKA DSSPVKAGVE TTTPSKQSNN KYAASSYLSL
      181 TPEQWKSHRS YSCQVTHEGS TVEKTVAPTE A*EVQLLESG GGLVQPGGSL RLSCAAS
      241        WVR QAPGKGLE                    RF TISRDNSKNT LYLQMNSLRA
      301 EDTAVYYCAR       WGQ GTLVTVSSAS TKGPSVFPLA PSSKSTSGGT AALGCLVKDY
      361 FPEPVTVSWN SGALTSGVHT FPAVLQSSGL YSLSSVVTVP SSSLGTQTYI CNVNHKPSNT
      421 KVDKKVEPKS EFDYKDDDDK GAPHHHHHH  (SEQ ID NO: 73)
//
```

FIG. 12

```
FEATURES             Location/Qualifiers
     Region          1..108
                     /label=V13_4
     Region          109..211
                     /label=CL lambda
                     /note="Human C lambda 1 domain, Genbank P01842"
     Region          213..332
                     /label=VH3_23_4
     Region          333..434
                     /label=CH1
                     /note="Human IgG1 CH1 domain, Genbank A49444"
     Region          435..436
                     /label=EcoRI linker
                     /note=-
     Region          437..444
                     /label=M2Flag tag
                     /note=8 amino acid tag recognized by the M2 antibody
     Region          445..447
                     /label=Tag linker I
                     /note=-
     Region          448..453
                     /label=His6 tag
                     /note=6 amino acid Histidin tag
     Region          23..33
                     /label=VL CDR1
     Region          45..55
                     /label=VL CDR2
     Region          88..95
                     /label=VL CDR3
     Region          238..247
                     /label=VH CDR1
     Region          259..278
                     /label=VH CDR2
     Region          311..321
                     /label=VH CDR3
ORIGIN
       1 DIELTQPPSV SVSPGQTASI TC        WYQQKPG QAPV            GIPER
      61 FSGSNSGNTA TLTISGTQAE DEADYYC        VFGGG TKLTVLGQPK AAPSVTLFPP
     121 SSEELQANKA TLVCLISDFY PGAVTVAWKA DSSPVKAGVE TTTPSKQSNN KYAASSYLSL
     181 TPEQWKSHRS YSCQVTHEGS TVEKTVAPTE A*EVQLLESG GGLVQPGGSL RLSCAAS
     241         WVR QAPGKGLE               RF TISRDNSKNT LYLQMNSLRA
     301 EDTAVYYCAR            WGQGTLVTV SSASTKGPSV FPLAPSSKST SGGTAALGCL
     361 VKDYFPEPVT VSWNSGALTS GVHTFPAVLQ SSGLYSLSSV VTVPSSSLGT QTYICNVNHK
     421 PSNTKVDKKV EPKSEFDYKD DDDKGAPHHH HHH (SEQ ID NO: 74)
//
```

FIG. 13

```
FEATURES             Location/Qualifiers
     Region          1..112
                     /label=Vl1_5a
     Region          113..215
                     /label=CL lambda
                     /note="Human C lambda 1 domain, Genbank P01842"
     Region          217..333
                     /label=VH1A_4
     Region          334..435
                     /label=CH1
                     /note="Human IgG1 CH1 domain, Genbank A49444"
     Region          436..437
                     /label=EcoRI linker
                     /note=-
     Region          438..445
                     /label=M2Flag tag
                     /note=8 amino acid tag recognized by the M2 antibody
     Region          446..448
                     /label=Tag linker I
                     /note=-
     Region          449..454
                     /label=His6 tag
                     /note=6 amino acid Histidin tag
     Region          23..35
                     /label=VL CDR1
     Region          47..57
                     /label=VL CDR2
     Region          90..99
                     /label=VL CDR3
     Region          242..251
                     /label=VH CDR1
     Region          263..282
                     /label=VH CDR2
     Region          315..322
                     /label=VH CDR3
ORIGIN
        1 DIVLTQPPSV SGAPGQRVTI SC         WYQQL PGTAPK           GVP
       61 DRFSGSKSGT SASLAITGLQ AEDEADYYC          V FGGGTKLTVL GQPKAAPSVT
      121 LFPPSSEELQ ANKATLVCLI SDFYPGAVTV AWKADSSPVK AGVETTTPSK QSNNKYAASS
      181 YLSLTPEQWK SHRSYSCQVT HEGSTVEKTV APTEA*QVQL VQSGAEVKKP GSSVKVSCKA
      241 S           WVRQAPGQG LE                       RVTITADE STSTAYMELS
      301 SLRSEDTAVY YCAR         WGQGTLVT VSSASTKGPS VFPLAPSSKS TSGGTAALGC
      361 LVKDYFPEPV TVSWNSGALT SGVHTFPAVL QSSGLYSLSS VVTVPSSSLG TQTYICNVNH
      421 KPSNTKVDKK VEPKSEFDYK DDDDKGAPHH HHHH (SEQ ID NO: 75)
//
```

ALK2 ANTIBODIES AND METHODS OF USE THEREOF

SEQUENCE LISTING

The instant application contains a Sequence Listing which has been submitted electronically in ASCII format and is hereby incorporated by reference in its entirety. Said ASCII copy, created on Apr. 21, 2021 is named 51184-010003_Sequence_Listing_04.21.21_ST25 and is 55,306 bytes in size.

BACKGROUND OF THE INVENTION

Healthy bone undergoes a constant remodeling that involves both bone breakdown and bone growth. Bone growth is mediated by the osteoblast cell type whereas the osteoclasts resorb the bone. Pathology occurs when these systems fall out of balance either through downregulation of the anabolic program, upregulation of the catabolic system or a combination of both, resulting in a net bone loss. Therefore, controlling the balance in bone remodeling can be useful for promoting the healing of damage to bone as well as the treatment of disorders, such as osteoporosis, associated with loss of bone mass and bone demineralization.

Bone damage can result from a range of root causes, including age- or cancer-related bone loss, genetic conditions, or adverse side effects of drug treatment. The World Health Organization estimates that osteoporosis alone affects 75 million people in the U.S., Europe and Japan, and is a significant risk factor in bone damage. In general, the whole of bone loss represents pathological states for which there are few effective treatments. Treatment instead focuses on immobilization, exercise and dietary modifications rather than agents that directly promote bone growth and increase bone density. With respect to osteoporosis, estrogen, calcitonin, osteocalcin with vitamin K, or high doses of dietary calcium are all used as therapeutic interventions. Other therapeutic approaches to osteoporosis include bisphosphonates, parathyroid hormone, parathyroid hormone related protein (PTHrP), calcimimetics, statins, anabolic steroids, lanthanum and strontium salts, and sodium fluoride. Such therapeutics, however, are often associated with undesirable side effects.

Anemia is a global health problem with health implications that affect both morbidity and mortality. In the United States alone, the prevalence of anemia nearly doubled from 2003 to 2012. Symptoms of anemia include fatigue, weakness, shortness of breath, heart palpitations, and reduced cognitive performance, and children, pregnant women, women of reproductive age, and the elderly have been found to have the highest risk of developing anemia. The most common form of anemia is iron deficiency anemia, but anemia can also be caused by chronic diseases, blood loss, and red blood cell destruction. While iron deficiency anemia can be treated with iron supplements, many other forms of anemia, such as aplastic anemia, anemia of chronic disease, and hemolytic anemia may require blood transfusions.

Heterotopic ossification (HO) is the pathologic formation of extra-skeletal bone in soft tissues. This process occurs in patient populations with severe trauma, including large-surface area burns, musculoskeletal injury, orthopedic operations, and spinal cord injury, and in patient populations with a genetic disease known as fibrodysplasia ossificans progressiva (FOP). FOP is caused by a hyper-activating mutation in the type I bone morphogenetic protein (BMP) receptor activin A receptor type I (ACVR1), and patients with FOP can develop ectopic bone lesions in muscles, tendons, ligaments, and other connective tissues in the absence of any substantial trauma. The clinical sequela of these pathologic ectopic bone formations, whether in the setting of trauma or genetic mutations, include non-healing wounds, chronic pain, and joint immobility. In the case of FOP, the formation of ectopic bone can lead to bridges of bone that develop across joints and progressively restrict movement and progressive ossification may lead to death due to loss of thoracic cage compliance.

Treatment options for HO are limited as bone often recurs following surgical resection, and attempts to surgically remove extra bone can result in further bone growth. Moreover, some patients may have non-resectable HO due to its sensitive location. The risk of an operation may outweigh the benefits of excision, especially in the face of recurrence. There is a need for therapeutic options that can prevent HO before its initial occurrence in at-risk patients and/or reduce the amount of HO, reduce the recurrence of HO, or prevent additional ectopic bone formation in patients with FOP. There is currently no approved treatment for FOP.

Sjogren's syndrome is a systemic autoimmune disorder identified by its two most common symptoms—dry eye and dry mouth. It may also feature joint pain, swelling, and stiffness, swollen salivary glands, skin rashes or dry skin, vaginal dryness, persistent dry cough, and prolonged fatigue. Sjogren's can also cause dysfunction of organs such as the kidneys, gastrointestinal system, blood vessels, lungs, liver, pancreas, and the central nervous system. It is one of the most prevalent autoimmune disorders with over four million Americans suffering from the disorder, nine out of ten of which are women. Dry eye associated with Sjogren's syndrome may be treated with immunosuppressants and steroid eye drops; however, due to side effects such as increased intraocular pressure and susceptibility to infection, steroid eye drops should not be used for an extended period of time.

Diffuse intrinsic pontine glioma (DIPG) is a pediatric brain tumor that originates in the pons and accounts for approximately 20% of all pediatric brain tumors. DIPG remains incurable with a median survival of 10-11 months. Failure to identify a successful therapy for DIPG likely stems from the lack of biological understanding of the disease, as biopsies were not commonly performed until recently due to the sensitive location of the tumor. As a result, many trials have been based upon genetic alterations found in adult glioblastomas, which have recently been found to be molecularly distinct from DIPG.

Multiple osteochondroma (MO), also called hereditary multiple exostoses, is a rare genetic disorder characterized by the development of multiple benign (noncancerous) bone tumors called osteochondromas, often on the growing end (metaphysis) of the long bones of the legs, arms, and digits and on flat bones such as the hip and shoulder blade. The number of osteochondromas and the bones on which they are located vary greatly among affected individuals. The osteochondromas are not present at birth, but approximately 96% of affected individuals develop multiple osteochondromas by the time they are 12 years old. These osteochondromas usually continue to grow until shortly after puberty and may lead to bone deformities, skeletal abnormalities, differences in limb length, short stature, pain, decreased range of motion, and pressure on nerves, blood vessels, the spinal cord, and tissues surrounding the osteochondromas. Hereditary multiple osteochondromas is inherited as an autosomal dominant genetic condition and is associated with mutations in the exostosin-1 (EXT1) or exostosin-2 (EXT2) gene. Current treatment options include a "watch and wait" approach (when no symptoms are present), surgical removal of the osteochondroma, corrective osteotomy, and growth plate arrest or limb-lengthening procedures.

Posterior capsule opacification (PCO) is the most frequent complication associated with decreased vision after cataract surgery and intraocular lens implantation. During cataract surgery, the natural lens of the eye is replaced with an artificial intraocular lens, which is placed inside the lens capsule. PCO occurs when lens epithelial cells migrate toward the posterior capsule, proliferate, and differentiate, growing over the back of the capsule and causing it to thicken and become slightly opaque. This reduces the amount of light that can reach the retina and may lead to blurred or cloudy vision or problems with bright lights and glare. Although PCO can be treated using Nd:YAG laser capsulotomy, the potential complications and significant cost of treatment underscore the importance of identifying new PCO therapies.

Cardiac hypertrophy is the abnormal enlargement or thickening of the heart muscle resulting from increases in cardiomyocyte size and changes in other heart muscle components, such as extracellular matrix. Cardiac hypertrophy may be physiological, occurring in response to exercise or pregnancy, or pathological, occurring in response to stress (e.g., hemodynamic stress), such as hypertension or valvular disease. Cardiac fibrosis may also feature an abnormal thickening of the heart valves due to inappropriate proliferation of cardiac fibroblasts or excess deposition of extracellular matrix in the cardiac muscle, which may result in stiffer, less compliant muscle and occur during the progression to heart failure. There is a lack of efficacious therapies for reducing or reversing cardiac fibrosis, and existing therapies for cardiac hypertrophy, such as adrenergic antagonists, renin-angiotensin system modulators such as angiotensin-converting enzyme (ACE) inhibitors, and angiotensin receptor blockers may have a ceiling effect, characterized by a lack of efficacy, and even regression, in some patients.

There exists a need for novel and effective treatments for bone diseases, anemia, HO (e.g., HO resulting from FOP), Sjogren's syndrome (e.g., dry eye associated with Sjogren's syndrome), DIPG, MO, PCO, and cardiac hypertrophy and/or cardiac fibrosis.

SUMMARY OF THE INVENTION

Described herein are activin receptor-like kinase-2 (ALK2, also known as activin A receptor type I (ACVR1)) antibodies, such as ALK2 neutralizing antibodies and ALK2 binding fragments thereof. The ALK2 antibodies and antigen binding fragments thereof described herein can be formulated in a pharmaceutical composition for administration to a subject, such as a human subject. The ALK2 antibodies or antigen binding fragments thereof and compositions described herein can be administered to a subject, such as a human subject, to treat or prevent bone disease (e.g., a disease or condition involving bone damage, such as primary osteoporosis, secondary osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss), low red blood cell levels (e.g., low hemoglobin levels or low red blood cell count, e.g., anemia), heterotopic ossification (HO), such as heterotopic ossification resulting from Fibrodysplasia ossificans progressiva (FOP), Sjogren's syndrome (e.g., dry eye associated with Sjogren's syndrome), diffuse intrinsic pontine glioma (DIPG), multiple osteochondroma (MO), posterior capsule opacification (PCO), or cardiac hypertrophy and/or cardiac fibrosis.

Exemplary embodiments of the invention are described in the enumerated paragraphs below.

E1. An isolated antibody, or ALK2 binding fragment thereof, including (1) a light chain variable domain including a light chain complementarity determining region (CDR) 1 including or consisting of an amino acid sequence selected from SGSSSNIGSNYVS (SEQ ID NO:1) and SGDX$_1$X$_2$X$_3$X$_4$X$_5$X$_6$X$_7$X$_8$ (SEQ ID NO:2, where X$_1$ is S or N, X$_2$ is I or L, X$_3$ is P, G, or R, X$_4$ is S, T, or K, X$_5$ is F, K, or Y, X$_6$ is F, Y, or S, X$_7$ is A or V, and X$_8$ is S, Y, or H); a light chain CDR2 including or consisting of the amino acid sequence X$_1$X$_2$IYX$_3$X$_4$X$_5$X$_6$RPS (SEQ ID NO:3, where X$_1$ is V or L, X$_2$ is V or L, X$_3$ is K, R, G or Y, X$_4$ is N or D, X$_5$ is N or S, and X$_6$ is H, N, D, or K); and a light chain CDR3 including or consisting of an amino acid sequence selected from ASWDHSDRFYV (SEQ ID NO:4), YVTAPWKSIW (SEQ ID NO:5), YSADAQQMKA (SEQ ID NO:6), QVYASVHRM (SEQ ID NO:7), and QTYDWSHFGW (SEQ ID NO:8); and (2) a heavy chain variable domain including a heavy chain CDR1 including or consisting of the amino acid sequence GX$_1$TFX$_2$SX$_3$X$_4$X$_5$X$_6$ (SEQ ID NO:9, where X$_1$ is G or F, X$_2$ is S or N, X$_3$ is Y, H, S, or A, X$_4$ is G or A, X$_5$ is V, M, or I, and X$_6$ is S or H); a heavy chain CDR2 including or consisting of an amino acid sequence selected from WMGX$_1$IIPX$_2$FGX$_3$ANYAQKFQG (SEQ ID NO:10, where X$_1$ is G or R, X$_2$ is H or D, and X$_3$ is I or T), WVGRIKSKX$_1$DX$_2$X$_3$TTDYAAPVKG (SEQ ID NO:11, where X$_1$ is A or R, X$_2$ is S or G, and X$_3$ is G or Y), and WVSVISSDGGSTYYADSVKG (SEQ ID NO:12); and a heavy chain CDR3 including or consisting of an amino acid sequence selected from EIGSLDI (SEQ ID NO:13), DYGVAFAY (SEQ ID NO:14), DYGGLKFDY (SEQ ID NO:15), GPTQAIHYFAY (SEQ ID NO:16), and AGFILGSLGVAWMDV (SEQ ID NO:17).

E2. The isolated antibody, or ALK2 binding fragment thereof, of E1, wherein the light chain CDR1 includes or consists of the sequence of SEQ ID NO: 2 and X$_1$ is S.

E3. The isolated antibody, or ALK2 binding fragment thereof, of E1, wherein the light chain CDR1 includes or consists of the sequence of SEQ ID NO: 2 and X$_1$ is N.

E4. The isolated antibody, or ALK2 binding fragment thereof, of any one of E1-E3, wherein the light chain CDR1 includes or consists of the sequence of SEQ ID NO: 2 X$_2$ is I.

E5. The isolated antibody, or ALK2 binding fragment thereof, of any one of E1-E3, wherein the light chain CDR1 includes or consists of the sequence of SEQ ID NO: 2 X$_2$ is L.

E6. The isolated antibody, or ALK2 binding fragment thereof, of any one of E1-E5, wherein the light chain CDR1 includes or consists of the sequence of SEQ ID NO: 2 and X$_3$ is P.

E7. The isolated antibody, or ALK2 binding fragment thereof, of any one of E1-E5, wherein the light chain CDR1 includes or consists of the sequence of SEQ ID NO: 2 and X$_3$ is G.

E8. The isolated antibody, or ALK2 binding fragment thereof, of any one of E1-E5, wherein the light chain CDR1 includes or consists of the sequence of SEQ ID NO: 2 and X$_3$ is R.

E9. The isolated antibody, or ALK2 binding fragment thereof, of any one of E1-E8, wherein the light chain CDR1 includes or consists of the sequence of SEQ ID NO: 2 and $X_4$ is S.

E10. The isolated antibody, or ALK2 binding fragment thereof, of any one of E1-E8, wherein the light chain CDR1 includes or consists of the sequence of SEQ ID NO: 2 and $X_4$ is T.

E11. The isolated antibody, or ALK2 binding fragment thereof, of any one of E1-E8, wherein the light chain CDR1 includes or consists of the sequence of SEQ ID NO: 2 and $X_4$ is K.

E12. The isolated antibody, or ALK2 binding fragment thereof, of any one of E1-E11, wherein the light chain CDR1 includes or consists of the sequence of SEQ ID NO: 2 and $X_5$ is F.

E13. The isolated antibody, or ALK2 binding fragment thereof, of any one of E1-E11, wherein the light chain CDR1 includes or consists of the sequence of SEQ ID NO: 2 and $X_5$ is K.

E14. The isolated antibody, or ALK2 binding fragment thereof, of any one of E1-E11, wherein the light chain CDR1 includes or consists of the sequence of SEQ ID NO: 2 and $X_5$ is Y.

E15. The isolated antibody, or ALK2 binding fragment thereof, of any one of E1-E14, wherein the light chain CDR1 includes or consists of the sequence of SEQ ID NO: 2 and $X_6$ is F.

E16. The isolated antibody, or ALK2 binding fragment thereof, of any one of E1-E14, wherein the light chain CDR1 includes or consists of the sequence of SEQ ID NO: 2 and $X_6$ is Y.

E17. The isolated antibody, or ALK2 binding fragment thereof, of any one of E1-E14, wherein the light chain CDR1 includes or consists of the sequence of SEQ ID NO: 2 and $X_6$ is S.

E18. The isolated antibody, or ALK2 binding fragment thereof, of any one of E1-E17, wherein the light chain CDR1 includes or consists of the sequence of SEQ ID NO: 2 and $X_7$ is A.

E19. The isolated antibody, or ALK2 binding fragment thereof, of any one of E1-E17, wherein the light chain CDR1 includes or consists of the sequence of SEQ ID NO: 2 and $X_7$ is V.

E20. The isolated antibody, or ALK2 binding fragment thereof, of any one of E1-E19, wherein the light chain CDR1 includes or consists of the sequence of SEQ ID NO: 2 and $X_8$ is S.

E21. The isolated antibody, or ALK2 binding fragment thereof, of any one of E1-E19, wherein the light chain CDR1 includes or consists of the sequence of SEQ ID NO: 2 and $X_8$ is Y.

E22. The isolated antibody, or ALK2 binding fragment thereof, of any one of E1-E19, wherein the light chain CDR1 includes or consists of the sequence of SEQ ID NO: 2 and $X_7$ is A or V, and $X_8$ is H.

E23. The isolated antibody, or ALK2 binding fragment thereof, of any one of E1-E22, wherein the light chain CDR2 includes or consists of the sequence of SEQ ID NO: 3 and $X_1$ is V.

E24. The isolated antibody, or ALK2 binding fragment thereof, of any one of E1-E22, wherein the light chain CDR2 includes or consists of the sequence of SEQ ID NO: 3 and $X_1$ is L.

E25. The isolated antibody, or ALK2 binding fragment thereof, of any one of E1-E24, wherein the light chain CDR2 includes or consists of the sequence of SEQ ID NO: 3 and $X_2$ is V.

E26. The isolated antibody, or ALK2 binding fragment thereof, of any one of E1-E24, wherein the light chain CDR2 includes or consists of the sequence of SEQ ID NO: 3 and $X_2$ is L.

E27. The isolated antibody, or ALK2 binding fragment thereof, of any one of E1-E26, wherein the light chain CDR2 includes or consists of the sequence of SEQ ID NO: 3 and $X_3$ is K.

E28. The isolated antibody, or ALK2 binding fragment thereof, of any one of E1-E26, wherein the light chain CDR2 includes or consists of the sequence of SEQ ID NO: 3 and $X_3$ is R.

E29. The isolated antibody, or ALK2 binding fragment thereof, of any one of E1-E26, wherein the light chain CDR2 includes or consists of the sequence of SEQ ID NO: 3 and $X_3$ is G.

E30. The isolated antibody, or ALK2 binding fragment thereof, of any one of E1-E26, wherein the light chain CDR2 includes or consists of the sequence of SEQ ID NO: 3 and $X_3$ is Y.

E31. The isolated antibody, or ALK2 binding fragment thereof, of any one of E1-E30, wherein the light chain CDR2 includes or consists of the sequence of SEQ ID NO: 3 and $X_4$ is N.

E32. The isolated antibody, or ALK2 binding fragment thereof, of any one of E1-E30, wherein the light chain CDR2 includes or consists of the sequence of SEQ ID NO: 3 and $X_4$ is D.

E33. The isolated antibody, or ALK2 binding fragment thereof, of any one of E1-E32, wherein the light chain CDR2 includes or consists of the sequence of SEQ ID NO: 3 and $X_5$ is N.

E34. The isolated antibody, or ALK2 binding fragment thereof, of any one of E1-E32, wherein the light chain CDR2 includes or consists of the sequence of SEQ ID NO: 3 and $X_5$ is S.

E35. The isolated antibody, or ALK2 binding fragment thereof, of any one of E1-E34, wherein the light chain CDR2 includes or consists of the sequence of SEQ ID NO: 3 and $X_6$ is H.

E36. The isolated antibody, or ALK2 binding fragment thereof, of any one of E1-E34, wherein the light chain CDR2 includes or consists of the sequence of SEQ ID NO: 3 and $X_6$ is N.

E37. The isolated antibody, or ALK2 binding fragment thereof, of any one of E1-E34, wherein the light chain CDR2 includes or consists of the sequence of SEQ ID NO: 3 and $X_6$ is D.

E38. The isolated antibody, or ALK2 binding fragment thereof, of any one of E1-E34, wherein the light chain CDR2 includes or consists of the sequence of SEQ ID NO: 3 and $X_6$ is K.

E39. The isolated antibody, or ALK2 binding fragment thereof, of any one of E1-E38, wherein the heavy chain CDR1 includes or consists of the sequence of SEQ ID NO:9 and $X_1$ is G.

E40. The isolated antibody, or ALK2 binding fragment thereof, of any one of E1-E38, wherein the heavy chain CDR1 includes or consists of the sequence of SEQ ID NO:9 and $X_1$ is F.

E41. The isolated antibody, or ALK2 binding fragment thereof, of any one of E1-E40, wherein the heavy chain CDR1 includes or consists of the sequence of SEQ ID NO:9 and $X_2$ is S.

E42. The isolated antibody, or ALK2 binding fragment thereof, of any one of E1-E40, wherein the heavy chain CDR1 includes or consists of the sequence of SEQ ID NO:9 and $X_2$ is N.

E43. The isolated antibody, or ALK2 binding fragment thereof, of any one of E1-E42, wherein the heavy chain CDR1 includes or consists of the sequence of SEQ ID NO:9 and $X_3$ is Y.

E44. The isolated antibody, or ALK2 binding fragment thereof, of any one of E1-E42, wherein the heavy chain CDR1 includes or consists of the sequence of SEQ ID NO:9 and $X_3$ is H.

E45. The isolated antibody, or ALK2 binding fragment thereof, of any one of E1-E42, wherein the heavy chain CDR1 includes or consists of the sequence of SEQ ID NO:9 and $X_3$ is S.

E46. The isolated antibody, or ALK2 binding fragment thereof, of any one of E1-E42, wherein the heavy chain CDR1 includes or consists of the sequence of SEQ ID NO:9 and $X_3$ is A.

E47. The isolated antibody, or ALK2 binding fragment thereof, of any one of E1-E46, wherein the heavy chain CDR1 includes or consists of the sequence of SEQ ID NO:9 and $X_4$ is G.

E48. The isolated antibody, or ALK2 binding fragment thereof, of any one of E1-E46, wherein the heavy chain CDR1 includes or consists of the sequence of SEQ ID NO:9 and $X_4$ is A.

E49. The isolated antibody, or ALK2 binding fragment thereof, of any one of E1-E48, wherein the heavy chain CDR1 includes or consists of the sequence of SEQ ID NO:9 and $X_5$ is V.

E50. The isolated antibody, or ALK2 binding fragment thereof, of any one of E1-E48, wherein the heavy chain CDR1 includes or consists of the sequence of SEQ ID NO:9 and $X_5$ is M.

E51. The isolated antibody, or ALK2 binding fragment thereof, of any one of E1-E48, wherein the heavy chain CDR1 includes or consists of the sequence of SEQ ID NO:9 and $X_5$ is I.

E52. The isolated antibody, or ALK2 binding fragment thereof, of any one of E1-E51, wherein the heavy chain CDR1 includes or consists of the sequence of SEQ ID NO:9 and $X_6$ is S.

E53. The isolated antibody, or ALK2 binding fragment thereof, of any one of E1-E51, wherein the heavy chain CDR1 includes or consists of the sequence of SEQ ID NO:9 and $X_6$ is H.

E54. The isolated antibody, or ALK2 binding fragment thereof, of any one of E1-E53, wherein the heavy chain CDR2 includes or consists of the sequence of SEQ ID NO:10 and $X_1$ is G.

E55. The isolated antibody, or ALK2 binding fragment thereof, of any one of E1-E53, wherein the heavy chain CDR2 includes or consists of the sequence of SEQ ID NO:10 and $X_1$ is R.

E56. The isolated antibody, or ALK2 binding fragment thereof, of any one of E1-E55, wherein the heavy chain CDR2 includes or consists of the sequence of SEQ ID NO:10 and $X_2$ is H.

E57. The isolated antibody, or ALK2 binding fragment thereof, of any one of E1-E55, wherein the heavy chain CDR2 includes or consists of the sequence of SEQ ID NO:10 and $X_2$ is D.

E58. The isolated antibody, or ALK2 binding fragment thereof, of any one of E1-E57, wherein the heavy chain CDR2 includes or consists of the sequence of SEQ ID NO:10 and $X_3$ is I.

E59. The isolated antibody, or ALK2 binding fragment thereof, of any one of E1-E57, wherein the heavy chain CDR2 includes or consists of the sequence of SEQ ID NO:10 and $X_3$ is T.

E60. The isolated antibody, or ALK2 binding fragment thereof, of any one of E1-E53, wherein the heavy chain CDR2 includes or consists of the sequence of SEQ ID NO:11 and $X_1$ is A.

E61. The isolated antibody, or ALK2 binding fragment thereof, of any one of E1-E53, wherein the heavy chain CDR2 includes or consists of the sequence of SEQ ID NO:11 and $X_1$ is R.

E62. The isolated antibody, or ALK2 binding fragment thereof, of any one of E1-E53, E60, and E61, wherein the heavy chain CDR2 includes or consists of the sequence of SEQ ID NO:11 and $X_2$ is S.

E63. The isolated antibody, or ALK2 binding fragment thereof, of any one of E1-E53, E60, and E61, wherein the heavy chain CDR2 includes or consists of the sequence of SEQ ID NO:11 and $X_2$ is G.

E64. The isolated antibody, or ALK2 binding fragment thereof, of any one of E1-E53 and E60-E63, wherein the heavy chain CDR2 includes or consists of the sequence of SEQ ID NO:11 and $X_3$ is G.

E65. The isolated antibody, or ALK2 binding fragment thereof, of any one of E1-E53 and E60-E63, wherein the heavy chain CDR2 includes or consists of the sequence of SEQ ID NO:11 and $X_3$ is Y.

E66. The isolated antibody, or ALK2 binding fragment thereof, of E1, wherein the light chain CDR1 includes or consists of the sequence SGSSSNIGSNYVS (SEQ ID NO:1).

E67. The isolated antibody, or ALK2 binding fragment thereof, of E1, wherein the light chain CDR1 includes or consists of the sequence SGDSIPSFFAS (SEQ ID NO:18).

E68. The isolated antibody, or ALK2 binding fragment thereof, of E1, wherein the light chain CDR1 includes or consists of the sequence SGDNIGTKYAY (SEQ ID NO:19).

E69. The isolated antibody, or ALK2 binding fragment thereof, of E1, wherein the light chain CDR1 includes or consists of the sequence SGDNLRKYSAH (SEQ ID NO:20).

E70. The isolated antibody, or ALK2 binding fragment thereof, of E1, wherein the light chain CDR1 includes or consists of the sequence SGDSLGSKSVH (SEQ ID NO:21).

E71. The isolated antibody, or ALK2 binding fragment thereof, of any one of E1 and E66-E70, wherein the light chain CDR2 includes or consists of the sequence VLIYKNNHRPS (SEQ ID NO:24).

E72. The isolated antibody, or ALK2 binding fragment thereof, of any one of E1 and E66-E70, wherein the light chain CDR2 includes or consists of the sequence LVIYRDSNRPS (SEQ ID NO:25).

E73. The isolated antibody, or ALK2 binding fragment thereof, of any one of E1 and E66-E70, wherein the light chain CDR2 includes or consists of the sequence LVIYGDSDRPS (SEQ ID NO:26).

E74. The isolated antibody, or ALK2 binding fragment thereof, of any one of E1 and E66-E70, wherein the light chain CDR2 includes or consists of the sequence LVIYYDNKRPS (SEQ ID NO:27).

E75. The isolated antibody, or ALK2 binding fragment thereof, of any one of E1 and E66-E70, wherein the light chain CDR2 includes or consists of the sequence LVIYRDSKRPS (SEQ ID NO:28).

E76. The isolated antibody, or ALK2 binding fragment thereof, of any one of E1 and E66-E75, wherein the light chain CDR3 includes or consists of the sequence ASWDHSDRFYV (SEQ ID NO:4).

E77. The isolated antibody, or ALK2 binding fragment thereof, of any one of E1 and E66-E75, wherein the light chain CDR3 includes or consists of the sequence YVTAPWKSIW (SEQ ID NO:5).

E78. The isolated antibody, or ALK2 binding fragment thereof, of any one of E1 and E66-E75, wherein the light chain CDR3 includes or consists of the sequence YSADAQQMKA (SEQ ID NO:6).

E79. The isolated antibody, or ALK2 binding fragment thereof, of any one of E1 and E66-E75, wherein the light chain CDR3 includes or consists of the sequence QVYASVHRM (SEQ ID NO:7).

E80. The isolated antibody, or ALK2 binding fragment thereof, of any one of E1 and E66-E75, wherein the light chain CDR3 includes or consists of the QTYDWSHFGW (SEQ ID NO:8).

E81. The isolated antibody, or ALK2 binding fragment thereof, of any one of E1 and E66-E80, wherein the heavy chain CDR1 includes or consists of the sequence GGTFSSYGVS (SEQ ID NO:31).

E82. The isolated antibody, or ALK2 binding fragment thereof, of any one of E1 and E66-E80, wherein the heavy chain CDR1 includes or consists of the sequence GFTFSSHAMS (SEQ ID NO:32).

E83. The isolated antibody, or ALK2 binding fragment thereof, of any one of E1 and E66-E80, wherein the heavy chain CDR1 includes or consists of the sequence GFTFNSSAMS (SEQ ID NO:33).

E84. The isolated antibody, or ALK2 binding fragment thereof, of any one of E1 and E66-E80, wherein the heavy chain CDR1 includes or consists of the sequence GGTFSSYAIH (SEQ ID NO:34).

E85. The isolated antibody, or ALK2 binding fragment thereof, of any one of E1 and E66-E80, wherein the heavy chain CDR1 includes or consists of the sequence GFTFSSAAMH (SEQ ID NO:35).

E86. The isolated antibody, or ALK2 binding fragment thereof, of any one of E1 and E66-E85, wherein the heavy chain CDR2 includes or consists of the sequence WMGGIIPHFGIANYAQKFQG (SEQ ID NO: 36).

E87. The isolated antibody, or ALK2 binding fragment thereof, of any one of E1 and E66-E85, wherein the heavy chain CDR2 includes or consists of the sequence WVGRIKSKADSGTTDYAAPVKG (SEQ ID NO: 37).

E88. The isolated antibody, or ALK2 binding fragment thereof, of any one of E1 and E66-E85, wherein the heavy chain CDR2 includes or consists of the sequence WVGRIKSKRDGYTTDYAAPVKG (SEQ ID NO: 38).

E89. The isolated antibody, or ALK2 binding fragment thereof, of any one of E1 and E66-E85, wherein the heavy chain CDR2 includes or consists of the sequence WMGRIIPDFGTANYAQKFQG (SEQ ID NO: 39).

E90. The isolated antibody, or ALK2 binding fragment thereof, of any one of E1 and E66-E85, wherein the heavy chain CDR2 includes or consists of the sequence WVSVISSDGGSTYYADSVKG (SEQ ID NO: 12).

E91. The isolated antibody, or ALK2 binding fragment thereof, of any one of E1 and E66-E90, wherein
the heavy chain CDR3 includes or consists of the sequence EIGSLDI (SEQ ID NO:13).

E92. The isolated antibody, or ALK2 binding fragment thereof, of any one of E1 and E66-E90, wherein the heavy chain CDR3 includes or consists of the sequence DYGVAFAY (SEQ ID NO:14).

E93. The isolated antibody, or ALK2 binding fragment thereof, of any one of E1 and E66-E90, wherein the heavy chain CDR3 includes or consists of the sequence DYGGLKFDY (SEQ ID NO:15).

E94. The isolated antibody, or ALK2 binding fragment thereof, of any one of E1 and E66-E90, wherein the heavy chain CDR3 includes or consists of the sequence GPTQAIHYFAY (SEQ ID NO:16).

E95. The isolated antibody, or ALK2 binding fragment thereof, of any one of E1 and E66-E90, wherein the heavy chain CDR3 includes or consists of the sequence AGFILGSLGVAWMDV (SEQ ID NO:17).

E96. The isolated antibody, or ALK2 binding fragment thereof, of E1, wherein the light chain CDR2 includes or consists of the sequence LVIYX$_1$DX$_2$X$_3$RPS (SEQ ID NO: 22, where X$_1$ is R, G, or Y, X$_2$ is S or N, and X$_3$ is N, D, or K).

E97. The isolated antibody, or ALK2 binding fragment thereof, of E96, wherein the light chain CDR2 includes or consists of the sequence SEQ ID NO: 22 and X$_1$ is R.

E98. The isolated antibody, or ALK2 binding fragment thereof, of E96, wherein the light chain CDR2 includes or consists of the sequence SEQ ID NO: 22 and X$_1$ is G.

E99. The isolated antibody, or ALK2 binding fragment thereof, of E96, wherein the light chain CDR2 includes or consists of the sequence SEQ ID NO: 22 and X$_1$ is Y.

E100. The isolated antibody, or ALK2 binding fragment thereof, of any one of E96-E99, wherein the light chain CDR2 includes or consists of the sequence SEQ ID NO: 22 and X$_2$ is S.

E101. The isolated antibody, or ALK2 binding fragment thereof, of any one of E96-E99, wherein the light chain CDR2 includes or consists of the sequence SEQ ID NO: 22 and X$_2$ is N.

E102. The isolated antibody, or ALK2 binding fragment thereof, of any one of E96-E101, wherein the light chain CDR2 includes or consists of the sequence SEQ ID NO: 22 and X$_3$ is N.

E103. The isolated antibody, or ALK2 binding fragment thereof, of any one of E96-E101, wherein the light chain CDR2 includes or consists of the sequence SEQ ID NO: 22 and X$_3$ is D.

E104. The isolated antibody, or ALK2 binding fragment thereof, of any one of E96-E101, wherein the light chain CDR2 includes or consists of the sequence SEQ ID NO: 22 and X$_3$ K.

E105. The isolated antibody, or ALK2 binding fragment thereof, of E1, wherein the light chain CDR2 includes or consists of the sequence LVIYRDSX$_1$RPS (SEQ ID NO: 23, where X$_1$ is N or K).

E106. The isolated antibody, or ALK2 binding fragment thereof, of E105, wherein the light chain CDR2 includes or consists of the sequence SEQ ID NO: 23 and X$_1$ is N.

E107. The isolated antibody, or ALK2 binding fragment thereof, of E105, wherein the light chain CDR2 includes or consists of the sequence SEQ ID NO: 23 and X$_1$ is K.

E108. The isolated antibody, or ALK2 binding fragment thereof, of E1, wherein the heavy chain CDR1 includes or consists of the sequence GFTFSSX$_1$AMX$_2$ (SEQ ID NO: 29, where X$_1$ is H or A, and X$_2$ is S or H).

E109. The isolated antibody, or ALK2 binding fragment thereof, of E108, wherein the heavy chain CDR1 includes or consists of the sequence SEQ ID NO: 29 and X$_1$ is H.

E110. The isolated antibody, or ALK2 binding fragment thereof, of E108, wherein the heavy chain CDR1 includes or consists of the sequence SEQ ID NO: 29 and X$_1$ is A.

E111. The isolated antibody, or ALK2 binding fragment thereof, of any one of E108-E110, wherein the heavy chain CDR1 includes or consists of the sequence SEQ ID NO: 29 and X$_2$ is S.

E112. The isolated antibody, or ALK2 binding fragment thereof, of any one of E108-E110, wherein the heavy chain CDR1 includes or consists of the sequence SEQ ID NO: 29 and X$_2$ is H.

E113. The isolated antibody, or ALK2 binding fragment thereof, of E1, wherein the heavy chain CDR1 includes or consists of the sequence GFTFX$_1$SX$_2$AMS (SEQ ID NO: 30, where X$_1$ is S or N, and X$_2$ is H or S).

E114. The isolated antibody, or ALK2 binding fragment thereof, of E113, wherein the heavy chain CDR1 includes or consists of the sequence SEQ ID NO: 30 and X$_1$ is S.

E115. The isolated antibody, or ALK2 binding fragment thereof, of E113, wherein the heavy chain CDR1 includes or consists of the sequence SEQ ID NO: 30 and X$_1$ is N.

E116. The isolated antibody, or ALK2 binding fragment thereof, of any one of E113-E115, wherein the heavy chain CDR1 includes or consists of the sequence SEQ ID NO: 30 and X$_2$ is H.

E117. The isolated antibody, or ALK2 binding fragment thereof, of any one of E113-E115, wherein the heavy chain CDR1 includes or consists of the sequence SEQ ID NO: 30 and X$_2$ is S.

E118. The isolated antibody, or ALK2 binding fragment thereof, of E1, wherein the light chain CDR1 includes or consists of the amino acid sequence SGSSSNIGSNYVS (SEQ ID NO: 1); the light chain CDR2 includes or consists of the amino acid sequence VLIYKNNHRPS (SEQ ID NO: 24); and the light chain CDR3 includes or consists of the amino acid sequence ASWDHSDRFYV (SEQ ID NO: 4).

E119. The isolated antibody, or ALK2 binding fragment thereof, of E1, wherein the heavy chain CDR1 includes or consists of the amino acid sequence GGTFSSYGVS (SEQ ID NO: 31); the heavy chain CDR2 includes or consists of the amino acid sequence WMGGIIPHFGIANYAQKFQG (SEQ ID NO: 36); and the heavy chain CDR3 includes or consists of the amino acid sequence EIGSLDI (SEQ ID NO: 13).

E120. The isolated antibody, or ALK2 binding fragment thereof, of E1, wherein the light chain CDR1 includes or consists of the amino acid sequence SGSSSNIGSNYVS (SEQ ID NO:1); the light chain CDR2 includes or consists of the amino acid sequence VLIYKNNHRPS (SEQ ID NO:24); the light chain CDR3 includes or consists of the amino acid sequence ASWDHSDRFYV (SEQ ID NO:4); the heavy chain CDR1 includes or consists of the amino acid sequence GGTFSSYGVS (SEQ ID NO:31); the heavy chain CDR2 includes or consists of the amino acid sequence WMGGIIPHFGIANYAQKFQG (SEQ ID NO:36); and the heavy chain CDR3 includes or consists of the amino acid sequence EIGSLDI (SEQ ID NO:13).

E121. The isolated antibody, or ALK2 binding fragment thereof, of E1, wherein the light chain CDR1 consists of the amino acid sequence SGSSSNIGSNYVS (SEQ ID NO:1); the light chain CDR2 consists of the amino acid sequence VLIYKNNHRPS (SEQ ID NO:24); the light chain CDR3 consists of the amino acid sequence ASWDHSDRFYV (SEQ ID NO:4); the heavy chain CDR1 consists of the amino acid sequence GGTFSSYGVS (SEQ ID NO:31); the heavy chain CDR2 consists of the amino acid sequence WMGGIIPHFGIANYAQKFQG (SEQ ID NO:36); and the heavy chain CDR3 consists of the amino acid sequence EIGSLDI (SEQ ID NO:13).

E122. The isolated antibody, or ALK2 binding fragment thereof, of E1, wherein the light chain CDR1 includes or consists of the amino acid sequence SGDSIPSFFAS (SEQ ID NO: 18); the light chain CDR2 includes or consists of the amino acid sequence LVIYRDSNRPS (SEQ ID NO: 25); and the light chain CDR3 includes or consists of the amino acid sequence YVTAPWKSIW (SEQ ID NO: 5).

E123. The isolated antibody, or ALK2 binding fragment thereof, of E1, wherein the heavy chain CDR1 includes or consists of the amino acid sequence GFTFSSHAMS (SEQ ID NO: 32); the heavy chain CDR2 includes or consists of the amino acid sequence WVGRIKSKADSGTTDYAAPVKG (SEQ ID NO: 37); and the heavy chain CDR3 includes or consists of the amino acid sequence DYGVAFAY (SEQ ID NO: 14).

E124. The isolated antibody, or ALK2 binding fragment thereof, of E1, wherein the light chain CDR1 includes or consists of the amino acid sequence SGDSIPSFFAS (SEQ ID NO:18); the light chain CDR2 includes or consists of the amino acid sequence LVIYRDSNRPS (SEQ ID NO:25); the light chain CDR3 includes or consists of the amino acid sequence YVTAPWKSIW (SEQ ID NO:5); the heavy chain CDR1 includes or consists of the amino acid sequence GFTFSSHAMS (SEQ ID NO:32); the heavy chain CDR2 includes or consists of the amino acid sequence WVGRIKSKADSGTTDYAAPVKG (SEQ ID NO:37); and the heavy chain CDR3 includes or consists of the amino acid sequence DYGVAFAY (SEQ ID NO:14).

E125. The isolated antibody, or ALK2 binding fragment thereof, of E1, wherein the light chain CDR1 consists of the amino acid sequence SGDSIPSFFAS (SEQ ID NO:18); the light chain CDR2 consists of the amino acid sequence LVIYRDSNRPS (SEQ ID NO:25); the light chain CDR3 consists of the amino acid sequence YVTAPWKSIW (SEQ ID NO:5); the heavy chain CDR1 consists of the amino acid sequence GFTFSSHAMS (SEQ ID NO:32); the heavy chain CDR2 consists of the amino acid sequence WVGRIKSKADSGTTDYAAPVKG (SEQ ID NO:37); and the heavy chain CDR3 consists of the amino acid sequence DYGVAFAY (SEQ ID NO:14).

E126. The isolated antibody, or ALK2 binding fragment thereof, of E1, wherein the light chain CDR1 includes or consists of the amino acid sequence SGDNIGTKYAY (SEQ ID NO: 19); the light chain CDR2 includes or consists of the amino acid sequence LVIYGDSDRPS (SEQ ID NO: 26); and the light chain CDR3 includes or consists of the amino acid sequence YSADAQQMKA (SEQ ID NO: 6).

E127. The isolated antibody, or ALK2 binding fragment thereof, of E1, wherein the heavy chain CDR1 includes or consists of the amino acid sequence GFTFNSSAMS (SEQ ID NO: 33); the heavy chain CDR2 includes or consists of the amino acid sequence WVGRIKSKRDGYTTDYAAPVKG (SEQ ID NO: 38); and the heavy chain CDR3 includes or consists of the amino acid sequence DYGGLKFDY (SEQ ID NO: 15).

E128. The isolated antibody, or ALK2 binding fragment thereof, of E1, wherein the light chain CDR1 includes or consists of the amino acid sequence SGDNIGTKYAY (SEQ ID NO:19); the light chain CDR2 includes or consists of the amino acid sequence LVIYGDSDRPS (SEQ ID NO:26); the light chain CDR3 includes or consists of the amino acid sequence YSADAQQMKA (SEQ ID NO:6); the heavy chain CDR1 includes or consists of the amino acid sequence GFTFNSSAMS (SEQ ID NO:33); the heavy chain CDR2 includes or consists of the amino acid sequence WVGRIKSKRDGYTTDYAAPVKG (SEQ ID NO:38); and the heavy chain CDR3 includes or consists of the amino acid sequence DYGGLKFDY (SEQ ID NO:15).

E129. The isolated antibody, or ALK2 binding fragment thereof, of E1, wherein the light chain CDR1 consists of the amino acid sequence SGDNIGTKYAY (SEQ ID NO:19); the light chain CDR2 consists of the amino acid sequence LVIYGDSDRPS (SEQ ID NO:26); the light chain CDR3 consists of the amino acid sequence YSADAQQMKA (SEQ ID NO:6); the heavy chain CDR1 consists of the amino acid sequence GFTFNSSAMS (SEQ ID NO:33); the heavy chain CDR2 consists of the amino acid sequence WVGRIKSKRDGYTTDYAAPVKG (SEQ ID NO:38); and the heavy chain CDR3 consists of the amino acid sequence DYGGLKFDY (SEQ ID NO:15).

E130. The isolated antibody, or ALK2 binding fragment thereof, of E1, wherein the light chain CDR1 includes or consists of the amino acid sequence SGDNLRKYSAH (SEQ ID NO: 20); the light chain CDR2 includes or consists of the amino acid sequence LVIYYDNKRPS (SEQ ID NO: 27); and the light chain CDR3 includes or consists of the amino acid sequence QVYASVHRM (SEQ ID NO: 7).

E131. The isolated antibody, or ALK2 binding fragment thereof, of E1, wherein the heavy chain CDR1 includes or consists of the amino acid sequence GGTFSSYAIH (SEQ ID NO: 34); the heavy chain CDR2 includes or consists of the amino acid sequence WMGRIIPDFGTANYAQKFQG (SEQ ID NO: 39); and the heavy chain CDR3 includes or consists of the amino acid sequence GPTQAIHYFAY (SEQ ID NO: 16).

E132. The isolated antibody, or ALK2 binding fragment thereof, of E1, wherein the light chain CDR1 includes or consists of the amino acid sequence SGDNLRKYSAH (SEQ ID NO:20); the light chain CDR2 includes or consists of the amino acid sequence LVIYYDNKRPS (SEQ ID NO:27); the light chain CDR3 includes or consists of the amino acid sequence QVYASVHRM (SEQ ID NO:7); the heavy chain CDR1 includes or consists of the amino acid sequence GGTFSSYAIH (SEQ ID NO:34); the heavy chain CDR2 includes or consists of the amino acid sequence WMGRIIPDFGTANYAQKFQG (SEQ ID NO:39); and the heavy chain CDR3 includes or consists of the amino acid sequence GPTQAIHYFAY (SEQ ID NO:16).

E133. The isolated antibody, or ALK2 binding fragment thereof, of E1, wherein the light chain CDR1 consists of the amino acid sequence SGDNLRKYSAH (SEQ ID NO:20); the light chain CDR2 consists of the amino acid sequence LVIYYDNKRPS (SEQ ID NO:27); the light chain CDR3 consists of the amino acid sequence QVYASVHRM (SEQ ID NO:7); the heavy chain CDR1 consists of the amino acid sequence GGTFSSYAIH (SEQ ID NO:34); the heavy chain CDR2 consists of the amino acid sequence WMGRIIPDFGTANYAQKFQG (SEQ ID NO:39); and the heavy chain CDR3 consists of the amino acid sequence GPTQAIHYFAY (SEQ ID NO:16).

E134. The isolated antibody, or ALK2 binding fragment thereof, of E1, wherein the light chain CDR1 includes or consists of the amino acid sequence SGDSLGSKSVH (SEQ ID NO: 21); the light chain CDR2 includes or consists of the amino acid sequence LVIYRDSKRPS (SEQ ID NO: 28); and the light chain CDR3 includes or consists of the amino acid sequence QTYDWSHFGW (SEQ ID NO: 8).

E135. The isolated antibody, or ALK2 binding fragment thereof, of E1, wherein the heavy chain CDR1 includes or consists of the amino acid sequence GFTFSSAAMH (SEQ ID NO: 35); the heavy chain CDR2 includes or consists of the amino acid sequence WVSVISSDGGSTYYADSVKG (SEQ ID NO: 12); and the heavy chain CDR3 includes or consists of the amino acid sequence AGFILGSLGVAWMDV (SEQ ID NO: 17).

E136. The isolated antibody, or ALK2 binding fragment thereof, of E1, wherein the light chain CDR1 includes or consists of the amino acid sequence SGDSLGSKSVH (SEQ ID NO:21); the light chain CDR2 includes or consists of the amino acid sequence LVIYRDSKRPS (SEQ ID NO:28); the light chain CDR3 includes or consists of the amino acid sequence QTYDWSHFGW (SEQ ID NO:8); the heavy chain CDR1 includes or consists of the amino acid sequence GFTFSSAAMH (SEQ ID NO:35); the heavy chain CDR2 includes or consists of the amino acid sequence WVSVISSDGGSTYYADSVKG (SEQ ID NO:12); and the heavy chain CDR3 includes or consists of the amino acid sequence AGFILGSLGVAWMDV (SEQ ID NO: 17).

E137. The isolated antibody, or ALK2 binding fragment thereof, of E1, wherein the light chain CDR1 consists of the amino acid sequence SGDSLGSKSVH (SEQ ID NO:21); the light chain CDR2 consists of the amino acid sequence LVIYRDSKRPS (SEQ ID NO:28); the light chain CDR3 consists of the amino acid sequence QTYDWSHFGW (SEQ ID NO:8); the heavy chain CDR1 consists of the amino acid sequence GFTFSSAAMH (SEQ ID NO:35); the heavy chain CDR2 consists of the amino acid sequence WVSVISSDGGSTYYADSVKG (SEQ ID NO:12); and the heavy chain CDR3 consists of the amino acid sequence AGFILGSLGVAWMDV (SEQ ID NO:17).

E138. The isolated antibody, or ALK2 binding fragment thereof, of E1, wherein the antibody, apart from the light chain CDR1, CDR2, and CDR3 and the heavy chain CDR1, CDR2, and CDR3, has at least 90% (e.g., 90%, 91%, 92%, 93%, 94%, 95%, 96%, 97%, 98%, 99% or more) sequence identity to amino acids 1 to 331 of the sequence of SEQ ID NO:67, or has at least 95% sequence identity to amino acids 1 to 331 of the sequence of SEQ ID NO:67, or has at least 98% sequence identity to amino acids 1 to 331 of the sequence of SEQ ID NO:67.

E139. The isolated antibody, or ALK2 binding fragment thereof, of E1, wherein the antibody, apart from the light chain CDR1, CDR2, and CDR3 and the heavy chain CDR1, CDR2, and CDR3, has at least 90% (e.g., 90%, 91%, 92%, 93%, 94%, 95%, 96%, 97%, 98%, 99% or more) sequence identity to amino acids 1 to 332 of the sequence of SEQ ID NO:68, or has at least 95% sequence identity to amino acids 1 to 332 of the sequence of SEQ ID NO:68, or has at least 98% sequence identity to amino acids 1 to 332 of the sequence of SEQ ID NO:68.

E140. The isolated antibody, or ALK2 binding fragment thereof, of E1, wherein the antibody, apart from the light chain CDR1, CDR2, and CDR3 and the heavy chain CDR1, CDR2, and CDR3, has at least 90% (e.g., 90%, 91%, 92%, 93%, 94%, 95%, 96%, 97%, 98%, 99% or more) sequence identity to amino acids 1 to 333 of the sequence of SEQ ID NO:69, or has at least 95% sequence identity to amino acids 1 to 333 of the sequence of SEQ ID NO:69, or has at least 98% sequence identity to amino acids 1 to 333 of the sequence of SEQ ID NO:69.

E141. The isolated antibody, or ALK2 binding fragment thereof, of E1, wherein the antibody, apart from the light chain CDR1, CDR2, and CDR3 and the heavy chain CDR1, CDR2, and CDR3, has at least 90% (e.g., 90%, 91%, 92%, 93%, 94%, 95%, 96%, 97%, 98%, 99% or more) sequence identity to amino acids 1 to 332 of the sequence of SEQ ID NO:70, or has at least 95% sequence identity to amino acids 1 to 332 of the sequence of SEQ ID NO:70, or has at least 98% sequence identity to amino acids 1 to 332 of the sequence of SEQ ID NO:70.

E142. The isolated antibody, or ALK2 binding fragment thereof, of E1, wherein the antibody, apart from the light chain CDR1, CDR2, and CDR3 and the heavy chain CDR1, CDR2, and CDR3, has at least 90% (e.g., 90%, 91%, 92%, 93%, 94%, 95%, 96%, 97%, 98%, 99% or more) sequence identity to amino acids 1 to 337 of the sequence of SEQ ID NO:71, or has at least 95% sequence identity to amino acids 1 to 337 of the sequence of SEQ ID NO:71, or has at least 98% sequence identity to amino acids 1 to 337 of the sequence of SEQ ID NO:71.

E143. The isolated antibody, or ALK2 binding fragment thereof, of E1, wherein the antibody includes or consists of amino acids 1 to 433 of the sequence of SEQ ID NO:67.

E144. The isolated antibody, or ALK2 binding fragment thereof, of E1, wherein the antibody includes or consists of amino acids 1 to 434 of the sequence of SEQ ID NO:68.

E145. The isolated antibody, or ALK2 binding fragment thereof, of E1, wherein the antibody includes or consists of amino acids 1 to 435 of the sequence of SEQ ID NO:69.

E146. The isolated antibody, or ALK2 binding fragment thereof, of E1, wherein the antibody includes or consists of amino acids 1 to 434 of the sequence of SEQ ID NO:70.

E147. The isolated antibody, or ALK2 binding fragment thereof, of E1, wherein the antibody includes or consists of amino acids 1 to 439 of the sequence of SEQ ID NO:71.

E148. An isolated antibody, or ALK2 binding fragment thereof, including (1) a light chain variable domain including a light chain complementarity determining region (CDR) 1 including or consisting of an amino acid sequence selected from RASQGISGNWLT (SEQ ID NO:40), SGDX$_1$X$_2$RX$_3$X$_4$X$_5$X$_6$H (SEQ ID NO: 64, where X$_1$ is N or A, X$_2$ is I or L, X$_3$ is K or Y, X$_4$ is K or Y, X$_5$ is Y or I, and X$_6$ is V or A), and SGSSSNIGQNYVS (SEQ ID NO:58); a light chain CDR2 including or consisting of the amino acid sequence LX$_1$IYX$_2$X$_3$X$_4$X$_5$X$_6$X$_7$S (SEQ ID NO:65, where X$_1$ is V or L, X$_2$ is D, R, or Y, X$_3$ is A, D, or N, X$_4$ is S or N, X$_5$ is K or N, X$_6$ is L or R, and X$_7$ is Q or P); and a light chain CDR3 including or consisting of an amino acid sequence selected from HQSYRGPM (SEQ ID NO:42), SSAGRDNY (SEQ ID NO:48), QSYGPGSV (SEQ ID NO:54), and SSWDLLSKSR (SEQ ID NO:60); and (2) a heavy chain variable domain including a heavy chain CDR1 including or consisting of the amino acid sequence GX$_1$TFX$_2$X$_3$X$_4$X$_5$X$_6$X$_7$ (SEQ ID NO:66, where X$_1$ is F or G, X$_2$ is G or S, X$_3$ is R, S, D, or T, X$_4$ is F, S, Y, or H, X$_5$ is V or A, and X$_6$ is M or I, and X$_7$ is H or S); a heavy chain CDR2 including or consisting of an amino acid sequence selected from WVSX$_1$IX$_2$YX$_3$X$_4$SX$_5$TYYADSVKG (SEQ ID NO:76, where X$_1$ is V or S, X$_2$ is G, H, or F, X$_3$ is S or D, X$_4$ is G or S, and X$_5$ is S, E, or N), and WMGLIQPRFGTANYAQKFQR (SEQ ID NO:62); and a heavy chain CDR3 including or consisting of an amino acid sequence selected from EPGYYYPSGYYRGPGYWMDV (SEQ ID NO:45), DRYFFDV (SEQ ID NO:51), PKSYASGPFAY (SEQ ID NO:57), and DYYGGMAY (SEQ ID NO:63).

E149. The isolated antibody, or ALK2 binding fragment thereof, of E148, wherein the light chain CDR1 includes or consists of the sequence of SEQ ID NO:64 and X$_1$ is N.

E150. The isolated antibody, or ALK2 binding fragment thereof, of E148, wherein the light chain CDR1 includes or consists of the sequence of SEQ ID NO:64 and X$_1$ is A.

E151. The isolated antibody, or ALK2 binding fragment thereof, of any one of E148-E150, wherein the light chain CDR1 includes or consists of the sequence of SEQ ID NO:64 and X$_2$ is I.

E152. The isolated antibody, or ALK2 binding fragment thereof, of any one of E148-E150, wherein the light chain CDR1 includes or consists of the sequence of SEQ ID NO:64 and X$_2$ is L.

E153. The isolated antibody, or ALK2 binding fragment thereof, of any one of E148-E152, wherein the light chain CDR1 includes or consists of the sequence of SEQ ID NO:64 and X$_3$ is K.

E154. The isolated antibody, or ALK2 binding fragment thereof, of any one of E148-E152, wherein the light chain CDR1 includes or consists of the sequence of SEQ ID NO:64 and X$_3$ is Y.

E155. The isolated antibody, or ALK2 binding fragment thereof, of any one of E148-E154, wherein the light chain CDR1 includes or consists of the sequence of SEQ ID NO:64 and X$_4$ is K.

E156. The isolated antibody, or ALK2 binding fragment thereof, of any one of E148-E154, wherein the light chain CDR1 includes or consists of the sequence of SEQ ID NO:64 and X$_4$ is Y.

E157. The isolated antibody, or ALK2 binding fragment thereof, of any one of E148-E156, wherein the light chain CDR1 includes or consists of the sequence of SEQ ID NO:64 and X$_5$ is Y.

E158. The isolated antibody, or ALK2 binding fragment thereof, of any one of E148-E156, wherein the light chain CDR1 includes or consists of the sequence of SEQ ID NO:64 and X$_5$ is I.

E159. The isolated antibody, or ALK2 binding fragment thereof, of any one of E148-E158, wherein the light chain CDR1 includes or consists of the sequence of SEQ ID NO:64 and X$_6$ is V.

E160. The isolated antibody, or ALK2 binding fragment thereof, of any one of E148-E158, wherein the light chain CDR1 includes or consists of the sequence of SEQ ID NO:64 and X$_6$ is A.

E161. The isolated antibody, or ALK2 binding fragment thereof, of any one of E148-E160, wherein the light chain CDR2 includes or consists of the sequence of SEQ ID NO:65 and X$_1$ is V.

E162. The isolated antibody, or ALK2 binding fragment thereof, of any one of E148-E160, wherein the light chain CDR2 includes or consists of the sequence of SEQ ID NO:65 and X$_1$ is L.

E163. The isolated antibody, or ALK2 binding fragment thereof, of any one of E148-E162, wherein the light chain CDR2 includes or consists of the sequence of SEQ ID NO:65 and X$_2$ is D.

E164. The isolated antibody, or ALK2 binding fragment thereof, of any one of E148-E162, wherein the light chain CDR2 includes or consists of the sequence of SEQ ID NO:65 and X$_2$ is R.

E165. The isolated antibody, or ALK2 binding fragment thereof, of any one of E148-E162, wherein the light chain CDR2 includes or consists of the sequence of SEQ ID NO:65 and X$_2$ is Y.

E166. The isolated antibody, or ALK2 binding fragment thereof, of any one of E148-E165, wherein the light chain CDR2 includes or consists of the sequence of SEQ ID NO:65 and X$_3$ is A.

E167. The isolated antibody, or ALK2 binding fragment thereof, of any one of E148-E165, wherein the light chain CDR2 includes or consists of the sequence of SEQ ID NO:65 and $X_3$ is D.

E168. The isolated antibody, or ALK2 binding fragment thereof, of any one of E148-E165, wherein the light chain CDR2 includes or consists of the sequence of SEQ ID NO:65 and $X_3$ is N.

E169. The isolated antibody, or ALK2 binding fragment thereof, of any one of E148-E168, wherein the light chain CDR2 includes or consists of the sequence of SEQ ID NO:65 and $X_4$ is S.

E170. The isolated antibody, or ALK2 binding fragment thereof, of any one of E148-E168, wherein the light chain CDR2 includes or consists of the sequence of SEQ ID NO:65 and $X_4$ is N.

E171. The isolated antibody, or ALK2 binding fragment thereof, of any one of E148-E170, wherein the light chain CDR2 includes or consists of the sequence of SEQ ID NO:65 and $X_5$ is K.

E172. The isolated antibody, or ALK2 binding fragment thereof, of any one of E148-E170, wherein the light chain CDR2 includes or consists of the sequence of SEQ ID NO:65 and $X_5$ is N.

E173. The isolated antibody, or ALK2 binding fragment thereof, of any one of E148-E172, wherein the light chain CDR2 includes or consists of the sequence of SEQ ID NO:65 and $X_6$ is L.

E174. The isolated antibody, or ALK2 binding fragment thereof, of any one of E148-E172, wherein the light chain CDR2 includes or consists of the sequence of SEQ ID NO:65 and $X_6$ is R.

E175. The isolated antibody, or ALK2 binding fragment thereof, of any one of E148-E174, wherein the light chain CDR2 includes or consists of the sequence of SEQ ID NO:65 and $X_7$ is Q.

E176. The isolated antibody, or ALK2 binding fragment thereof, of any one of E148-E174, wherein the light chain CDR2 includes or consists of the sequence of SEQ ID NO:65 and $X_7$ is P.

E177. The isolated antibody, or ALK2 binding fragment thereof, of any one of E148-E176, wherein the heavy chain CDR1 includes or consists of the sequence of SEQ ID NO:66 and $X_1$ is F.

E178. The isolated antibody, or ALK2 binding fragment thereof, of any one of E148-E176, wherein the heavy chain CDR1 includes or consists of the sequence of SEQ ID NO:66 and $X_1$ is G.

E179. The isolated antibody, or ALK2 binding fragment thereof, of any one of E148-E178, wherein the heavy chain CDR1 includes or consists of the sequence of SEQ ID NO:66 and $X_2$ is G.

E180. The isolated antibody, or ALK2 binding fragment thereof, of any one of E148-E178, wherein the heavy chain CDR1 includes or consists of the sequence of SEQ ID NO:66 and $X_2$ is S.

E181. The isolated antibody, or ALK2 binding fragment thereof, of any one of E148-E180, wherein the heavy chain CDR1 includes or consists of the sequence of SEQ ID NO:66 and $X_3$ is R.

E182. The isolated antibody, or ALK2 binding fragment thereof, of any one of E148-E180, wherein the heavy chain CDR1 includes or consists of the sequence of SEQ ID NO:66 and $X_3$ is S.

E183. The isolated antibody, or ALK2 binding fragment thereof, of any one of E148-E180, wherein the heavy chain CDR1 includes or consists of the sequence of SEQ ID NO:66 and $X_3$ is D.

E184. The isolated antibody, or ALK2 binding fragment thereof, of any one of E148-E180, wherein the heavy chain CDR1 includes or consists of the sequence of SEQ ID NO:66 and $X_3$ is T.

E185. The isolated antibody, or ALK2 binding fragment thereof, of any one of E148-E184, wherein the heavy chain CDR1 includes or consists of the sequence of SEQ ID NO:66 and $X_4$ is F.

E186. The isolated antibody, or ALK2 binding fragment thereof, of any one of E148-E184, wherein the heavy chain CDR1 includes or consists of the sequence of SEQ ID NO:66 and $X_4$ is S.

E187. The isolated antibody, or ALK2 binding fragment thereof, of any one of E148-E184, wherein the heavy chain CDR1 includes or consists of the sequence of SEQ ID NO:66 and $X_4$ is Y.

E188. The isolated antibody, or ALK2 binding fragment thereof, of any one of E148-E184, wherein the heavy chain CDR1 includes or consists of the sequence of SEQ ID NO:66 and $X_4$ is H.

E189. The isolated antibody, or ALK2 binding fragment thereof, of any one of E148-E188, wherein the heavy chain CDR1 includes or consists of the sequence of SEQ ID NO:66 and $X_5$ is V.

E190. The isolated antibody, or ALK2 binding fragment thereof, of any one of E148-E188, wherein the heavy chain CDR1 includes or consists of the sequence of SEQ ID NO:66 and $X_5$ is V or A.

E191. The isolated antibody, or ALK2 binding fragment thereof, of any one of E148-E190, wherein the heavy chain CDR1 includes or consists of the sequence of SEQ ID NO:66 and $X_6$ is M.

E192. The isolated antibody, or ALK2 binding fragment thereof, of any one of E148-E190, wherein the heavy chain CDR1 includes or consists of the sequence of SEQ ID NO:66 and $X_6$ is I.

E193. The isolated antibody, or ALK2 binding fragment thereof, of any one of E148-E192, wherein the heavy chain CDR1 includes or consists of the sequence of SEQ ID NO:66 and $X_7$ is H.

E194. The isolated antibody, or ALK2 binding fragment thereof, of any one of E148-E192, wherein the heavy chain CDR1 includes or consists of the sequence of SEQ ID NO:66 and $X_7$ is S.

E195. The isolated antibody, or ALK2 binding fragment thereof, of any one of E148-E194, wherein the heavy chain CDR2 includes or consists of the sequence of SEQ ID NO:76 and $X_1$ is V.

E196. The isolated antibody, or ALK2 binding fragment thereof, of any one of E148-E194, wherein the heavy chain CDR2 includes or consists of the sequence of SEQ ID NO:76 and $X_1$ is S.

E197. The isolated antibody, or ALK2 binding fragment thereof, of any one of E148-E196, wherein the heavy chain CDR2 includes or consists of the sequence of SEQ ID NO:76 and $X_2$ is G.

E198. The isolated antibody, or ALK2 binding fragment thereof, of any one of E148-E196, wherein the heavy chain CDR2 includes or consists of the sequence of SEQ ID NO:76 and $X_2$ is H.

E199. The isolated antibody, or ALK2 binding fragment thereof, of any one of E148-E196, wherein the heavy chain CDR2 includes or consists of the sequence of SEQ ID NO:76 and $X_2$ is F.

E200. The isolated antibody, or ALK2 binding fragment thereof, of any one of E148-E199, wherein the heavy chain CDR2 includes or consists of the sequence of SEQ ID NO:76 and $X_3$ is S.

E201. The isolated antibody, or ALK2 binding fragment thereof, of any one of E148-E199, wherein the heavy chain CDR2 includes or consists of the sequence of SEQ ID NO:76 and $X_3$ is D.

E202. The isolated antibody, or ALK2 binding fragment thereof, of any one of E148-E201, wherein the heavy chain CDR2 includes or consists of the sequence of SEQ ID NO:76 and $X_4$ is G.

E203. The isolated antibody, or ALK2 binding fragment thereof, of any one of E148-E201, wherein the heavy chain CDR2 includes or consists of the sequence of SEQ ID NO:76 and $X_4$ is S.

E204. The isolated antibody, or ALK2 binding fragment thereof, of any one of E148-E203, wherein the heavy chain CDR2 includes or consists of the sequence of SEQ ID NO:76 and $X_5$ is S.

E205. The isolated antibody, or ALK2 binding fragment thereof, of any one of E148-E203, wherein the heavy chain CDR2 includes or consists of the sequence of SEQ ID NO:76 and $X_5$ is E.

E206. The isolated antibody, or ALK2 binding fragment thereof, of any one of E148-E203, wherein the heavy chain CDR2 includes or consists of the sequence of SEQ ID NO:76 and $X_5$ is N.

E207. The isolated antibody, or ALK2 binding fragment thereof, of E148, wherein the light chain CDR1 includes or consists of the sequence RASQGISGNWLT (SEQ ID NO: 40).

E208. The isolated antibody, or ALK2 binding fragment thereof, of E148, wherein the light chain CDR1 includes or consists of the sequence SGDNIRKKYVH (SEQ ID NO: 46).

E209. The isolated antibody, or ALK2 binding fragment thereof, of E148, wherein the light chain CDR1 includes or consists of the sequence SGDALRYYIAH (SEQ ID NO: 52).

E210. The isolated antibody, or ALK2 binding fragment thereof, of E148, wherein the light chain CDR1 includes or consists of the sequence SGSSSNIGQNYVS (SEQ ID NO: 58).

E211. The isolated antibody, or ALK2 binding fragment thereof, of any one of E148 and E207-E210, wherein the light chain CDR2 includes or consists of the sequence LLIYDASNLQS (SEQ ID NO: 41).

E212. The isolated antibody, or ALK2 binding fragment thereof, of any one of E148 and E207-E210, wherein the light chain CDR2 includes or consists of the sequence LVIYRDSNRPS (SEQ ID NO: 47).

E213. The isolated antibody, or ALK2 binding fragment thereof, of any one of E148 and E207-E210, wherein the light chain CDR2 includes or consists of the sequence LVIYYNNNRPS (SEQ ID NO: 53).

E214. The isolated antibody, or ALK2 binding fragment thereof, of any one of E148 and E207-E210, wherein the light chain CDR2 includes or consists of the sequence LLIYDNSKRPS (SEQ ID NO: 59).

E215. The isolated antibody, or ALK2 binding fragment thereof, of any one of E148 and E207-E214, wherein the light chain CDR3 includes or consists of the sequence HQSYRGPM (SEQ ID NO: 42).

E216. The isolated antibody, or ALK2 binding fragment thereof, of any one of E148 and E207-E214, wherein the light chain CDR3 includes or consists of the sequence SSAGRDNY (SEQ ID NO: 48).

E217. The isolated antibody, or ALK2 binding fragment thereof, of any one of E148 and E207-E214, wherein the light chain CDR3 includes or consists of the sequence QSYGPGSV (SEQ ID NO: 54).

E218. The isolated antibody, or ALK2 binding fragment thereof, of any one of E148 and E207-E214, wherein the light chain CDR3 includes or consists of the sequence SSWDLLSKSR (SEQ ID NO: 60).

E219. The isolated antibody, or ALK2 binding fragment thereof, of any one of E148 and E207-E218, wherein the heavy chain CDR1 includes or consists of the sequence GFTFGRFVMH (SEQ ID NO: 43).

E220. The isolated antibody, or ALK2 binding fragment thereof, of any one of E148 and E207-E218, wherein the heavy chain CDR1 includes or consists of the sequence GFTFSSSAMH (SEQ ID NO: 49).

E221. The isolated antibody, or ALK2 binding fragment thereof, of any one of E148 and E207-E218, wherein the heavy chain CDR1 includes or consists of the sequence GFTFSDYAMH (SEQ ID NO: 55).

E222. The isolated antibody, or ALK2 binding fragment thereof, of any one of E148 and E207-E218, wherein the heavy chain CDR1 includes or consists of the sequence GGTFSTHAIS (SEQ ID NO: 61).

E223. The isolated antibody, or ALK2 binding fragment thereof, of any one of E148 and E207-E222, wherein the heavy chain CDR2 includes or consists of the sequence WVSVIGYSGSSTYYADSVKG (SEQ ID NO: 44).

E224. The isolated antibody, or ALK2 binding fragment thereof, of any one of E148 and E207-E222, wherein the heavy chain CDR2 includes or consists of the sequence WVSVIHYDSSETYYADSVKG (SEQ ID NO: 50).

E225. The isolated antibody, or ALK2 binding fragment thereof, of any one of E148 and E207-E222, wherein the heavy chain CDR2 includes or consists of the sequence WVSSIFYSGSNTYYADSVKG (SEQ ID NO: 56).

E226. The isolated antibody, or ALK2 binding fragment thereof, of any one of E148 and E207-E222, wherein the heavy chain CDR2 includes or consists of the sequence WMGLIQPRFGTANYAQKFQR (SEQ ID NO: 62).

E227. The isolated antibody, or ALK2 binding fragment thereof, of any one of E148 and E207-E226, wherein the heavy chain CDR3 includes or consists of the sequence EPGYYYPSGYYRGPGYWMDV (SEQ ID NO: 45).

E228. The isolated antibody, or ALK2 binding fragment thereof, of any one of E148 and E207-E226, wherein the heavy chain CDR3 includes or consists of the sequence DRYFFDV (SEQ ID NO: 51).

E229. The isolated antibody, or ALK2 binding fragment thereof, of any one of E148 and E207-E226, wherein the heavy chain CDR3 includes or consists of the sequence PKSYASGPFAY (SEQ ID NO: 57).

E230. The isolated antibody, or ALK2 binding fragment thereof, of any one of E148 and E207-E226, wherein the heavy chain CDR3 includes or consists of the sequence DYYGGMAY (SEQ ID NO: 63).

E231. The isolated antibody, or ALK2 binding fragment thereof, of E148, wherein the light chain CDR1 includes or consists of the amino acid sequence RASQGISGNWLT (SEQ ID NO: 40); the light chain CDR2 includes or consists of the amino acid sequence LLIYDASNLQS (SEQ ID NO:

41); and the light chain CDR3 includes or consists of the amino acid sequence HQSYRGPM (SEQ ID NO: 42).

E232. The isolated antibody, or ALK2 binding fragment thereof, of E148, wherein the heavy chain CDR1 includes or consists of the amino acid sequence GFTFGRFVMH (SEQ ID NO: 43); the heavy chain CDR2 includes or consists of the amino acid sequence WVSVIGYSGSSTYYADSVKG (SEQ ID NO: 44); and the heavy chain CDR3 includes or consists of the amino acid sequence EPGYYYPSGYYRGPGYWMDV (SEQ ID NO: 45).

E233. The isolated antibody, or ALK2 binding fragment thereof, of E148, wherein the light chain CDR1 includes or consists of the amino acid sequence RASQGISGNWLT (SEQ ID NO:40); the light chain CDR2 includes or consists of the amino acid sequence LLIYDASNLQS (SEQ ID NO:41); the light chain CDR3 includes or consists of the amino acid sequence HQSYRGPM (SEQ ID NO:42); the heavy chain CDR1 includes or consists of the amino acid sequence GFTFGRFVMH (SEQ ID NO:43); the heavy chain CDR2 includes or consists of the amino acid sequence WVSVIGYSGSSTYYADSVKG (SEQ ID NO:44); and the heavy chain CDR3 includes or consists of the amino acid sequence EPGYYYPSGYYRGPGYWMDV (SEQ ID NO:45).

E234. The isolated antibody, or ALK2 binding fragment thereof, of E148, wherein the light chain CDR1 consists of the amino acid sequence RASQGISGNWLT (SEQ ID NO:40); the light chain CDR2 consists of the amino acid sequence LLIYDASNLQS (SEQ ID NO:41); the light chain CDR3 consists of the amino acid sequence HQSYRGPM (SEQ ID NO:42); the heavy chain CDR1 consists of the amino acid sequence GFTFGRFVMH (SEQ ID NO:43); the heavy chain CDR2 consists of the amino acid sequence WVSVIGYSGSSTYYADSVKG (SEQ ID NO:44); and the heavy chain CDR3 consists of the amino acid sequence EPGYYYPSGYYRGPGYWMDV (SEQ ID NO:45).

E235. The isolated antibody, or ALK2 binding fragment thereof, of E148, wherein the light chain CDR1 includes or consists of the amino acid sequence SGDNIRKKYVH (SEQ ID NO: 46); the light chain CDR2 includes or consists of the amino acid sequence LVIYRDSNRPS (SEQ ID NO: 47); and the light chain CDR3 includes or consists of the amino acid sequence SSAGRDNY (SEQ ID NO: 48).

E236. The isolated antibody, or ALK2 binding fragment thereof, of E148, wherein the heavy chain CDR1 includes or consists of the amino acid sequence GFTFSSSAMH (SEQ ID NO: 49); the heavy chain CDR2 includes or consists of the amino acid sequence WVSVIHYDSSETYYADSVKG (SEQ ID NO: 50); and the heavy chain CDR3 includes or consists of the amino acid sequence DRYFFDV (SEQ ID NO: 51).

E237. The isolated antibody, or ALK2 binding fragment thereof, of E148, wherein the light chain CDR1 includes or consists of the amino acid sequence SGDNIRKKYVH (SEQ ID NO:46); the light chain CDR2 includes or consists of the amino acid sequence LVIYRDSNRPS (SEQ ID NO:47); the light chain CDR3 includes or consists of the amino acid sequence SSAGRDNY (SEQ ID NO:48); the heavy chain CDR1 includes or consists of the amino acid sequence GFTFSSSAMH (SEQ ID NO:49); the heavy chain CDR2 includes or consists of the amino acid sequence WVSVIHYDSSETYYADSVKG (SEQ ID NO:50); and the heavy chain CDR3 includes or consists of the amino acid sequence DRYFFDV (SEQ ID NO:51).

E238. The isolated antibody, or ALK2 binding fragment thereof, of E148, wherein the light chain CDR1 consists of the amino acid sequence SGDNIRKKYVH (SEQ ID NO:46); the light chain CDR2 consists of the amino acid sequence LVIYRDSNRPS (SEQ ID NO:47); the light chain CDR3 consists of the amino acid sequence SSAGRDNY (SEQ ID NO:48); the heavy chain CDR1 consists of the amino acid sequence GFTFSSSAMH (SEQ ID NO:49); the heavy chain CDR2 consists of the amino acid sequence WVSVIHYDSSETYYADSVKG (SEQ ID NO:50); and the heavy chain CDR3 consists of the amino acid sequence DRYFFDV (SEQ ID NO:51).

E239. The isolated antibody, or ALK2 binding fragment thereof, of E148, wherein the light chain CDR1 includes or consists of the amino acid sequence SGDALRYYIAH (SEQ ID NO: 52); the light chain CDR2 includes or consists of the amino acid sequence LVIYYNNNRPS (SEQ ID NO: 53); and the light chain CDR3 includes or consists of the amino acid sequence QSYGPGSV (SEQ ID NO: 54).

E240. The isolated antibody, or ALK2 binding fragment thereof, of E148, wherein the heavy chain CDR1 includes or consists of the amino acid sequence GFTFSDYAMH (SEQ ID NO: 55); the heavy chain CDR2 includes or consists of the amino acid sequence WVSSIFYSGSNTYYADSVKG (SEQ ID NO: 56); and the heavy chain CDR3 includes or consists of the amino acid sequence PKSYASGPFAY (SEQ ID NO: 57).

E241. The isolated antibody, or ALK2 binding fragment thereof, of E148, wherein the light chain CDR1 includes or consists of the amino acid sequence SGDALRYYIAH (SEQ ID NO:52); the light chain CDR2 includes or consists of the amino acid sequence LVIYYNNNRPS (SEQ ID NO:53); the light chain CDR3 includes or consists of the amino acid sequence QSYGPGSV (SEQ ID NO:54); the heavy chain CDR1 includes or consists of the amino acid sequence GFTFSDYAMH (SEQ ID NO:55); the heavy chain CDR2 includes or consists of the amino acid sequence WVSSIFYSGSNTYYADSVKG (SEQ ID NO:56); and the heavy chain CDR3 includes or consists of the amino acid sequence PKSYASGPFAY (SEQ ID NO:57).

E242. The isolated antibody, or ALK2 binding fragment thereof, of E148, wherein the light chain CDR1 consists of the amino acid sequence SGDALRYYIAH (SEQ ID NO:52); the light chain CDR2 consists of the amino acid sequence LVIYYNNNRPS (SEQ ID NO:53); the light chain CDR3 consists of the amino acid sequence QSYGPGSV (SEQ ID NO:54); the heavy chain CDR1 consists of the amino acid sequence GFTFSDYAMH (SEQ ID NO:55); the heavy chain CDR2 consists of the amino acid sequence WVSSIFYSGSNTYYADSVKG (SEQ ID NO:56); and the heavy chain CDR3 consists of the amino acid sequence PKSYASGPFAY (SEQ ID NO:57).

E243. The isolated antibody, or ALK2 binding fragment thereof, of E148, wherein the light chain CDR1 includes or consists of the amino acid sequence SGSSSNIGQNYVS (SEQ ID NO: 58); the light chain CDR2 includes or consists of the amino acid sequence LLIYDNSKRPS (SEQ ID NO: 59); and the light chain CDR3 includes or consists of the amino acid sequence SSWDLLSKSR (SEQ ID NO: 60).

E244. The isolated antibody, or ALK2 binding fragment thereof, of E148, wherein the heavy chain CDR1 includes or consists of the amino acid sequence GGTFSTHAIS (SEQ ID NO: 61); the heavy chain CDR2 includes or consists of the amino acid sequence WMGLIQPRFGTANYAQKFQR (SEQ ID NO: 62); and the heavy chain CDR3 includes or consists of the amino acid sequence DYYGGMAY (SEQ ID NO: 63).

E245. The isolated antibody, or ALK2 binding fragment thereof, of E148, wherein the light chain CDR1 includes or consists of the amino acid sequence SGSSSNIGQNYVS (SEQ ID NO:58); the light chain CDR2 includes or consists of the amino acid sequence LLIYDNSKRPS (SEQ ID NO:59); the light chain CDR3 includes or consists of the amino acid sequence SSWDLLSKSR (SEQ ID NO:60); the heavy chain CDR1 includes or consists of the amino acid sequence GGTFSTHAIS (SEQ ID NO:61); the heavy chain CDR2 includes or consists of the amino acid sequence WMGLIQPRFGTANYAQKFQR (SEQ ID NO:62); and the heavy chain CDR3 includes or consists of the amino acid sequence DYYGGMAY (SEQ ID NO: 63).

E246. The isolated antibody, or ALK2 binding fragment thereof, of E148, wherein the light chain CDR1 consists of the amino acid sequence SGSSSNIGQNYVS (SEQ ID NO:58); the light chain CDR2 consists of the amino acid sequence LLIYDNSKRPS (SEQ ID NO:59); the light chain CDR3 consists of the amino acid sequence SSWDLLSKSR (SEQ ID NO:60); the heavy chain CDR1 consists of the amino acid sequence GGTFSTHAIS (SEQ ID NO:61); the heavy chain CDR2 consists of the amino acid sequence WMGLIQPRFGTANYAQKFQR (SEQ ID NO:62); and the heavy chain CDR3 consists of the amino acid sequence DYYGGMAY (SEQ ID NO:63).

E247. The isolated antibody, or ALK2 binding fragment thereof, of E148, wherein the antibody, apart from the light chain CDR1, CDR2, and CDR3 and the heavy chain CDR1, CDR2, and CDR3, has at least 90% (e.g., 90%, 91%, 92%, 93%, 94%, 95%, 96%, 97%, 98%, 99%, or more) sequence identity to amino acids 1 to 344 of the sequence of SEQ ID NO:72, or has at least 95% sequence identity to amino acids 1 to 344 of the sequence of SEQ ID NO:72, or has at least 98% sequence identity to amino acids 1 to 344 of the sequence of SEQ ID NO:72.

E248. The isolated antibody, or ALK2 binding fragment thereof, of E148, wherein the antibody, apart from the light chain CDR1, CDR2, and CDR3 and the heavy chain CDR1, CDR2, and CDR3, has at least 90% (e.g., 90%, 91%, 92%, 93%, 94%, 95%, 96%, 97%, 98%, 99%, or more) sequence identity to amino acids 1 to 327 of the sequence of SEQ ID NO:73, or has at least 95% sequence identity to amino acids 1 to 327 of the sequence of SEQ ID NO:73, or has at least 98% sequence identity to amino acids 1 to 327 of the sequence of SEQ ID NO:73.

E249. The isolated antibody, or ALK2 binding fragment thereof, of E148, wherein the antibody, apart from the light chain CDR1, CDR2, and CDR3 and the heavy chain CDR1, CDR2, and CDR3, has at least 90% (e.g., 90%, 91%, 92%, 93%, 94%, 95%, 96%, 97%, 98%, 99%, or more) sequence identity to amino acids 1 to 331 of the sequence of SEQ ID NO:74, or has at least 95% sequence identity to amino acids 1 to 331 of the sequence of SEQ ID NO:74, or has at least 98% sequence identity to amino acids 1 to 331 of the sequence of SEQ ID NO:74.

E250. The isolated antibody, or ALK2 binding fragment thereof, of E148, wherein the antibody, apart from the light chain CDR1, CDR2, and CDR3 and the heavy chain CDR1, CDR2, and CDR3, has at least 90% (e.g., 90%, 91%, 92%, 93%, 94%, 95%, 96%, 97%, 98%, 99%, or more) sequence identity to amino acids 1 to 332 of the sequence of SEQ ID NO:75, or has at least 95% sequence identity to amino acids 1 to 332 of the sequence of SEQ ID NO:75, or has at least 98% sequence identity to amino acids 1 to 332 of the sequence of SEQ ID NO:75.

E251. The isolated antibody, or ALK2 binding fragment thereof, of E148, wherein the antibody includes or consists of amino acids 1 to 446 of the sequence of SEQ ID NO: 72.

E252. The isolated antibody, or ALK2 binding fragment thereof, of E148, wherein the antibody includes or consists of amino acids 1 to 429 of the sequence of SEQ ID NO: 73.

E253. The isolated antibody, or ALK2 binding fragment thereof, of E148, wherein the antibody includes or consists of amino acids 1 to 433 of the sequence of SEQ ID NO: 74.

E254. The isolated antibody, or ALK2 binding fragment thereof, of E148, wherein the antibody includes or consists of amino acids 1 to 434 of the sequence of SEQ ID NO: 75.

E255. The isolated antibody, or ALK2 binding fragment thereof, of any one of E1-E254, wherein the antibody is a monoclonal antibody.

E256. The isolated antibody, or ALK2 binding fragment thereof, of any one of E1-E255, wherein the antibody is a humanized antibody.

E257. The isolated antibody, or ALK2 binding fragment thereof, of any one of E1-E256, wherein the ALK2 binding fragment is a Fab.

E258. The isolated antibody, or ALK2 binding fragment thereof, of any one of E1-E256, wherein the ALK2 binding fragment is a Fab'.

E259. The isolated antibody, or ALK2 binding fragment thereof, of any one of E1-E256, wherein the ALK2 binding fragment is a F(ab')$_2$.

E260. The isolated antibody, or ALK2 binding fragment thereof, of any one of E1-E256, wherein the ALK2 binding fragment is a Fv.

E261. The isolated antibody, or ALK2 binding fragment thereof, of any one of E1-E260, wherein the antibody binds human ALK2 with a $K_D$ value of no more than 14 nM.

E262. The isolated antibody, or ALK2 binding fragment thereof, of any one of E1-E261, wherein the antibody binds human ALK2 with a $K_D$ value of no more than 5 nM.

E263. The isolated antibody, or ALK2 binding fragment thereof, of any one of E1-E262, wherein the antibody binds human ALK2 with a $K_D$ value of no more than 1 nM.

E264. The isolated antibody, or ALK2 binding fragment thereof, of any one of E1-E263, wherein the antibody binds human ALK2 with a $K_D$ value of no more than 0.5 nM.

E265. A nucleic acid molecule including a nucleotide sequence encoding the antibody or ALK2 binding fragment thereof of any one of E1-E264.

E266. An expression vector including the nucleic acid molecule of E265.

E267. A cell including the expression vector of E266.

E268. A pharmaceutical composition containing the antibody or ALK2 binding fragment thereof of any one of E1-E264, the nucleic acid molecule of E265, or the expression vector of E266 and one or more pharmaceutically acceptable carriers or excipients.

E269. The pharmaceutical composition of E268, wherein the antibody or ALK2 binding fragment thereof is in a therapeutically effective amount.

E270. A method of increasing bone mineral density in a subject in need thereof by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E271. A method of reducing bone resorption (e.g., bone loss) in a subject in need thereof by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E272. A method of increasing bone formation in a subject in need thereof by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E273. A method of increasing bone strength in a subject in need thereof by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E274. A method of reducing the risk of bone fracture in a subject in need thereof by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E275. The method of any one of E270-E274, wherein the subject has or is at risk of developing primary osteoporosis, secondary osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss.

E276. The method of E275, wherein the subject has or is at risk of developing primary osteoporosis.

E277. The method of E275, wherein the subject has or is at risk of developing secondary osteoporosis.

E278. The method of E275, wherein the subject has or is at risk of developing osteopenia.

E279. A method of treating a subject having or at risk of developing bone disease by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E280. The method of E279, wherein the bone disease is primary osteoporosis, secondary osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss.

E281. The method of E280, wherein the bone disease is primary osteoporosis.

E282. The method of E280, wherein the bone disease is secondary osteoporosis.

E283. The method of E280, wherein the bone disease is osteopenia.

E284. A method of treating a subject having or at risk of developing primary osteoporosis by administering to the subject the antibody or ALK2 binding fragment thereof of any one of E1 to E264, the nucleic acid molecule of E265, the expression vector of E266, or the pharmaceutical composition of E268 or E269.

E285. A method of treating a subject having or at risk of developing secondary osteoporosis by administering to the subject the antibody or ALK2 binding fragment thereof of any one of E1 to E264, the nucleic acid molecule of E265, the expression vector of E266, or the pharmaceutical composition of E268 or E269.

E286. A method of treating a subject having or at risk of developing osteopenia by administering to the subject the antibody or ALK2 binding fragment thereof of any one of E1 to E264, the nucleic acid molecule of E265, the expression vector of E266, or the pharmaceutical composition of E268 or E269.

E287. A method of treating a subject having or at risk of developing a bone fracture by administering to the subject the antibody or ALK2 binding fragment thereof of any one of E1 to E264, the nucleic acid molecule of E265, the expression vector of E266, or the pharmaceutical composition of E268 or E269.

E288. A method of treating a subject having or at risk of developing bone cancer or cancer metastasis-related bone loss by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E289. A method of treating a subject having or at risk of developing Paget's disease by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E290. A method of treating a subject having or at risk of developing renal osteodystrophy by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E291. A method of treating a subject having or at risk of developing treatment-related bone loss by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E292. A method of treating a subject having or at risk of developing diet-related bone loss by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E293. A method of treating a subject having or at risk of developing low gravity-related bone loss by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E294. A method of treating a subject having or at risk of developing immobility-related bone loss by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E295. The method of any one of E275, E276, E280, E281, and E284, the primary osteoporosis is age-related osteoporosis or hormone-related osteoporosis.

E296. The method of any one of E275, E278, E280, E282, and E285, wherein the secondary osteoporosis is immobilization-induced osteoporosis or glucocorticoid-induced osteoporosis.

E297. The method of any one of E275, E280, and E288, wherein the cancer is multiple myeloma.

E298. The method of any one of E275, E280, and E291, wherein the treatment is FGF-21 treatment, GLP-1 treatment, cancer therapy, or treatment for obesity or Type-2 diabetes.

E299. The method of any one of E275, E280, and E292, wherein the diet-related bone loss is rickets.

E300. The method of any one of E270-E299, wherein the subject is at risk of bone fracture.

E301. The method of any one of E270-E300, wherein the method increases bone formation in the subject.

E302. The method of any one of E270-E301, wherein the method decreases bone resorption (e.g., bone loss) in the subject.

E303. The method of any one of E270-E302, wherein the method increases osteoblast activity or osteoblastogenesis.

E304. The method of any one of E270-E303, wherein the method decreases osteoclast activity or decreases osteoclastogenesis.

E305. The method of any one of E270-E304, wherein the method decreases the risk of bone fracture.

E306. The method of any one of E270-E305, wherein the method increases bone mineral density.

E307. The method of any one of E270-E306, wherein the bone is cortical bone.

E308. The method of any one of E270-E306, wherein the bone is trabecular bone.

E309. The method of any one of E270-E308, wherein the method further includes evaluating the bone mineral density of the subject prior to administering the antibody or ALK2 binding fragment thereof, the nucleic acid molecule, the expression vector, or the pharmaceutical composition (e.g., evaluating bone mineral density using standard tests, such as dual-energy x-ray absorptiometry).

E310. The method of any one of E270-E309, wherein the method further includes evaluating the bone mineral density of the subject after administering the antibody or ALK2 binding fragment thereof, the nucleic acid molecule, the expression vector, or the pharmaceutical composition (e.g., evaluating bone mineral density using standard tests, such as dual-energy x-ray absorptiometry).

E311. A method of increasing red blood cell levels in a subject in need thereof by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E312. A method of increasing hemoglobin levels (e.g., serum hemoglobin levels) in a subject in need thereof by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E313. A method of increasing red blood cell count in a subject in need thereof by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E314. A method of promoting or increasing red blood cell formation in a subject in need thereof by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E315. A method of reducing hepcidin levels (e.g., serum hepcidin concentration) in a subject in need thereof by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E316. A method of increasing iron levels (e.g., serum iron levels) in a subject in need thereof by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E317. The method of any one of E311-E316, wherein the subject has or is at risk of developing anemia or blood loss.

E318. The method of E317, wherein the anemia or blood loss is associated with cancer, cancer treatment, renal disease or failure (e.g., chronic kidney disease or acute renal disease or failure), myelodysplastic syndrome, thalassemia, nutritional deficits, adverse reaction to medication, an inflammatory or autoimmune disease, splenomegaly, porphyria, vasculitis, hemolysis, bone marrow defects, bone marrow transplantation, diabetes, liver disease (e.g., acute liver disease or chronic liver disease), bleeding (e.g., acute or chronic bleeding), infection, hemoglobinopathy, drug use, alcohol abuse, advanced age, Churg-Strauss syndrome, Felty syndrome, graft versus host disease, hematopoietic stem cell transplantation, osteomyelofibrosis, pancytopenia, pure red-cell aplasia, purpura Schoenlein-Henoch, Shwachman syndrome (e.g., Shwachman-Diamond syndrome), contraindication to transfusion, surgery, trauma, a wound, an ulcer, urinary tract bleeding, digestive tract bleeding, frequent blood donation, or heavy menstrual bleeding.

E319. A method of treating a subject having or at risk of developing anemia by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E320. The method of E319, wherein In some embodiments, the anemia is associated with cancer, cancer treatment, renal disease or failure (e.g., chronic kidney disease or acute renal disease or failure), myelodysplastic syndrome, thalassemia, nutritional deficits, adverse reaction to medication, an inflammatory or autoimmune disease, splenomegaly, porphyria, vasculitis, hemolysis, bone marrow defects, bone marrow transplantation, diabetes, liver disease (e.g., acute liver disease or chronic liver disease), bleeding (e.g., acute or chronic bleeding), infection, hemoglobinopathy, drug use, alcohol abuse, advanced age, Churg-Strauss syndrome, Felty syndrome, graft versus host disease, hematopoietic stem cell transplantation, osteomyelofibrosis, pancytopenia, pure red-cell aplasia, purpura Schoenlein-Henoch, Shwachman syndrome (e.g., Shwachman-Diamond syndrome), contraindication to transfusion, surgery, trauma, a wound, an ulcer, urinary tract bleeding, digestive tract bleeding, frequent blood donation, or heavy menstrual bleeding.

E321. The method of E317-E320, wherein the anemia is aplastic anemia, iron deficiency anemia, vitamin deficiency anemia, anemia of inflammation (also called anemia of chronic disease, e.g., anemia caused by inflammatory diseases or conditions, such as infection (e.g., chronic infection, such as HIV/AIDS or tuberculosis), autoimmune disease (e.g., rheumatoid arthritis or lupus), cancer (e.g., cancer or cancer treatment), inflammatory bowel disease (e.g., Crohn's disease or ulcerative colitis), and chronic kidney disease), anemia associated with bone marrow disease, hemolytic anemia, sickle cell anemia, microcytic anemia, hypochromic anemia, sideroblastic anemia, Diamond Blackfan anemia, Fanconi's anemia, or refractory anemia with excess of blasts.

E322. The method of E321, wherein the anemia is IRIDA.

E323. The method of E322, wherein the anemia is anemia of inflammation.

E324. The method of any one of E311-E323, wherein the anemia is associated with elevated hepcidin levels.

E325. The method of any one of E311-E324, wherein the subject does not respond well to treatment with erythropoietin (EPO) or is susceptible to the adverse effects of EPO.

E326. The method of any one of E311-E325, wherein the method increases red blood cell formation, red blood cell count, hematocrit, or hemoglobin levels.

E327. The method of any one of E311-E326, wherein the method prevents or reduces elevated hepcidin levels.

E328. The method of any one of E311-E327, wherein the method increases iron levels.

E329. The method of any one of E311-E328, wherein the method reduces the subject's need for a blood transfusion.

E330. The method of any one of E311-E329, wherein the method further includes evaluating the red blood cell levels, hemoglobin levels, red blood cell count, hepcidin levels, or iron levels of the subject prior to administering the antibody or ALK2 binding fragment thereof, the nucleic acid molecule, the expression vector, or the pharmaceutical composition (e.g., evaluating blood cell levels, hemoglobin levels, red blood cell count, hepcidin levels, or iron levels using standard tests, such as a blood test).

E331. The method of any one of E311-E330, wherein the method further includes evaluating the red blood cell levels, hemoglobin levels, red blood cell count, hepcidin levels, or iron levels of the subject after administering the antibody or ALK2 binding fragment thereof, the nucleic acid molecule, the expression vector, or the pharmaceutical composition (e.g., evaluating blood cell levels, hemoglobin levels, red blood cell count, hepcidin levels, or iron levels using standard tests, such as a blood test).

E332. A method of preventing or reducing heterotopic ossification in a subject in need thereof by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E333. The method of E332, wherein the subject has fibrodysplasia ossificans progressiva (FOP).

E334. The method of E333, wherein the FOP is inherited FOP or sporadic FOP.

E335. A method of treating a subject having FOP by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E336. The method of E335, wherein the FOP is inherited FOP or sporadic FOP.

E337. The method of any one of E332-E336, wherein the method slows or inhibits the progression of FOP.

E338. The method of any one of E332-E337, wherein the method delays the onset of FOP (e.g., delays the onset of heterotopic ossification).

E339. The method of any one of E332-E338, wherein the method prevents heterotopic ossification (e.g., prevents heterotopic ossification in a subject at risk of developing heterotopic ossification, or prevents the recurrence of heterotopic ossification after surgical resection of ectopic bone).

E340. The method of any one of E332-E339, wherein the method reduces heterotopic ossification (e.g., reduces the amount of heterotopic ossification in a subject, reduces the occurrence of heterotopic ossification in a subject, or reduces the recurrence of heterotopic ossification after surgical resection of ectopic bone).

E341. The method of any one of E332-E340, wherein the method reduces the formation of heterotopic bone.

E342. The method of any one of E332-E341, wherein the method reduces the recurrence of heterotopic bone (e.g., after surgical resection).

E343. The method of any one of E332-E342, wherein the method further includes evaluating heterotopic ossification (e.g., the amount or location of ectopic bone) in the subject prior to administering the antibody or ALK2 binding fragment thereof, the nucleic acid molecule, the expression vector, or the pharmaceutical composition (e.g., evaluating heterotopic ossification using standard tests, such as radiographs (e.g., X-rays), CT (computed tomography), and/or MRI (magnetic resonance imaging)).

E344. The method of any one of E332-E343, wherein the method further includes evaluating heterotopic ossification (e.g., the amount or location of ectopic bone) in the subject after administering the antibody or ALK2 binding fragment thereof, the nucleic acid molecule, the expression vector, or the pharmaceutical composition (e.g., evaluating heterotopic ossification using standard tests, such as radiographs (e.g., X-rays), CT (computed tomography), and/or MRI (magnetic resonance imaging)).

E345. The method of any one of E332-E344, wherein the method further includes determining whether the subject carries an activating mutation in ALK2 (ACVR1) prior to administering the antibody or ALK2 binding fragment thereof, the nucleic acid molecule, the expression vector, or the pharmaceutical composition.

E346. A method of treating a subject having Sjogren's syndrome by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E347. The method of E346, wherein the method reduces or ameliorates a symptom of Sjogren's syndrome.

E348. The method of E347, wherein the symptom is dry eye, dry mouth, eye irritation, fibrosis of the lacrimal gland, inflammation of the lacrimal gland, blurred vision, systemic inflammation, joint pain, or fatigue.

E349. The method of E348, wherein the symptom is dry eye.

E350. A method of treating or reducing dry eye in a subject having Sjogren's syndrome (treating dry eye associated with Sjogren's syndrome) by administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E351. The method of any one of E346-E350, wherein the method increases the production of tears (e.g., increases tear volume production).

E352. The method of any one of E346-E351, wherein the method reduces eye irritation.

E353. The method of any one of E346-E352, wherein the method improves vision (e.g., increases visual acuity).

E354. The method of any one of E346-E353, wherein the method reduces fibrosis of the lacrimal gland.

E355. The method of any one of E346-E354, wherein the method reduces inflammation of the lacrimal gland.

E356. The method of any one of E346-E355, wherein the method increases the production of saliva or salivary flow.

E357. The method of any one of E346-E356, wherein the method reduces systemic inflammation.

E358. The method of any one of E346-E357, wherein the method reduces joint pain.

E359. The method of any one of E346-E358, wherein the method reduces fatigue.

E360. A method of treating a subject having multiple osteochondroma (MO), comprising administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E361. A method of preventing or reducing the formation of an osteochondroma in a subject having MO (e.g., preventing the formation of an osteochondroma in a subject with MO who has not yet developed an osteochondroma or reducing or preventing the formation of an osteochondroma in a subject with MO who has already developed one or more osteochondroma), comprising administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E362. A method of reducing the size of an osteochondroma in a subject having MO, comprising administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E363. A method of slowing or inhibiting the growth of an osteochondroma in a subject having MO, comprising administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E364. A method of reducing the number of osteochondromas in a subject having MO, comprising administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E365. The method of any one of E360-E364, wherein the osteochondroma is formed on a long bone.

E366. The method of any one of E360-E364, wherein the osteochondroma is formed on a flat bone.

E367. The method of any one of E360-E366, wherein the osteochondroma is formed on the growing end (metaphysis) of a bone.

E368. A method of treating a subject having diffuse intrinsic pontine glioma (DIPG), comprising administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E369. The method E368, wherein the method increases the survival time (e.g., extends the lifespan) of the subject.

E370. The method of E368 or E369, wherein the method reduces tumor growth.

E371. The method of any one of E368-E370, wherein the method reduces tumor volume.

E372. The method of any one of E368-E371, wherein the method reduces tumor metastasis.

E373. The method of any one of E368-E372, wherein the method further comprises determining whether the subject carries a mutation in ALK2 (ACVR1) prior to administering the antibody or ALK2 binding fragment thereof, the nucleic acid molecule, the expression vector, or the pharmaceutical composition.

E374. A method of reducing or preventing the development of posterior capsule opacification (PCO) in a subject in need thereof, comprising administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E375. A method of treating a subject having or at risk of developing PCO, comprising administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E376. The method of E374 or E375, wherein the subject has undergone or is soon to undergo cataract surgery (e.g., the subject is planning to undergo cataract surgery in 6 months, 5 months, 4 months, 3 months, 2 months, 1 month, 2 weeks, 1 week, or less).

E377. The method of any one of E374-E376, wherein the method improves visual acuity.

E378. The method of any one of E374-E377, wherein the method reduces light sensitivity or glare.

E379. The method of any one of E374-E378, wherein the method reduces or inhibits fibrosis (e.g., fibrosis on or near the posterior capsule, e.g., fibrosis near the implanted lens).

E380. The method of any one of E374-E379, wherein the method reduces or inhibits inflammation in the eye.

E381. A method of treating a subject having or at risk of developing cardiac hypertrophy, comprising administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E382. A method of slowing or preventing the development of cardiac hypertrophy, comprising administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E383. The method of E381 or E382, wherein the subject is identified as having hypertension or valvular disease.

E384. A method of treating a subject having or at risk of developing cardiac fibrosis, comprising administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E385. A method of slowing or preventing the development of cardiac fibrosis, comprising administering to the subject a therapeutically effective amount of the antibody or ALK2 binding fragment thereof of any one of E1 to E264, the nucleic acid molecule of E265, the expression vector of E266, or the pharmaceutical composition of E268 or E269.

E386. The method of E384 or E385, wherein the subject is identified as having hypertension, diabetic hypertrophic cardiomyopathy, or idiopathic dilated cardiomyopathy, or wherein the subject has had a myocardial infarction.

E387. The method of any one of E381-E386, wherein the method reduces or reverses cardiac fibrosis.

E388. The method of any one of E381-E387, wherein the method improves one or more symptom of cardiac hypertrophy or cardiac fibrosis.

E389. The method of E388, wherein the symptom of cardiac hypertrophy or cardiac fibrosis is reduced exercise capacity, reduced blood ejection volume, increased left ventricular end diastolic pressure, increased pulmonary capillary wedge pressure, reduced cardiac output, reduced cardiac index, increased pulmonary artery pressures, increased left ventricular end systolic and diastolic dimensions, increased left and right ventricular wall stress, increased wall tension and/or wall thickness, reduced myocardial contractility, increased cardiomyocyte area, or increased extracellular matrix deposition in the cardiac muscle.

E390. The method of any one of E270-E310, wherein the antibody or ALK2 binding fragment thereof, nucleic acid molecule, expression vector, or pharmaceutical composition is administered in an amount sufficient to increase bone mineral density, reduce bone resorption (e.g., reduce bone loss), reduce the risk of bone fracture, increase bone strength, reduce the rate of bone resorption (e.g., reduce the rate of bone loss), increase bone formation, increase the rate of bone formation, reduce osteoclast activity, increase osteoblast activity, or treat bone disease.

E391. The method of any one of E311-E331, wherein the antibody or ALK2 binding fragment thereof, nucleic acid molecule, expression vector, or pharmaceutical composition is administered in an amount sufficient to increase red blood cell levels, increase hemoglobin levels, increase red blood cell formation, increase red blood cell count, increase hematocrit, reduce the need for a blood transfusion, increase iron levels, decrease iron deficiency, decrease elevated hepcidin levels, or treat anemia.

E392. The method of any one of E332-E345, wherein the antibody or ALK2 binding fragment thereof, nucleic acid molecule, expression vector, or pharmaceutical composition is administered in an amount sufficient to treat FOP, slow or stop the progression of FOP, delay the onset of FOP, prevent heterotopic ossification, reduce heterotopic ossification, prevent or reduce heterotopic bone formation, or prevent or reduce the recurrence of heterotopic bone.

E393. The method of any one of E346-E359, wherein the antibody or ALK2 binding fragment thereof, nucleic acid molecule, expression vector, or pharmaceutical composition is administered in an amount sufficient to treat Sjogren's syndrome, treat or reduce dry eye associated with Sjogren's syndrome, reduce or ameliorate a symptom of Sjogren's syndrome, increase the production of tears, reduce eye irritation, improve vision, reduce fibrosis of the lacrimal gland, reduce inflammation of the lacrimal gland, or increase the production of saliva or salivary flow.

E394. The method of any one of E360-E367, wherein the antibody or ALK2 binding fragment thereof, nucleic acid molecule, expression vector, or pharmaceutical composition is administered in an amount sufficient to treat MO, prevent the formation of an osteochondroma, reduce the formation of an osteochondroma, reduce the size of an osteochondroma, reduce the growth of an osteochondroma, or reduce the number of osteochondromas.

E395. The method of any one of E368-E373, wherein the antibody or ALK2 binding fragment thereof, nucleic acid molecule, expression vector, or pharmaceutical composition is administered in an amount sufficient to treat DIPG, increase survival time (e.g., extend lifespan), reduce tumor growth, reduce tumor volume, or reduce tumor metastasis.

E396. The method of any one of E374-E380, wherein the antibody or ALK2 binding fragment thereof, nucleic acid molecule, expression vector, or pharmaceutical composition is administered in an amount sufficient to treat PCO, prevent the development of PCO, improve visual acuity, reduce light sensitivity or glare, reduce or inhibit fibrosis, or reduce or inhibit inflammation in the eye.

E397. The method of any one of E381-E3889 wherein the antibody or ALK2 binding fragment thereof, nucleic acid molecule, expression vector, or pharmaceutical composition is administered in an amount sufficient to treat cardiac hypertrophy, treat cardiac fibrosis, slow or prevent the development of cardiac hypertrophy, slow or prevent the development of cardiac fibrosis, or improve a symptom of cardiac fibrosis.

Definitions

As used herein, the term "about" refers to a value that is within 10% above or below the value being described.

As used herein, "administration" refers to providing or giving a subject a therapeutic agent (e.g., an ALK2 antibody or antigen binding fragment thereof (e.g., an ALK2 binding fragment) described herein), by any effective route. Exemplary routes of administration are described herein below.

The term "antibody" is used in the broadest sense and specifically covers intact monoclonal antibodies, polyclonal antibodies, multispecific antibodies (e.g., bispecific antibodies) formed from at least two intact antibodies, and antibody fragments so long as they exhibit the desired biological activity.

"Antibody fragments" include a portion of an intact antibody, preferably the antigen binding or variable region of the intact antibody. Examples of antibody fragments include Fab, Fab', F(ab')$_2$, and Fv fragments; diabodies; linear antibodies (Zapata et al. Protein Eng. 8(10):1057-1062 (1995)); single-chain antibody molecules; and multispecific antibodies formed from antibody fragments.

The term "monoclonal antibody" as used herein refers to an antibody obtained from a population of substantially homogeneous antibodies, i.e., the individual antibodies included in the population are identical except for possible naturally occurring mutations that may be present in minor amounts. Monoclonal antibodies are highly specific, being directed against a single antigenic site.

The term "monoclonal antibody" as used herein specifically includes "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)).

"Humanized" forms of non-human (e.g., murine) antibodies are chimeric antibodies, antibody chains or fragments thereof (such as Fv, Fab, Fab', F(ab')$_2$ or other antigen-binding subsequences of antibodies) which contain minimal sequence derived from non-human antibody. For the most part, humanized antibodies are human antibodies (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human antibody are replaced by corresponding non-human residues. Further, humanized antibodies may include residues which are found neither in the recipient antibody nor in the imported CDR or framework sequences.

As used herein, the terms "bone mineral density (BMD)," "bone density," and "bone mass" refer to a measure of the amount of bone mineral (e.g., calcium) in bone tissue. BMD may be measured by well-established clinical techniques known to one of skill in the art (e.g., by single-1 or dual-energy photon or X-ray absorptiometry (DEXA)). The concept of BMD relates to the mass of mineral per volume of bone, although clinically it is measured by proxy according to optical density per square centimeter of bone surface upon imaging. BMD measurement is used in clinical medicine as an indirect indicator of osteoporosis and fracture risk. In some embodiments, BMD test results are provided as a T-score, where the T-score represents the BMD of a subject compared to the ideal or peak bone mineral density of a healthy 30-year-old adult. A score of 0 indicates that the BMD is equal to the normal reference value for a healthy young adult. Differences between the measured BMD of subject and that of the reference value for a healthy young adult are measured in standard deviations units (SDs). Accordingly, a T-score of between +1 SD and −1 SD may indicate a normal BMD, a T-score of between −1 SD and −2.5 SD may indicate low bone mass (e.g., osteopenia), and a T-score lower than −2.5 SD may indicate osteoporosis or severe osteoporosis. In some embodiments, an ALK2 antibody or an antigen binding fragment thereof (e.g., an ALK2 binding fragment) of the invention is administered to a subject in need thereof, wherein the patient has low bone mass (e.g., a T-Score of between −1 SD and −2.5 SD). In some embodiments, an ALK2 antibody or an antigen binding fragment thereof (e.g., an ALK2 binding fragment) of the invention is administered to a subject in need thereof, wherein the patient has osteoporosis (e.g., a T-Score of less than −2.5 SD). In some embodiments, administration of an ALK2 antibody or an antigen binding fragment thereof (e.g., an ALK2 binding fragment) of the invention treats the subject by increasing their BMD (e.g., increasing the T-Score of the subject).

As used herein, the term "bone strength" refers to a measurement of bone that is determined by bone quality in addition to bone mineral density. Bone quality is influenced by bone geometry, microarchitecture, and the properties of constituent tissues. Bone strength can be used to assess the bone's risk of fracture.

As used herein, the term "bone disease" refers to a condition characterized by bone damage (e.g., decreased bone mineral density, decreased bone strength, and/or bone loss). Such diseases or conditions may be caused by an imbalance in osteoblast and/or osteoclast activity (e.g., increased bone resorption or reduced bone formation). Bone diseases include primary osteoporosis, secondary osteoporosis, osteopenia, osteopetrosis, bone fracture, bone cancer or cancer metastasis-related bone loss (e.g., bone loss associated with multiple myeloma), Paget's disease, renal osteodystrophy, treatment-related bone loss, diet-related bone loss, bone loss associated with the treatment of obesity, low gravity-related bone loss, and immobility-related bone loss.

As used herein, the terms "bone remodeling" or "bone metabolism" refer to the process for maintaining bone strength and ion homeostasis by replacing discrete parts of old bone with newly synthesized packets of proteinaceous matrix. Bone is resorbed by osteoclasts, and is deposited by osteoblasts in a process called ossification. Osteocyte activity plays a key role in this process. Conditions that result in a decrease in bone mass, can either be caused by an increase in resorption, or a decrease in ossification. In a healthy individual, during childhood, bone formation exceeds resorption. As the aging process occurs, resorption exceeds formation. Bone resorption rates are also typically much higher in post-menopausal older women due to estrogen deficiency related to menopause.

As used herein, the terms "bone resorption" or "bone catabolic activity" refer to a process by which osteoclasts break down the tissue in bones and release the minerals, resulting in a transfer of the mineral (e.g., calcium) from bone tissue to the blood. Increased rates of bone resorption are associated with aging, including in post-menopausal women. High rates of bone resorption, or rates of bone resorption that exceed the rate of ossification, are associated with bone disorders, such as decreased bone mineral density, including osteopenia and osteoporosis, and result in bone loss. In some embodiments, an ALK2 antibody or an antigen binding fragment thereof (e.g., an ALK2 binding fragment) of the invention is administered to a subject in need thereof to decrease bone resorption in the subject (e.g., the rate of bone resorption in the subject).

As used herein, the terms "bone formation," "ossification," "osteogenesis," or "bone anabolic activity" refer to the process of forming new bone tissue by osteoblasts. In some embodiments, an ALK2 antibody or an antigen binding fragment thereof (e.g., an ALK2 binding fragment) of the invention is administered to a subject in need thereof to increase bone formation (e.g., increase the rate of bone formation or osteogenesis in the subject).

As used herein, the term "cell type" refers to a group of cells sharing a phenotype that is statistically separable based on gene expression data. For instance, cells of a common cell type may share similar structural and/or functional characteristics, such as similar gene activation patterns and antigen presentation profiles. Cells of a common cell type may include those that are isolated from a common tissue (e.g., epithelial tissue, neural tissue, connective tissue, bone tissue, or muscle tissue) and/or those that are isolated from a common organ, tissue system, blood vessel, or other structure and/or region in an organism.

As used herein, the terms "conservative mutation," "conservative substitution," and "conservative amino acid substitution" refer to a substitution of one or more amino acids for one or more different amino acids that exhibit similar physicochemical properties, such as polarity, electrostatic charge, and steric volume. These properties are summarized for each of the twenty naturally-occurring amino acids in Table 1 below.

TABLE 1

Representative physicochemical properties of naturally-occurring amino acids

| Amino Acid | 3 Letter Code | 1 Letter Code | Side-chain Polarity | Electrostatic character at physiological pH (7.4) | Steric Volume[†] |
|---|---|---|---|---|---|
| Alanine | Ala | A | nonpolar | neutral | small |
| Arginine | Arg | R | polar | cationic | large |
| Asparagine | Asn | N | polar | neutral | intermediate |
| Aspartic acid | Asp | D | polar | anionic | intermediate |
| Cysteine | Cys | C | nonpolar | neutral | intermediate |
| Glutamic acid | Glu | E | polar | anionic | intermediate |
| Glutamine | Glr | Q | polar | neutral | intermediate |

TABLE 1-continued

Representative physicochemical properties of naturally-occurring amino acids

| Amino Acid | 3 Letter Code | 1 Letter Code | Side-chain Polarity | Electrostatic character at physiological pH (7.4) | Steric Volume[†] |
|---|---|---|---|---|---|
| Glycine | Gly | G | nonpolar | neutral | small |
| Histidine | His | H | polar | Both neutral and cationic forms in equilibrium at pH 7.4 | large |
| Isoleucine | Ile | I | nonpolar | neutral | large |
| Leucine | Leu | L | nonpolar | neutral | large |
| Lysine | Lys | K | polar | cationic | large |
| Methionine | Met | M | nonpolar | neutral | large |
| Phenylalanine | Phe | F | nonpolar | neutral | large |
| Proline | Pro | P | non-polar | neutral | intermediate |
| Serine | Ser | S | polar | neutral | small |
| Threonine | Thr | T | polar | neutral | intermediate |
| Tryptophan | Trp | W | nonpolar | neutral | bulky |
| Tyrosine | Tyr | Y | polar | neutral | large |
| Valine | Val | V | nonpolar | neutral | intermediate |

[†]based on volume in $Å^3$:
50-100 is small,
100-150 is intermediate,
150-200 is large, and
>200 is bulky From this table it is appreciated that the conservative amino acid families include (i) G, A, V, L and I; (ii) D and E; (iii) C, S and T; (iv) H, K and R; (v) N and Q; and (vi) F, Y and W. A conservative mutation or substitution is therefore one that substitutes one amino acid for a member of the same amino acid family (e.g., a substitution of Ser for Thr or Lys for Arg).

As used herein, the term an "isolated antibody" refers to an antibody that is substantially free of other antibodies having different antigenic specificities (e.g., an isolated antibody that binds to ALK2 is substantially free of contaminants, e.g., antibodies that do not bind to ALK2). In addition, an "isolated" antibody is one that has been identified and separated and/or recovered from a component of its natural environment. Contaminant components of its natural environment are materials that could interfere with diagnostic or therapeutic uses for the antibody, and may include enzymes, hormones, and other proteinaceous or non-proteinaceous solutes.

As used herein, the terms "increasing" and "decreasing" refer to modulating resulting in, respectively, greater or lesser amounts, of function, expression, or activity of a metric relative to a reference. For example, subsequent to administration of an ALK2 antibody or an antigen binding fragment thereof (e.g., an ALK2 binding fragment) of the invention in a method described herein, the amount of a marker of a metric (e.g., red blood cell levels, bone mineral density, tear production, survival time) as described herein may be increased in a subject relative to the amount of the marker prior to administration or relative to an untreated subject, or the amount of a marker of a metric (e.g., heterotopic ossification, or osteochondroma size, number, or formation) as described herein may be decreased in a subject relative to the amount of the marker prior to administration or relative to an untreated subject. Generally, the metric is measured subsequent to administration at a time that the administration has had the recited effect, e.g., at least one week, one month, 3 months, or 6 months, after a treatment regimen has begun.

As used herein, the terms "increase red blood cell levels" and "promote red blood cell formation" refer to clinically observable metrics, such as increases in hematocrit, red blood cell counts, and hemoglobin measurements, and are intended to be neutral as to the mechanism by which such changes occur. The term "low red blood cell levels" as used herein refers to red blood cell counts, hematocrit, and/or hemoglobin measurements that are below the range of values that is considered normal for the subject's age and gender. In some embodiments, an ALK2 antibody or an antigen binding fragment thereof (e.g., an ALK2 binding fragment) of the invention is administered to a subject (e.g., a subject having anemia) to increase red blood cell levels (e.g., increase hemoglobin levels or red blood cell counts).

As used herein, the terms "red blood cell formation" and "red blood cell production" refer to the generation of red blood cells, such as the process of erythropoiesis in which red blood cells are produced in the bone marrow.

As used herein, the term "anemia" refers to any abnormality in hemoglobin or red blood cells that leads to reduced oxygen levels in the blood. Anemia can be associated with abnormal production, processing, or performance of erythrocytes and/or hemoglobin. The term anemia refers to any reduction in the number of red blood cells and/or level of hemoglobin in blood relative to normal blood levels.

As used herein the term "anemia of inflammation" refers to a type of anemia driven by inflammatory cytokines and characterized by hypoferremia despite adequate iron stores, which is largely due to elevated hepcidin. Bone morphogenetic proteins (BMP) upregulate hepcidin by activating the SMAD signaling pathway through ALK2. Anemia of inflammation is also called anemia of chronic disease. Chronic conditions that cause anemia of inflammation include infection (e.g., chronic infection, such as HIV/AIDS or tuberculosis), autoimmune disease (e.g., rheumatoid arthritis or lupus), cancer (e.g., cancer or cancer treatment), inflammatory bowel disease (e.g., Crohn's disease or ulcerative colitis), and chronic kidney disease.

As used herein the terms "iron refractory iron deficiency anemia" and "IRIDA" refer to an inherited form of iron deficiency anemia. Key features of IRIDA include lifelong anemia (hemoglobin 6-9 g/dL); very low red blood cell size (microcytic), with a mean corpuscular volume (MCV) of 45-65 fL; very low iron levels in the blood (transferrin saturation <5%); abnormal oral iron absorption—no response to oral iron supplements or failure of an "oral iron challenge;" abnormal iron utilization—a slow, incomplete, and transient response to parenteral iron (iron injected intravenously); and other affected family members with an autosomal recessive inheritance pattern. A diagnosis of IRIDA can be confirmed by measuring the level of hepcidin in the blood. Mutations in TMPRSS6 have been found to be associated with IRIDA.

As used herein, the terms "heterotopic ossification," "heterotopic bone formation," and "ectopic bone formation" refer to the abnormal growth of bone in non-skeletal tissues, such as muscles, tendons, and other soft tissue. "Ectopic bone" refers to bone that has formed in non-skeletal tissues. Heterotopic ossification can occur in subjects with FOP.

As used herein, the terms "fibrodysplasia ossificans progressiva" and "FOP" refer to a disorder in which skeletal muscle and connective tissue, such as tendons and ligaments, are gradually replaced by bone (ossified). This condition leads to bone formation outside the skeleton (extra-skeletal or heterotopic bone) that restricts movement. This process generally becomes noticeable in early childhood, starting with the neck and shoulders and moving down the body and into the limbs. People with FOP are born with abnormal big toes (hallux valgus) which can be helpful in making the diagnosis. Trauma, such as a fall or invasive medical procedure, or a viral illness may trigger episodes of muscle swelling and inflammation (myositis). These flare-ups last for several days to months and often result in permanent bone growth in the injured area. FOP is caused by mutation of the ACVR1 gene and is inherited in an autosomal dominant manner.

As used herein, the term "fibrosis" refers to the pathological process of excess formation of fibrous connective tissue. Fibrosis is characterized by fibroblast accumulation and collagen deposition in excess of normal deposition in any particular tissue. In response to inflammation or an injury to a tissue, nearby fibroblasts can migrate into the wound, proliferate, and produce large amounts of collagenous extracellular matrix. When fibrosis occurs in response to injury, the term "scarring" can be used as synonym. Fibrosis may occur in many tissues of the body, including, e.g., lungs, skin, liver, kidney, heart, eye, lacrimal gland, tendon, cartilage, pancreatic tissue, uterine tissue, neural tissue, testis, ovary, adrenal gland, artery, vein, colon, small and large intestine, biliary tract, and gut.

As used herein, the term "cardiac hypertrophy" refers to the abnormal enlargement, or thickening, of the heart muscle resulting from a process in which adult cardiac myocytes respond to stress through hypertrophic growth. Such growth is characterized by cell size increases without cell division, assembling of additional sarcomeres within the cell to maximize force generation, and an activation of a fetal cardiac gene program. Cardiac hypertrophy is often associated with increased risk of morbidity and mortality, and has been found to be associated with fibrous tissue deposition in the cardiac interstitium accompanied by alterations in the extracellular matrix scaffold (e.g., cardiac fibrosis).

As used herein, the term "cardiac fibrosis," also known as myocardial fibrosis, refers to fibrosis of the myocardium and is characterized by wall stiffening, reduced contractility, and impaired overall heart performance. Cardiac myofibroblasts mediate fibrosis by the excessive deposition of connective tissue (e.g., extracellular matrix) in the interstitial space. Cardiac fibrosis is often found in association with cardiac hypertrophy.

As used herein, the term "dry eye" refers to a chronic condition that occurs when the eyes do not produce enough tears (e.g., reduced tear production or tear volume) or when the tears evaporate too quickly. Dry eye may be accompanied by eye discomfort and abnormal visual function.

The term "Sjogren's syndrome" as used herein refers to a systemic inflammatory disorder characterized by dry mouth, decreased tearing, and other dry mucous membranes. Dryness of the eyes and mouth are the most common symptoms of this syndrome.

As used herein, "dry eye associated with Sjogren's syndrome" refers to dry eye associated with primary Sjogren's syndrome and dry eye associated with secondary Sjogren's syndrome Dry eye associated with Sjogren's syndrome is generally classified as dry eye with reduced tear secretion.

As used herein, the term "multiple osteochondroma" or "MO" refers to a condition or disease associated with formation of osteochondromas on bones, e.g., at the ends of long bones or on flat bones. Subjects with MO often carry a loss-of-function mutation in an exostosin gene, e.g., EXT1 or EXT2. MO is also known as multiple hereditary exostoses, Bessel-Hagen disease, diaphyseal aclasis, multiple cartilaginous exostoses, multiple congenital exostosis, and hereditary multiple osteochondroma.

As used herein, the term "osteochondroma" refers to a benign (noncancerous) tumor that develops during childhood or adolescence. It is an abnormal overgrowth of cartilage and bone that typically forms on the surface of a bone near the growth plate. Osteochondromas most often form on the long bones of the leg and arm and on flat bones such as the pelvis and shoulder blade (scapula).

As used herein, the term "diffuse intrinsic pontine glioma" refers to a highly aggressive and difficult to treat brain tumor that originates in the pons and accounts for approximately 20% of all pediatric brain tumors. The median overall survival for children with diffuse intrinsic pontine glioma (DIPG) is 9-11 months, with one- and two-year survival rates of approximately 30% and less than 10%, respectively. DIPG has been found to be molecularly distinct from adult gliomas, and frequently harbors mutations in genes encoding histone variants. Mutations in ALK2 (ACVR1) have also been observed in DIPG.

As used herein, the term "posterior capsule opacification" refers to the most common postoperative complication of cataract surgery that occurs in 20% to 40% of patients. In posterior capsule opacification (PCO), the posterior capsule undergoes secondary opacification due to the migration, proliferation, and differentiation of lens epithelial cells. PCO can cause significant visual symptoms, particularly when it involves the central visual axis, and can be identified by the formation of fibrosis (e.g., scar tissue) on the posterior capsule (e.g., behind a lens implant). Symptoms of PCO include a gradual decrease of vision, blurred vision, sensitivity to sunlight, an observation of a glare or halo around lights.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity over the length of comparison, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. In certain embodiments, the present amino acid sequence identity is at least 80%, 90%, 95%, 98%, or 99%.

As used herein, the term "affinity" or "binding affinity" refers to the strength of the binding interaction between two molecules. Generally, binding affinity refers to the strength of the sum total of non-covalent interactions between a molecule and its binding partner, such as an ALK2 antibody or an antigen binding fragment thereof (e.g., an ALK2 binding fragment) and ALK2 protein. Unless indicated otherwise, binding affinity refers to intrinsic binding affinity, which reflects a 1:1 interaction between members of a binding pair. The binding affinity between two molecules is commonly described by the dissociation constant ($K_D$) or the affinity constant ($K_A$). Two molecules that have low binding affinity for each other generally bind slowly, tend to dissociate easily, and exhibit a large $K_D$. Two molecules that have high affinity for each other generally bind readily, tend to remain bound longer, and exhibit a small $K_D$. The $K_D$ of two interacting molecules may be determined using methods and techniques well known in the art, e.g., surface plasmon resonance. $K_D$ is calculated as the ratio of $k_{off}/k_{on}$.

As used herein, the term "specific binding" of an antibody or ALK2 binding fragment thereof (e.g., a Fab, Fab', F(ab')$_2$, or Fv fragment), is binding to a target molecule that is measurably different from binding to molecules that are not target molecules. As used herein, specific binding refers to a greater than 95% preference for binding a particular antigen versus background ("non-specific") binding. "Substantially specific" binding refers to a greater than about 80% preference for binding a particular antigen versus background. Binding can be measured using a variety of methods including, but not limited to, Western blot, immunoblot, enzyme-linked immunosorbant assay ("ELISA"), radioimmunoassay ("RIA"), immunoprecipitation, surface plasmon resonance, bio-layer interferometry, chemiluminescence, fluorescent polarization, phosphorescence, immunohistochemical analysis, matrix-assisted laser desorption/ionization time-of-flight ("MALDI-TOF") mass spectrometry, microcytometry, microarray, microscopy, fluorescence activated cell sorting ("FACS") and flow cytometry. In certain embodiments, an antibody that specifically binds to a target (e.g., ALK2) has a dissociation constant ($K_D$) no more than 0.1 nM, 0.15 nM, 0.2 nM, 0.3 nM, 0.5 nM, 0.7 nM, 1.0 nM, 2.0 nM, 4.0 nM, 5.0 nM, 7.0 nM, 10.0 nM, 14.0 nM or 15.0 nM.

As used herein, the term "polypeptide" describes a single polymer in which the monomers are amino acid residues which are covalently conjugated together through amide bonds. A polypeptide is intended to encompass any amino acid sequence, either naturally occurring, recombinant, or synthetically produced.

As used herein, the terms "effective amount," "therapeutically effective amount," and "sufficient amount" of a composition or ALK2 antibody or an antigen binding fragment thereof (e.g., an ALK2 binding fragment) described herein refer to a quantity sufficient to, when administered to the subject effect beneficial or desired results, including clinical results, and, as such, an "effective amount" or synonym thereto depends upon the context in which it is being applied. For example, in the context of treating patient having a or at risk of developing a disease, such as bone disease (e.g., osteoporosis, or a condition involving bone damage, e.g., primary osteoporosis, secondary osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss), a disease or condition involving low red blood cell levels (e.g., anemia or blood loss), heterotopic ossification (e.g., heterotopic ossification resulting from FOP), Sjogren's syndrome (e.g., dry eye associated with Sjogren's syndrome), DIPG, MO, PCO, or cardiac hypertrophy and/or fibrosis, it is an amount of the composition or ALK2 antibody or an antigen binding fragment thereof (e.g., an ALK2 binding fragment) sufficient to achieve a treatment response as compared to the response obtained without administration of the composition or ALK2 antibody or an antigen binding fragment thereof (e.g., an ALK2 binding fragment). The amount of a given composition described herein that will correspond to such an amount will vary depending upon various factors, such as the given agent, the pharmaceutical formulation, the route of administration, the type of disease or disorder, the identity of the subject (e.g. age, sex, weight) or host being treated, and the like, but can nevertheless be routinely determined by one skilled in the art by routine methods known in the art. Dosage regimen may be adjusted to provide the optimum therapeutic response.

As used herein, "locally" or "local administration" means administration at a particular site of the body intended for a local effect and not a systemic effect. Examples of local administration are epicutaneous, inhalational, intra-articular, intrathecal, intravaginal, intravitreal, intrauterine, intra-lesional administration, lymph node administration, intratumoral administration, and administration to a mucous membrane of the subject, wherein the administration is intended to have a local and not a systemic effect.

As used herein, the term "pharmaceutical composition" refers to a mixture containing a therapeutic agent, optionally in combination with one or more pharmaceutically acceptable excipients, diluents, and/or carriers, to be administered to a subject in order to prevent, treat or control a particular disease or condition affecting or that may affect the subject. The pharmaceutical composition may be in tablet or capsule form for oral administration or in aqueous form for intravenous or subcutaneous administration.

As used herein, the term "pharmaceutically acceptable carrier or excipient" refers to an excipient or diluent in a pharmaceutical composition. The pharmaceutically acceptable carrier must be compatible with the other ingredients of the formulation and suitable for contact with the tissues of a subject without excessive toxicity, irritation, allergic response, and other problem complications commensurate with a reasonable benefit/risk ratio. In the present invention, the pharmaceutically acceptable carrier or excipient must provide adequate pharmaceutical stability to the ALK2 antibody or an antigen binding fragment thereof (e.g., an ALK2 binding fragment) of the invention. The nature of the carrier or excipient differs with the mode of administration. For example, for intravenous administration, an aqueous solution carrier is generally used; for oral administration, a solid carrier is preferred.

As used herein, the term "sample" refers to a specimen (e.g., blood, blood component (e.g., serum or plasma), urine, saliva, amniotic fluid, cerebrospinal fluid, tissue (e.g., neural tissue, placental tissue, or dermal tissue), pancreatic fluid, chorionic villus sample, and cells (e.g., blood cells or bone cells)) isolated from a subject.

As used herein, "treatment" and "treating" in reference to a disease or condition, refer to an approach for obtaining beneficial or desired results, e.g., clinical results. Beneficial or desired results can include, but are not limited to, alleviation or amelioration of one or more symptoms or conditions; diminishment of extent of disease or condition; stabilized (i.e., not worsening) state of disease, disorder, or condition; preventing spread of disease or condition; delay or slowing the progress of the disease or condition; amelioration or palliation of the disease or condition; and remission (whether partial or total), whether detectable or undetectable. "Ameliorating" or "palliating" a disease or condition means that the extent and/or undesirable clinical manifestations of the disease, disorder, or condition are lessened and/or time course of the progression is slowed or lengthened, as compared to the extent or time course in the absence of treatment. "Treatment" can also mean prolonging survival as compared to expected survival if not receiving treatment. Those in need of treatment include those already with the condition or disorder, as well as those prone to have the condition or disorder or those in which the condition or disorder is to be prevented.

As used herein, the terms "subject" and "patient" refer to a mammal, e.g., a human. Mammals include, but are not limited to, humans and domestic and farm animals, such as monkeys (e.g., a cynomolgus monkey), mice, dogs, cats, horses, and cows, etc. A subject to be treated according to the methods described herein may be one who has been diagnosed with bone disease (e.g., a disease or condition involving bone damage, e.g., osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss), a disease involving low blood cell levels (e.g., anemia or blood loss), heterotopic ossification (e.g., heterotopic ossification resulting from FOP), Sjogren's syndrome (e.g., dry eye associated with Sjogren's syndrome), DIPG, MO, PCO, or cardiac hypertrophy and/or fibrosis or one at risk of developing these conditions. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

DESCRIPTION OF THE DRAWINGS

FIGS. 1A-1B are a series of graphs showing BMP6 inhibition dose response curves of Anti-ALK2 fABs performed on C2C12 cells with a SMAD1 luciferase reporter. Fifty percent inhibition values (IC50) for both a three and four parameter curve fit in Graphpad Prism are shown next to each graph. FIG. 1A is a graph of the dose response curves from first four fABs generated. FIG. 1B is a graph of the dose response curves from five second round fABs generated from Rapid Pool Maturation.

FIG. 2 is a graph showing the effect of treatment with an ALK2 antibody on hemoglobin levels in a mouse model of IRIDA. Treatment with an ALK2 antibody prevents the hemoglobin reduction associated with TMPRSS6 deficiency (*=p≤0.05; **=p≤0.01).

FIG. 5 shows the amino acid sequence of Antibody 1 (SEQ ID NO: 67), with the light chain and heavy chain CDR1, CDR2, and CDR3 domains highlighted and amino acid positions provided. The beginning and ending amino acid for the variable light chain, constant light chain, variable heavy chain, CH1 domain, EcoRI linker, Flag tag, tag linker, and the six amino acid histidine tag are also provided.

FIG. 6 shows the amino acid sequence of Antibody 2 (SEQ ID NO: 68), with the light chain and heavy chain CDR1, CDR2, and CDR3 domains highlighted and amino acid positions provided. The beginning and ending amino acid for the variable light chain, constant light chain, variable heavy chain, CH1 domain, EcoRI linker, Flag tag, tag linker, and the six amino acid histidine tag are also provided.

FIG. 7 shows the amino acid sequence of Antibody 3 (SEQ ID NO: 69), with the light chain and heavy chain CDR1, CDR2, and CDR3 domains highlighted and amino acid positions provided. The beginning and ending amino acid for the variable light chain, constant light chain, variable heavy chain, CH1 domain, EcoRI linker, Flag tag, tag linker, and the six amino acid histidine tag are also provided.

FIG. 8 shows the amino acid sequence of Antibody 4 (SEQ ID NO: 70), with the light chain and heavy chain CDR1, CDR2, and CDR3 domains highlighted and amino acid positions provided. The beginning and ending amino acid for the variable light chain, constant light chain, variable heavy chain, CH1 domain, EcoRI linker, Flag tag, tag linker, and the six amino acid histidine tag are also provided.

FIG. 9 shows the amino acid sequence of Antibody 5 (SEQ ID NO: 71), with the light chain and heavy chain CDR1, CDR2, and CDR3 domains highlighted and amino acid positions provided. The beginning and ending amino acid for the variable light chain, constant light chain, variable heavy chain, CH1 domain, EcoRI linker, Flag tag, tag linker, and the six amino acid histidine tag are also provided.

FIG. 10 shows the amino acid sequence of Antibody 6 (SEQ ID NO: 72), with the light chain and heavy chain CDR1, CDR2, and CDR3 domains highlighted and amino acid positions provided. The beginning and ending amino acid for the variable light chain, constant light chain, variable heavy chain, CH1 domain, EcoRI linker, Flag tag, tag linker, and the six amino acid histidine tag are also provided.

FIG. 11 shows the amino acid sequence of Antibody 7 (SEQ ID NO: 73), with the light chain and heavy chain CDR1, CDR2, and CDR3 domains highlighted and amino acid positions provided. The beginning and ending amino acid for the variable light chain, constant light chain, variable heavy chain, CH1 domain, EcoRI linker, Flag tag, tag linker, and the six amino acid histidine tag are also provided.

FIG. 12 shows the amino acid sequence of Antibody 8 (SEQ ID NO: 74), with the light chain and heavy chain CDR1, CDR2, and CDR3 domains highlighted and amino acid positions provided. The beginning and ending amino acid for variable light chain, constant light chain, variable heavy chain, CH1 domain, EcoRI linker, Flag tag, tag linker, and the six amino acid histidine tag are also provided.

FIG. 13 shows the amino acid sequence of Antibody 9 (SEQ ID NO: 75), with the light chain and heavy chain CDR1, CDR2, and CDR3 domains highlighted and amino acid positions provided. The beginning and ending amino acid for the variable light chain, constant light chain, variable heavy chain, CH1 domain, EcoRI linker, Flag tag, tag linker, and the six amino acid histidine tag are also provided.

DETAILED DESCRIPTION OF THE INVENTION

Figure 1A:
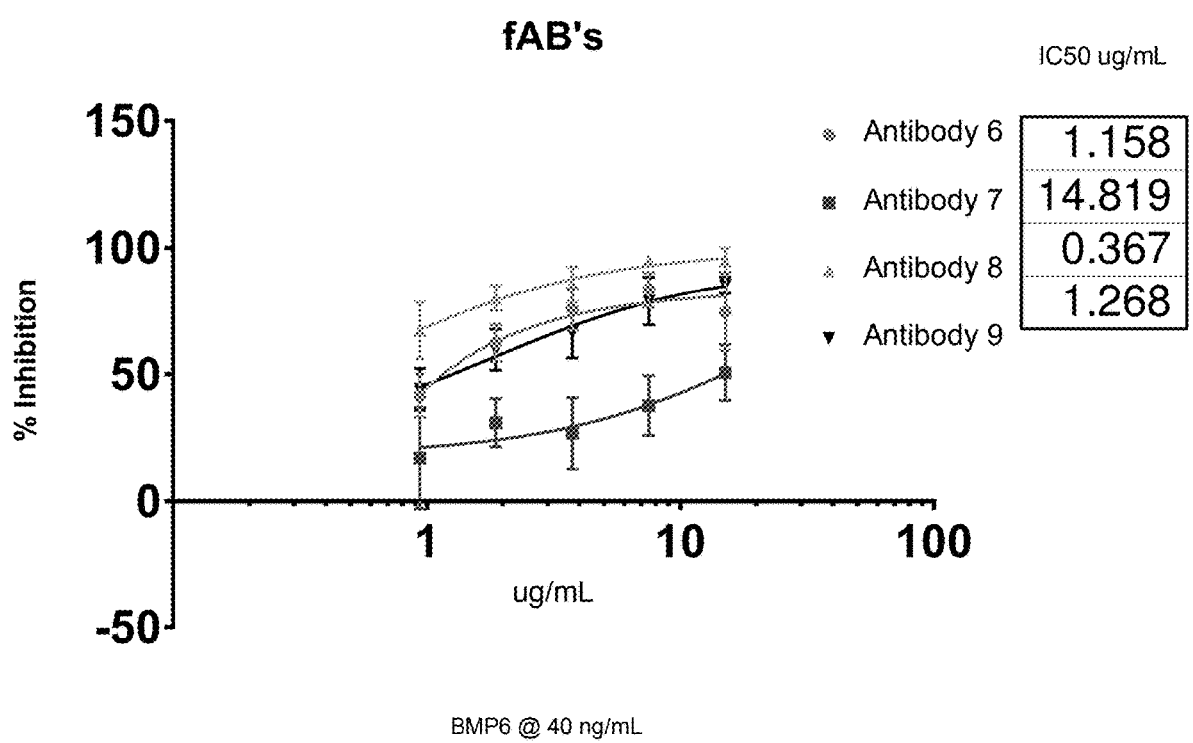

Described herein are compositions and methods for treating bone disease, anemia, heterotopic ossification (e.g., heterotopic ossification resulting from FOP), Sjogren's syndrome (e.g., dry eye associated with Sjogren's syndrome), DIPG, MO, PCO, or cardiac hypertrophy and/or cardiac fibrosis. The invention features ALK2 antibodies (e.g., neutralizing antibodies) and antigen binding fragments thereof (e.g., ALK2 binding fragments), as well as nucleic acid molecules containing a nucleotide sequence encoding an antibody or ALK2 binding fragment thereof, and expression vectors including a nucleic acid molecule containing a nucleotide sequence encoding the antibody or ALK2 binding fragment thereof. The invention also features methods of treating or preventing bone disease (e.g., a disease or condition involving bone damage, such as primary osteoporosis, secondary osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss), low red blood cell levels (e.g., low hemoglobin levels or low red blood cell count, e.g., anemia), heterotopic ossification (e.g., heterotopic ossification resulting from FOP), Sjogren's syndrome (e.g., dry eye associated with Sjogren's syndrome), DIPG, MO, PCO, or cardiac hypertrophy and/or cardiac fibrosis in a subject, such as a human subject, using the ALK2 antibodies or antigen binding fragments thereof, nucleic acid molecules, expression vectors, and compositions described herein.

ALK2 Antibodies

ALK2 (also known as ACVR1) is a bone morphogenetic protein (BMP) receptor in the transforming growth factor β (TGF-β) superfamily. ALK2 is widely expressed in many tissues during embryonic development and highly expressed in bones during postnatal development, and is thought to have an essential role in both osteogenesis and chondrogenesis. Gain of function mutations in ALK2, including c.617G>A (p.R206H), c.619C>G (p.Q207E), c.1067G>A (p.G356D), c.982G>T (p.G328W), c.983G>A (p.G328E), c.982G>A (p.G328R), c.774G>C/c.774G>T (P.R258S), c.1124G>C (p.R375P), c.587T>C (p.L196P), c.590-592delCTT (p.P197_F198delinsL), and c.605G>T (p.R202I), have been found in subjects with FOP, and studies using Alk2$^{R206H}$ mutant mice suggest that ALK2 regulates the osteogenic differentiation of mesenchymal stem cells. Activating mutations in ALK2 have also been observed in approximately 25% of DIPG patients and small molecule ALK2 inhibitors have been found to extend survival and reduce cellularity in orthotopic DIPG xenograft models. ALK2 may also play a role in anemia, as BMP activation of the SMAD signaling pathway through ALK2 induces the upregulation of hepcidin, a master regulator of iron homeostasis that is implicated in anemia of inflammation (also known as anemia of chronic disease) and iron refractory iron deficiency anemia (IRIDA). ALK2 also promotes the proliferation of lens epithelial cells during development; therefore, inhibition of ALK2 may prevent or reduce the aberrant proliferation of lens epithelial cells that leads to PCO. In addition, small molecule ALK2 inhibitors have been found to decrease inflammation and treat symptoms of Sjogren's syndrome in an established mouse model, and to reduce osteochondroma formation, growth, and size in multiple studies using mouse models of MO. Furthermore, both treatment with a small molecule ALK2 inhibitor and cardiomyocyte-specific deletion of ALK2 mitigated cardiac hypertrophy and left ventricular fibrosis in mice. Moreover, the effect of ALK2 ligands in promoting fibrosis suggests that inhibiting ALK2 can be used to treat diseases or conditions in which fibrosis contributes to the pathology (e.g., fibrosis of the posterior capsule in PCO, fibrosis of the lacrimal gland in Sjogren's syndrome, and fibrosis in cardiac fibrosis and/or cardiac hypertrophy).

The present invention is based, in part, on the discovery that an ALK2 antibody described herein restored hemoglobin levels, hepcidin concentration, and iron levels in a mouse model of IRIDA and increased bone density (e.g., reduced bone loss) in a mouse model of osteoporosis. Without wishing to be bound by theory, the finding that an ALK2 antibody restored hemoglobin levels in the TMPRSS6 knock down model of IRIDA suggests that the ALK2 antibodies described herein can be used to treat anemia of inflammation, as TMPRSS6 acts to suppress hepcidin secretion and anemia of inflammation often features elevated hepcidin levels. Given the gain of function mutations in ALK2 that have been identified in patients with FOP and DIPG, the ALK2 antibodies or antigen binding fragments thereof described herein may also be used for FOP treatment and/or for preventing or treating heterotopic ossification and for treating DIPG or extending survival of a subject having DIPG. Previous studies have also indicated that small molecule ALK2 inhibitors can be used to treat symptoms of Sjogren's syndrome, MO (e.g., reduce the formation, growth, or size of osteochondromas), and cardiac hypertrophy and cardiac fibrosis, accordingly, the ALK2 antibodies or antigen binding fragments thereof described herein may also be used to treat these conditions. Finally, the necessity of ALK2 for promoting lens epithelial cell proliferation suggests that ALK2 inhibition may be effective to treat PCO. Thus, the ALK2 antibodies or antigen binding fragments thereof), nucleic acid molecules, expression vectors, and compositions described herein can be administered to a subject, such as a human subject, to treat or prevent bone disease (e.g., a disease or condition involving bone damage, such as primary osteoporosis, secondary osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss), anemia (e.g., IRIDA, anemia of inflammation), heterotopic ossification (e.g., heterotopic ossification resulting from FOP), Sjogren's syndrome (e.g., dry eye associated with Sjogren's syndrome), DIPG, MO, PCO, or cardiac hypertrophy and/or cardiac fibrosis.

Vectors, Host Cells, and Protein Production

The ALK2 antibodies and antigen binding fragments thereof (e.g., ALK2 binding fragments) described herein can be produced from a host cell. A host cell refers to a vehicle that includes the necessary cellular components, e.g., organelles, needed to express the antibodies and antigen binding fragments thereof described herein from their corresponding nucleic acids. The nucleic acids may be included in nucleic acid vectors that can be introduced into the host cell by conventional techniques known in the art (e.g., transformation, transfection, electroporation, calcium phosphate precipitation, direct microinjection, infection, or the like). The choice of nucleic acid vectors depends in part on the host cells to be used. Generally, preferred host cells are of either eukaryotic (e.g., mammalian) or prokaryotic (e.g., bacterial) origin.

Nucleic Acid Vector Construction and Host Cells

A nucleic acid sequence encoding the amino acid sequence of an ALK2 antibody or antigen binding fragment thereof (e.g., an ALK2 binding fragment) described herein may be prepared by a variety of methods known in the art. These methods include, but are not limited to, oligonucleotide-mediated (or site-directed) mutagenesis and PCR mutagenesis. A nucleic acid molecule encoding an ALK2 antibody or antigen binding fragment thereof described herein may be obtained using standard techniques, e.g., gene synthesis. Alternatively, a nucleic acid molecule encoding an ALK2 antibody or antigen binding fragment thereof described herein may be mutated to include specific amino acid substitutions using standard techniques in the art, e.g., QuikChange™ mutagenesis. Nucleic acid molecules can be synthesized using a nucleotide synthesizer or PCR techniques.

A nucleic acid sequence encoding an ALK2 antibody or antigen binding fragment thereof (e.g., an ALK2 binding fragment) described herein may be inserted into a vector capable of replicating and expressing the nucleic acid molecule in prokaryotic or eukaryotic host cells. Many vectors are available in the art and can be used for the purpose of the invention. Each vector may include various components that may be adjusted and optimized for compatibility with the particular host cell. For example, the vector components may include, but are not limited to, an origin of replication, a selection marker gene, a promoter, a ribosome binding site, a signal sequence, the nucleic acid sequence encoding the protein of interest, and a transcription termination sequence.

In some embodiments, mammalian cells may be used as host cells for the invention. Examples of mammalian cell types include, but are not limited to, human embryonic kidney (HEK) (e.g., HEK293, HEK 293F), Chinese hamster ovary (CHO), HeLa, COS, PC3, Vero, MC3T3, NS0, Sp2/0, VERY, BHK, MDCK, W138, BT483, Hs578T, HTB2, BT20, T47D, NS0 (a murine myeloma cell line that does not endogenously produce any immunoglobulin chains), CRL7O3O, and HsS78Bst cells. In some embodiments, *E. coli* cells may also be used as host cells for the invention. Examples of *E. coli* strains include, but are not limited to, *E. coli* 294 (ATCC® 31,446), *E. coli* λ 1776 (ATCC® 31,537, *E. coli* BL21 (DE3) (ATCC® BAA-1025), and *E. coli* RV308 (ATCC® 31,608). Different host cells have characteristic and specific mechanisms for the posttranslational processing and modification of protein products (e.g., glycosylation). Appropriate cell lines or host systems may be chosen to ensure the correct modification and processing of the polypeptide expressed. The above-described expression vectors may be introduced into appropriate host cells using conventional techniques in the art, e.g., transformation, transfection, electroporation, calcium phosphate precipitation, and direct microinjection. Once the vectors are introduced into host cells for protein production, host cells are cultured in conventional nutrient media modified as appropriate for inducing promoters, selecting transformants, or amplifying the genes encoding the desired sequences. Methods for expression of therapeutic proteins are known in the art, see, for example, Paulina Balbas, Argelia Lorence (eds.) Recombinant Gene Expression: Reviews and Protocols (Methods in Molecular Biology), Humana Press; 2nd ed. 2004 and Vladimir Voynov and Justin A. Caravella (eds.) Therapeutic Proteins: Methods and Protocols (Methods in Molecular Biology) Humana Press; 2nd ed. 2012.

Protein Production, Recovery, and Purification

Host cells used to produce the ALK2 antibodies or antigen binding fragments (e.g., ALK2 binding fragments) thereof described herein may be grown in media known in the art and suitable for culturing of the selected host cells. Examples of suitable media for mammalian host cells include Minimal Essential Medium (MEM), Dulbecco's Modified Eagle's Medium (DMEM), Expi293™ Expression Medium, DMEM with supplemented fetal bovine serum (FBS), and RPMI-1640. Examples of suitable media for bacterial host cells include Luria broth (LB) plus necessary supplements, such as a selection agent, e.g., ampicillin. Host cells are cultured at suitable temperatures, such as from about 20° C. to about 39° C., e.g., from 25° C. to about 37° C., preferably 37° C., and $CO_2$ levels, such as 5 to 10%. The pH of the medium is generally from about 6.8 to 7.4, e.g., 7.0, depending mainly on the host organism. If an inducible promoter is used in the expression vector of the invention, protein expression is induced under conditions suitable for the activation of the promoter.

In some embodiments, depending on the expression vector and the host cells used, the expressed protein may be secreted from the host cells (e.g., mammalian host cells) into the cell culture media. Protein recovery may involve filtering the cell culture media to remove cell debris. The proteins may be further purified. An ALK2 antibody or antigen binding fragment thereof (e.g., an ALK2 binding fragment) described herein may be purified by any method known in the art of protein purification, for example, by chromatography (e.g., ion exchange, affinity, and size-exclusion column chromatography), centrifugation, differential solubility, or by any other standard technique for the purification of proteins. For example, the protein can be isolated and purified by appropriately selecting and combining affinity columns such as Protein A column (e.g., POROS Protein A chromatography) with chromatography columns (e.g., POROS HS-50 cation exchange chromatography), filtration, ultrafiltration, salting-out and dialysis procedures.

In other embodiments, host cells may be disrupted, e.g., by osmotic shock, sonication, or lysis, to recover the expressed protein. Once the cells are disrupted, cell debris may be removed by centrifugation or filtration. In some instances, a polypeptide can be conjugated to marker sequences, such as a peptide to facilitate purification. An example of a marker amino acid sequence is a hexa-histidine peptide (His-tag), which binds to nickel-functionalized agarose affinity column with micromolar affinity. Other peptide tags useful for purification include, but are not limited to, the hemagglutinin "HA" tag, which corresponds to an epitope derived from influenza hemagglutinin protein (Wilson et al., Cell 37:767, 1984).

Alternatively, the ALK2 antibodies or antigen binding fragments thereof (e.g., ALK2 binding fragments) described herein can be produced by the cells of a subject (e.g., a human), e.g., in the context of gene therapy, by administrating a vector (such as a viral vector (e.g., a retroviral vector, adenoviral vector, poxviral vector (e.g., vaccinia viral vector, such as Modified Vaccinia Ankara (MVA)), adeno-associated viral vector, and alphaviral vector)) containing a nucleic acid molecule encoding an antibody or antigen binding fragment thereof described herein. The vector, once inside a cell of the subject (e.g., by transformation, transfection, electroporation, calcium phosphate precipitation, direct microinjection, infection, etc.) will promote expression of the antibody or antigen binding fragment thereof, which is then secreted from the cell. If treatment of a disease or disorder is the desired outcome, no further action may be required. If collection of the protein is desired, blood may be collected from the subject and the protein purified from the blood by methods known in the art.

Pharmaceutical Compositions and Preparations

The ALK2 antibodies or antigen binding fragments thereof (e.g., ALK2 binding fragments) described herein can be incorporated into a vehicle for administration into a patient, such as a human patient suffering from bone disease, low red blood cell levels (e.g., low hemoglobin levels or low red blood cell count, e.g., anemia), heterotopic ossification (e.g., heterotopic ossification resulting from FOP), Sjogren's syndrome (e.g., dry eye associated with Sjogren's syndrome), MO, DIPG, PCO, or cardiac hypertrophy and/or cardiac fibrosis. In some embodiments, a pharmaceutical composition including an ALK2 antibody or an antigen binding fragment thereof (e.g., an ALK2 binding fragment) described herein may be used in combination with other agents (e.g., therapeutic biologics and/or small molecules) or compositions in a therapy. Pharmaceutical compositions containing ALK2 antibodies or antigen binding fragments thereof can be prepared using methods known in the art. For example, such compositions can be prepared using, e.g., physiologically acceptable carriers, excipients or stabilizers (Remington: The Science and Practice of Pharmacology 22nd edition, Allen, L. Ed. (2013); incorporated herein by reference), and in a desired form, e.g., in the form of lyophilized formulations or aqueous solutions. In some embodiments, a pharmaceutical composition of the invention includes a nucleic acid molecule (DNA or RNA, e.g., mRNA) encoding an antibody or ALK2 binding fragment thereof described herein, or a vector containing such a nucleic acid molecule.

Acceptable carriers and excipients in the pharmaceutical compositions are nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. Pharmaceutical compositions of the invention can be administered parenterally in the form of an injectable formulation. Pharmaceutical compositions for injection can be formulated using a sterile solution or any pharmaceutically acceptable liquid as a vehicle. Pharmaceutically acceptable vehicles include, but are not limited to, sterile water, physiological saline, and cell culture media (e.g., Dulbecco's Modified Eagle Medium (DMEM), α-Modified Eagles Medium (α-MEMI Mixtures of ALK2 antibodies or antigen binding fragments thereof (e.g., ALK2 binding fragments) may be prepared in water suitably mixed with one or more excipients, carriers, or diluents. Dispersions may also be prepared in glycerol, liquid polyethylene glycols, and mixtures thereof and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (described in U.S. Pat. No. 5,466,468, the disclosure of which is incorporated herein by reference). In any case the formulation may be sterile and may be fluid to the extent that easy syringability exists. Formulations may be stable under the conditions of manufacture and storage and may be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For example, a solution containing a pharmaceutical composition described herein may be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion. Some variation in dosage will necessarily occur depending on the condition of the subject being treated.

The pharmaceutical compositions of the invention may be prepared in microcapsules, such as hydroxylmethylcellulose or gelatin-microcapsule and poly-(methylmethacrylate) microcapsule. The pharmaceutical compositions of the invention may also be prepared in other drug delivery systems such as liposomes, albumin microspheres, microemulsions, nano-particles, and nanocapsules. Such techniques are described in Remington: The Science and Practice of Pharmacology 22nd edition, Allen, L. Ed. (2013). The pharmaceutical compositions to be used for in vivo administration must be sterile. This is readily accomplished by filtration through sterile filtration membranes.

The pharmaceutical compositions of the invention may also be prepared as a sustained-release formulation. Suitable examples of sustained-release preparations include semipermeable matrices of solid hydrophobic polymers containing the polypeptides of the invention. Examples of sustained release matrices include polyesters, hydrogels, polylactides, copolymers of L-glutamic acid and y ethyl-L-glutamate, non-degradable ethylene-vinyl acetate, degradable lactic acid-glycolic acid copolymers such as LUPRON DEPOT™, and poly-D-(−)-3-hydroxybutyric acid. Some sustained-release formulations enable release of molecules over a few months, e.g., one to six months, while other formulations release pharmaceutical compositions of the invention for shorter time periods, e.g., days to weeks.

The pharmaceutical composition may be formed in a unit dose form as needed. The amount of active component, e.g., an ALK2 antibody or an antigen binding fragment thereof (e.g., an ALK2 binding fragment) described herein, included in the pharmaceutical preparations is such that a suitable dose within the designated range is provided (e.g., a dose within the range of 0.01-100 mg/kg of body weight).

The pharmaceutical composition for gene therapy can be in an acceptable diluent, or can include a slow release matrix in which the gene delivery vehicle is imbedded. If hydrodynamic injection is used as the delivery method, the pharmaceutical composition containing a nucleic acid molecule encoding an antibody or ALK2 binding fragment thereof described herein or a vector (e.g., a viral vector) containing the nucleic acid molecule is delivered rapidly in a large fluid volume intravenously. Vectors that may be used as in vivo gene delivery vehicle include, but are not limited to, retroviral vectors, adenoviral vectors, poxviral vectors (e.g., vaccinia viral vectors, such as Modified Vaccinia Ankara), adeno-associated viral vectors, and alphaviral vectors.

Routes, Dosage, and Administration

Pharmaceutical compositions that include the ALK2 antibodies or antigen binding fragments thereof (e.g., ALK2 binding fragments) of the invention as the therapeutic agents may be by a variety of routes, such as intravenous, parenteral, intradermal, transdermal, intramuscular, intranasal, subcutaneous, percutaneous, topical, intratracheal, intraperitoneal, intraarterial, intravascular, intrathecal, intracerebroventricular, inhalation, perfusion, lavage, and oral administration. The pharmaceutical composition may also be formulated for, or administered via, oral, ocular, nasal, spray, aerosol, rectal, or vaginal administration. For injectable formulations, various effective pharmaceutical carriers are known in the art. See, e.g., ASHP Handbook on Injectable Drugs, Toissel, 18th ed. (2014). For ocular administration, the formulation may be delivered systemically, by injection (e.g., intraocular injection), or topically (e.g., as a solution, suspension, or ointment, such as by instillation (e.g., an eye drop)).

In some embodiments, a pharmaceutical composition that includes a nucleic acid molecule encoding an antibody or ALK2 binding fragment thereof described herein or a vector containing such nucleic acid molecule may be administered by way of gene delivery. Methods of gene delivery are well-known to one of skill in the art. Vectors that may be used for in vivo gene delivery and expression include, but are not limited to, retroviral vectors, adenoviral vectors, poxviral vectors (e.g., vaccinia viral vectors, such as Modified Vaccinia Ankara (MVA)), adeno-associated viral vectors, and alphaviral vectors. In some embodiments, mRNA molecules encoding polypeptides of the invention may be administered directly to a subject.

In some embodiments of the present invention, nucleic acid molecules encoding a polypeptide described herein or vectors containing such nucleic acid molecules may be administered using a hydrodynamic injection platform. In the hydrodynamic injection method, a nucleic acid molecule encoding an antibody or ALK2 binding fragment thereof described herein is put under the control of a strong promoter in an engineered plasmid (e.g., a viral plasmid). The plasmid is often delivered rapidly in a large fluid volume intravenously. Hydrodynamic injection uses controlled hydrodynamic pressure in veins to enhance cell permeability such that the elevated pressure from the rapid injection of the large fluid volume results in fluid and plasmid extravasation from the vein. The expression of the nucleic acid molecule is driven primarily by the liver. In mice, hydrodynamic injection is often performed by injection of the plasmid into the tail vein. In certain embodiments, mRNA molecules encoding an antibody or ALK2 binding fragment thereof described herein may be administered using hydrodynamic injection.

The most suitable route and dosage for administration in any given case will depend on the particular composition administered, the patient, pharmaceutical formulation methods, administration methods (e.g., administration time and administration route), the patient's age, body weight, sex, severity of the disease being treated, the patient's diet, and the patient's excretion rate. A pharmaceutical composition of the invention may include a dosage of an ALK2 antibody or an antigen binding fragment thereof (e.g., an ALK2 binding fragment) of the invention ranging from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg) and, in a more specific embodiment, about 0.1 to about 30 mg/kg and, in a more specific embodiment, about 0.3 to about 30 mg/kg. The dosage may be adapted by the physician in accordance with conventional factors such as the extent of the disease and different parameters of the subject.

The pharmaceutical compositions are administered in a manner compatible with the dosage formulation and in such amount as is therapeutically effective to result in an improvement or remediation of the symptoms. The pharmaceutical compositions are administered in a variety of dosage forms, e.g., intravenous dosage forms, subcutaneous dosage forms, and oral dosage forms (e.g., ingestible solutions, drug release capsules). Generally, therapeutic antibodies are dosed at 0.1-100 mg/kg, e.g., 1-50 mg/kg. Pharmaceutical compositions that include an ALK2 antibody or an antigen binding fragment thereof (e.g., an ALK2 binding fragment) of the invention may be administered to a subject in need thereof, for example, one or more times (e.g., 1-10 times or more) daily, weekly, biweekly, monthly, bimonthly, quarterly, biannually, annually, or as medically necessary. In some embodiments, pharmaceutical compositions that include an ALK2 antibody or an antigen binding fragment thereof (e.g., an ALK2 binding fragment) of the invention may be administered to a subject in need thereof weekly, biweekly, monthly, bimonthly, or quarterly. Dosages may be provided in either a single or multiple dosage regimens. The timing between administrations may decrease as the medical condition improves or increase as the health of the patient declines.

Methods of Treatment

The compositions and methods described herein can be used to treat and/or prevent (e.g., prevent the development of or treat a subject diagnosed with) medical conditions, e.g., bone disease, anemia or low red blood cell levels (e.g., low hemoglobin levels or low red blood cell count), heterotopic ossification (e.g., heterotopic ossification resulting from FOP), Sjogren's syndrome (e.g., dry eye associated with Sjogren's syndrome), DIPG, MO, PCO, or cardiac hypertrophy and/or cardiac fibrosis. In some embodiments, the ALK2 antibodies (e.g., neutralizing antibodies) or antigen binding fragments thereof (e.g., ALK2 binding fragments) described herein are administered to increase bone mineral density, increase bone formation, increase bone strength, reduce bone resorption (e.g., bone loss), or reduce the risk of bone fracture in a subject in need thereof. The ALK2 antibodies or antigen binding fragments thereof (e.g., ALK2 binding fragments) described herein may increase bone mineral density, increase bone formation, increase bone strength, reduce bone resorption (e.g., bone loss), or reduce the risk of bone fracture compared to measurements obtained prior to treatment or compared to bone mineral density, bone strength, bone formation, bone resorption, or risk of bone fracture typically observed in untreated subjects. In some embodiments, the subject may have or be at risk of developing a disease that results in bone damage (e.g., osteoporosis or osteopenia). In some embodiments of the methods described herein, the subject has or is at risk of developing a disease or condition involving bone damage (e.g., primary osteoporosis, secondary osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss). The invention also includes methods of treating a subject having or at risk of developing primary osteoporosis, secondary osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss, by administering to the subject an effective amount of an ALK2 antibody or an antigen binding fragment thereof (e.g., an ALK2 binding fragment) described herein.

In any of the methods described herein, a subject having or at risk of developing bone disease (e.g., bone damage) has or is at risk of developing a disease or condition including primary osteoporosis, secondary osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss. In some embodiments, the primary osteoporosis is age-related or hormone-related osteoporosis (e.g., related to a decline in estrogen). In some embodiments, the secondary osteoporosis is immobilization-induced or glucocorticoid-induced osteoporosis. In some embodiments, the bone cancer is multiple myeloma or the cancer metastasis-related bone loss is caused by multiple myeloma. In some embodiments, the treatment-related bone loss occurs due to treatment with FGF-21 or GLP-1, due to treatment with an FGF-21 or GLP-1 containing therapeutic, due to treatment of Type-2 diabetes and/or obesity, or due to cancer therapy (e.g., chemotherapy or radiation). In some embodiments, the diet-related bone loss is rickets (e.g., vitamin D deficiency). In some embodiments, the low-gravity related bone loss is lack of load-related bone loss. In some embodiments, the methods described herein increase bone mineral density (e.g., increase bone mass). In some embodiments, the methods described herein reduce bone resorption (e.g., reduce bone catabolic activity or reduce bone loss), e.g., reduce bone resorption compared to measurements obtained prior to treatment or compared to bone resorption typically observed in untreated subjects. In some embodiments, the methods described herein increase bone formation (e.g., increase bone anabolic activity or increase osteogenesis), e.g., increase bone formation compared to measurements obtained prior to treatment or compared to bone formation typically observed in untreated subjects. In some embodiments, the methods described herein increase osteoblast activity or osteoblastogenesis, e.g., increase osteoblast activity or osteoblastogenesis compared to measurements obtained prior to treatment or compared to osteoblast activity or osteoblastogenesis typically observed in untreated subjects. In some embodiments, the methods described herein decrease osteoclast activity or osteoclastogenesis, e.g., decrease osteoclast activity or osteoclastogenesis compared to measurements obtained prior to treatment or compared to osteoclast activity or osteoclastogenesis typically observed in untreated subjects. In some embodiments, the bone is cortical or trabecular bone.

In some embodiments, the ALK2 antibodies or antigen binding fragments thereof (e.g., ALK2 binding fragments) described herein are administered to increase red blood cell levels (e.g., increase hemoglobin levels, increase red blood cell count, or increase red blood cell formation or production) in a subject in need thereof. The ALK2 antibodies or antigen binding fragments thereof (e.g., ALK2 binding fragments) described herein may increase red blood cell levels (e.g., increase hemoglobin levels, red blood cell count, or red blood cell formation) compared to measurements obtained prior to treatment or compared to red blood cell levels typically observed in untreated subjects. In some embodiments, the subject may have a disease or condition associated with low red blood cell levels (e.g., anemia or blood loss). In some embodiments of the methods described herein, the subject has or is at risk of developing a disease or condition involving low red blood cell levels (e.g., anemia or blood loss, such as aplastic anemia, iron deficiency anemia, iron-refractory iron deficiency anemia (IRIDA), or anemia of inflammation (also called anemia of chronic disease, e.g., anemia caused by inflammatory diseases or conditions, such as infection (e.g., chronic infection, such as HIV/AIDS or tuberculosis), autoimmune disease (e.g., rheumatoid arthritis or lupus), cancer (e.g., cancer or cancer treatment), inflammatory bowel disease (e.g., Crohn's disease or ulcerative colitis), and chronic kidney disease). The invention also includes methods of treating a subject having or at risk of developing low red blood cell levels (e.g., low hemoglobin levels or low red blood cell count, e.g., anemia) by administering to the subject an effective amount of an ALK2 antibody or an antigen binding fragment thereof (e.g., an ALK2 binding fragment) described herein. The methods described herein may include a step of screening a subject for one or more mutations in genes known to be associated with anemia (e.g., mutations in TMPRSS6, which are associated with IRIDA) prior to treatment with or administration of the compositions described herein. A subject can be screened for a genetic mutation using standard methods known to those of skill in the art (e.g., genetic testing).

The invention also includes methods of treating a subject having or at risk of developing anemia or blood loss by administering to the subject an effective amount of an ALK2 antibody or an antigen binding fragment thereof (e.g., an ALK2 binding fragment) described herein. In any of the methods described herein, a subject having or at risk of developing low red blood cell levels (e.g., low hemoglobin levels or low red blood cell counts) has or is at risk of developing anemia or blood loss. In some embodiments, the anemia is associated with nutritional deficits (e.g., vitamin deficiency), bone marrow defects (e.g., paroxysmal nocturnal hemoglobinuria), adverse reaction to medication (e.g., anti-retroviral HIV drugs), myelodysplastic syndrome, bone marrow transplantation, cancer (e.g., solid tumors, such as breast cancer, lung cancer, colon cancer; tumors of the lymphatic system, such as chronic lymphocyte leukemia, non-Hodgkin's lymphoma, Hodgkin's lymphoma; or tumors of the hematopoietic system, such as leukemia or multiple myeloma), cancer treatment (e.g., radiation or chemotherapy, e.g., chemotherapy with platinum-containing agents), inflammatory or autoimmune disease (e.g., rheumatoid arthritis, other inflammatory arthritides, systemic lupus erythematosus (SLE), acute or chronic skin diseases (e.g. psoriasis), or inflammatory bowel disease (e.g., Crohn's disease or ulcerative colitis), cystitis, gastritis), acute or chronic renal disease or failure (e.g., chronic kidney disease) including idiopathic or congenital conditions, acute or chronic liver disease, acute or chronic bleeding, infection (e.g., malaria, osteomyelitis), splenomegaly, porphyria, vasculitis, hemolysis, urinary tract infection, hemoglobinopathy (e.g., sickle cell disease), thalassemia, Churg-Strauss syndrome, Felty syndrome, graft versus host disease, hematopoietic stem cell transplantation, osteomyelofibrosis, pancytopenia, pure red-cell aplasia, purpura Schoenlein-Henoch, Shwachman syndrome (e.g., Shwachman-Diamond syndrome), drug use or abuse (e.g., alcohol abuse), or contraindication to transfusion (e.g., patients of advanced age, patients with allo- or auto-antibodies, pediatric patients, patients with cardiopulmonary disease, patients who object to transfusion for religious reasons (e.g., some Jehovah's Witnesses)). In some embodiments, the anemia is aplastic anemia, iron deficiency anemia, iron-refractory iron deficiency anemia (IRIDA), vitamin deficiency anemia, anemia of inflammation (also called anemia of chronic disease, e.g., anemia caused by inflammatory diseases or conditions, such as infections (e.g., chronic infections, such as HIV/AIDS or tuberculosis), autoimmune diseases (e.g., rheumatoid arthritis or lupus), cancer, inflammatory bowel disease (e.g., Crohn's disease or ulcerative colitis), and chronic kidney disease), anemia associated with bone marrow disease, hemolytic anemia, sickle cell anemia, microcytic anemia, hypochromic anemia, sideroblastic anemia, Diamond Blackfan anemia, Fanconi's anemia, or refractory anemia with excess of blasts. In some embodiments, the anemia is associated with elevated hepcidin levels (e.g., elevated compared to hepcidin levels in a subject that does not have anemia). The compositions and methods described herein can also be used to treat subjects that do not respond well to erythropoietin (EPO) or that are susceptible to adverse effects of EPO (e.g., hypertension, headaches, vascular thrombosis, influenza-like syndrome, obstruction of shunts, and myocardial infarction). In some embodiments, the blood loss is due to surgery, trauma, a wound, an ulcer, urinary tract bleeding, digestive tract bleeding, frequent blood donation, or heavy menstrual bleeding (e.g., menorrhagia). In some embodiments, the methods described herein increase red blood cell levels (e.g., hemoglobin levels or red blood cell counts) compared to measurements obtained prior to treatment or compared to red blood cell levels typically observed in untreated subjects. In some embodiments, the methods described herein increase or induce red blood cell formation compared to measurements obtained prior to treatment or compared to red blood cell formation typically observed in untreated subjects. In some embodiments, the compositions and methods described herein reduce the need of a subject for a blood transfusion (e.g., the subject no longer needs blood transfusions, or the subject needs less frequent blood transfusion than before treatment with the compositions and methods described herein). Subjects with normal red blood cell levels can also be treated using the methods and compositions described herein to increase red blood cell levels so that blood can be drawn and stored for later use in transfusions.

In some embodiments, the ALK2 antibodies or antigen binding fragments thereof (e.g., ALK2 binding fragments) described herein may be administered to a subject to treat FOP, to slow or stop the progression of FOP, to delay the onset of FOP (e.g., delay the development of heterotopic ossification), or to prevent or reduce heterotopic ossification (e.g., the formation of bone in muscle, tendons, ligaments, or other connective tissues, e.g., prevent or reduce heterotopic ossification in a subject with FOP who has already experienced heterotopic ossification, or prevent the development of heterotopic ossification in a subject who has not yet exhibited heterotopic ossification), such as heterotopic ossification in a subject with FOP. The FOP can be inherited FOP (e.g., FOP related to germline transmission of a mutation, such as an autosomal dominant mutation) or sporadic FOP (e.g., FOP related to a spontaneous, non-inherited mutation). The ALK2 antibodies or antigen binding fragments thereof (e.g., ALK2 binding fragments) described herein may reduce the amount of heterotopic bone, reduce the formation of heterotopic bone, or reduce the recurrence of heterotopic bone (e.g., recurrence after surgical resection) compared to the amount of heterotopic bone, formation of heterotopic bone, or recurrence of heterotopic bone observed in untreated or control treated subjects. The ALK2 antibodies or antigen binding fragments thereof (e.g., ALK2 binding fragments) described herein may prevent the formation of heterotopic bone (e.g., in a subject at risk of developing heterotopic ossification, such as a subject with FOP, or prevent the recurrence of heterotopic bone, such as recurrence after surgical resection). In some embodiments, the subject is at risk of developing heterotopic ossification (e.g., the subject has a genetic mutation associated with FOP but has not yet exhibited symptoms of FOP, e.g., has not yet exhibited heterotopic ossification). The methods described herein may include a step of screening a subject for one or more mutations in genes known to be associated with FOP (e.g., mutations in ALK2, also known as Activin A type I receptor (ACVR1)) prior to treatment with or administration of the compositions described herein. A subject can be screened for a genetic mutation using standard methods known to those of skill in the art (e.g., genetic testing).

In some embodiments, the ALK2 antibodies or antigen binding fragments thereof (e.g., ALK2 binding fragments) described herein may be administered to a subject to treat Sjogren's syndrome (e.g., to treat dry eye associated with Sjogren's syndrome) or to reduce one or more symptom of Sjogren's syndrome (e.g., to reduce dry eye or dry mouth associated with Sjogren's syndrome). The ALK2 antibodies or antigen binding fragments thereof (e.g., ALK2 binding fragments) described herein may reduce eye irritation, reduce fibrosis of the lacrimal gland, reduce inflammation of the lacrimal gland, improve vision, increase the production of saliva, increase the production of tears (e.g., increase tear volume production), reduce systemic inflammation, reduce joint pain, or reduce fatigue in a subject with Sjogren's syndrome, or reduce the severity or occurrence of one or more symptom of Sjogren's syndrome (e.g., reduce dry eye, dry mouth, or joint pain associated with Sjogren's syndrome) compared to eye irritation, vision, inflammation or fibrosis of the lacrimal gland, the production of saliva, the production of tears, systemic inflammation, joint pain, fatigue, or the severity or occurrence of symptoms of Sjogren's syndrome in the subject prior to treatment or in an untreated subject with Sjogren's syndrome.

In some embodiments, the ALK2 antibodies or antigen binding fragments thereof (e.g., ALK2 binding fragments) described herein may be administered to a subject to treat DIPG, increase the survival (e.g., survival time, e.g., lifespan) of a subject having DIPG, increase progression free survival of a subject having DIPG, reduce DIPG tumor growth, reduce DIPG tumor size or volume, or prevent or reduce DIPG tumor metastasis. The ALK2 antibodies or antigen binding fragments thereof (e.g., ALK2 binding fragments) described herein may increase the survival (e.g., survival time, e.g., lifespan) of a subject having DIPG, increase progression free survival of a subject having DIPG, reduce DIPG tumor growth, reduce DIPG tumor size or volume, or prevent or reduce DIPG tumor metastasis compared survival time, progression free survival, tumor growth, tumor size or volume, or tumor metastasis compared to untreated or control treated subjects or compared to tumor growth, tumor size or volume, or tumor metastasis in the subject prior to treatment. In some embodiments, the subject has an activating mutation in ALK2 (ACVR1). The methods described herein may include a step of screening a subject for a mutation in ALK2 (ACVR1) prior to treatment with or administration of the compositions described herein. A subject can be screened for a genetic mutation using standard methods known to those of skill in the art (e.g., genetic testing).

In some embodiments, the ALK2 antibodies or antigen binding fragments thereof (e.g., ALK2 binding fragments) described herein may be administered to a subject to treat MO, reduce or prevent the formation of an osteochondroma in a subject with MO, reduce the number of osteochondromas in a subject with MO, reduce the size of an osteochondroma in a subject with MO, or slow the growth of an osteochondroma in a subject with MO. The osteochondroma can be formed on the growing end (metaphysis) of a bone, on a long bone (e.g., a long bone of the leg, arm, or digit), and/or on a flat bone (e.g., a hip bone (pelvic bone), rib bone, or shoulder blade). The ALK2 antibodies or antigen binding fragments thereof (e.g., ALK2 binding fragments) described herein may reduce or prevent the formation of an osteochondroma (e.g., prevent the formation of an osteochondroma in a subject with MO who has not yet developed osteochondroma or reduce or prevent the formation of osteochondroma in a subject with MO who has already developed one or more osteochondroma), reduce the number of osteochondromas, reduce the size of an osteochondroma, or slow the growth of an osteochondroma compared to the formation of an osteochondroma, the number of osteochondromas, the size of an osteochondroma, or the growth of an osteochondroma in the subject prior to treatment or in an untreated subject with MO. The methods described herein may include a step of screening a subject for a mutation in EXT1 or EXT2 prior to treatment with or administration of the compositions described herein. A subject can be screened for a genetic mutation using standard methods known to those of skill in the art (e.g., genetic testing).

In some embodiments, the ALK2 antibodies or antigen binding fragments thereof (e.g., ALK2 binding fragments) described herein may be administered to a subject to treat PCO, reduce or prevent the development of PCO (e.g., to prevent the development of PCO in a subject who has undergone cataract surgery but has not yet developed PCO or in a subject who is soon to undergo cataract surgery, e.g., a subject who will undergo cataract surgery in 6 months, 5 months, 4 months, 3, months, 2 months, 1 month, 2 weeks, 1 week, or less, e.g., a subject at risk of developing PCO), improve visual acuity (e.g., reduce blurry or cloudy vision) in a subject with PCO, reduce light sensitivity or glare in a subject with PCO, reduce or prevent fibrosis (e.g., fibrosis near the implanted lens, e.g., fibrosis on or near the posterior capsule), reduce or inhibit lens epithelial cell proliferation, reduce or prevent lens fiber differentiation, or reduce or prevent inflammation in the eye in a subject having PCO or at risk of developing PCO (e.g., in a subject who has undergone or is soon to undergo cataract surgery e.g., a subject who will undergo cataract surgery in 6 months, 5 months, 4 months, 3, months, 2 months, 1 month, 2 weeks, 1 week, or less). The ALK2 antibodies or antigen binding fragments thereof (e.g., ALK2 binding fragments) described herein may reduce or prevent the development of PCO, reduce or prevent fibrosis (e.g., fibrosis near the implanted lens, e.g., fibrosis on or near the posterior capsule), reduce or prevent lens fiber differentiation, reduce or inhibit lens epithelial cell proliferation, or reduce or prevent eye inflammation in a subject at risk of developing PCO compared the development of PCO, fibrosis (e.g., fibrosis near the implanted lens, e.g., fibrosis on or near the posterior capsule), lens fiber differentiation, lens epithelial cell proliferation, or eye inflammation in an untreated subject, or may improve visual acuity (e.g., reduce blurry or cloudy vision) or reduce light sensitivity or glare, reduce fibrosis, reduce eye inflammation, reduce lens epithelial cell proliferation, or reduce lens fiber differentiation compared to visual acuity, light sensitivity or glare, fibrosis, eye inflammation, lens epithelial cell proliferation, or lens fiber differentiation in the subject prior to treatment.

In some embodiments, the ALK2 antibodies or antigen binding fragments thereof (e.g., ALK2 binding fragments) described herein may be administered to a subject to treat cardiac hypertrophy, treat cardiac fibrosis, slow or prevent the development of cardiac hypertrophy (e.g., in a subject at risk of developing cardiac hypertrophy, such as a subject with hypertension or valvular disease), slow or prevent the development of cardiac fibrosis (e.g., in a subject at risk of developing cardiac fibrosis, such as a subject with hypertension, a subject who has had a myocardial infarction, a subject with diabetic hypertrophic cardiomyopathy, or a subject with idiopathic dilated cardiomyopathy), reverse cardiac fibrosis, reduce or inhibit cardiac scar formation, increase or induce cardiac regeneration, or improve one or more symptoms of cardiac hypertrophy or cardiac fibrosis (e.g., increase exercise capacity, increase blood ejection volume, reduce left ventricular end diastolic pressure, reduce pulmonary capillary wedge pressure, increase cardiac output, increase cardiac index, reduce pulmonary artery pressures, reduce left ventricular end systolic and diastolic dimensions, reduce left and right ventricular wall stress, reduce wall tension and/or wall thickness, increase myocardial contractility, reduce cardiomyocyte area, reduce extracellular matrix deposition in the cardiac muscle, improve quality of life, and/or reduce disease-related morbidity and mortality). The ALK2 antibodies or antigen binding fragments thereof (e.g., ALK2 binding fragments) described herein slow or prevent the development of cardiac hypertrophy, slow or prevent the development of cardiac fibrosis, reverse cardiac fibrosis, reduce or inhibit cardiac scar formation, increase or induce cardiac regeneration, or improve one or more symptoms of cardiac hypertrophy or cardiac fibrosis in a subject having or risk of developing cardiac hypertrophy or cardiac fibrosis compared to the development of cardiac hypertrophy, the development of cardiac fibrosis, the extent of cardiac fibrosis, cardiac scar formation, cardiac regeneration, or one or more symptoms of cardiac hypertrophy or cardiac fibrosis in the subject prior to treatment or in an untreated or control treated subject.

The compositions described herein are administered in an amount sufficient to increase bone mineral density, increase bone strength, density, reduce bone resorption (e.g., bone loss), reduce the rate of bone resorption (e.g., bone loss), increase bone formation, increase the rate of bone formation, reduce osteoclast activity, increase osteoblast activity, reduce the risk of bone fracture, increase red blood cell levels, increase hemoglobin levels, reduce the need for a transfusion, increase red blood cell formation, or increase red blood cell count, treat anemia, increase iron levels, reduce iron deficiency, decrease elevated hepcidin levels, treat FOP, prevent heterotopic ossification (e.g., prevent the initial formation of ectopic bone in a subject or prevent the recurrence of ectopic bone after surgical resection), slow or stop the progression of FOP, delay the onset of FOP (e.g., delay the onset of heterotopic ossification), reduce heterotopic ossification (e.g., reduce the amount of ectopic bone in a subject or reduce the formation of ectopic bone, such as the initial formation of ectopic bone or the recurrence of ectopic bone after surgical resection), treat Sjogren's syndrome, reduce dry eye associated with Sjogren's syndrome, reduce dry mouth associated with Sjogren's syndrome, reduce eye inflammation, increase the production of saliva, increase the production of tears, reduce systemic inflammation, reduce joint pain, reduce fatigue, reduce the severity or occurrence of symptoms of Sjogren's syndrome (e.g., reduce dry eye, dry mouth, or joint pain associated with Sjogren's syndrome), treat DIPG, increase the survival (e.g., survival time, e.g., lifespan) of a subject having DIPG, increase progression free survival of a subject having DIPG, reduce DIPG tumor growth, reduce DIPG tumor size or volume, prevent or reduce DIPG tumor metastasis, treat MO, reduce or prevent the formation of an osteochondroma in a subject with MO, reduce the number of osteochondromas in a subject with MO, reduce the size of an osteochondroma in a subject with MO, slow the growth of an osteochondroma in a subject with MO, reduce or prevent the development of PCO, improve visual acuity (e.g., reduce blurry or cloudy vision) in a subject with PCO, reduce light sensitivity or glare in a subject with PCO, reduce or prevent fibrosis (e.g., fibrosis near the implanted lens, e.g., fibrosis on or near the posterior capsule), reduce or inhibit lens epithelial cell proliferation, reduce or prevent lens fiber differentiation, or reduce or prevent inflammation in the eye of a subject with PCO, treat cardiac hypertrophy, treat cardiac fibrosis, slow or prevent the development of cardiac hypertrophy, slow or prevent the development of cardiac fibrosis, reverse cardiac fibrosis, reduce or inhibit cardiac scar formation, increase or induce cardiac regeneration, or improve one or more symptoms of cardiac hypertrophy or cardiac fibrosis (e.g., increase exercise capacity, increase blood ejection volume, reduce left ventricular end diastolic pressure, reduce pulmonary capillary wedge pressure, increase cardiac output, increase cardiac index, reduce pulmonary artery pressures, reduce left ventricular end systolic and diastolic dimensions, reduce left and right ventricular wall stress, reduce wall tension and/or wall thickness, increase myocardial contractility, reduce extracellular matrix deposition in the cardiac muscle, improve quality of life, and/or reduce disease-related morbidity and mortality). Bone mineral density can be evaluated using well-established clinical techniques known to one of skill in the art (e.g., by dual-energy x-ray absorptiometry). Red blood cell levels can be assessed using a standard blood test, which measures red blood cell counts and hemoglobin levels. FOP symptoms (e.g., heterotopic ossification) and MO (e.g., osteochondromas) can be evaluated using standard imaging methods, such as radiographs (e.g., X-rays), CT (computed tomography), and/or MRI (magnetic resonance imaging). DIPG tumor size, growth, volume or metastasis, may be assessed using imaging methods, such as MRI. Symptoms of cardiac hypertrophy and/or cardiac fibrosis may be evaluated using clinical approaches to evaluate heart function and morphology (e.g., a stress test, echocardiogram, CT, MRI, cardiac magnetic resonance imaging, single photon emission computed tomography, positron emission tomography, a balloon catheter-based approach, or histological analysis of a biopsy). Sjogren's syndrome and PCO symptoms may be assessed by evaluating visual function and imaging the eye to assess inflammation and/or fibrosis (e.g., using slit lamp imaging to evaluate fibrosis forming on the posterior capsule). The methods described herein may also include a step of assessing bone mineral density, red blood cell levels, or symptoms of FOP, DIPG, MO, PCO, Sjogren's syndrome, or cardiac hypertrophy and/or cardiac fibrosis in a subject prior to treatment with or administration of the compositions described herein or after administration of or treatment with the compositions described herein. The subject may be evaluated 1 month, 2 months, 3 months, 4 months, 5 months, 6 months or more following administration of the ALK2 antibody or an antigen binding fragment thereof (e.g., an ALK2 binding fragment) or pharmaceutical composition depending on the dose and route of administration used for treatment. Depending on the outcome of the evaluation, the subject may receive additional treatments.

Nucleic acids encoding the ALK2 antibodies or antigen binding fragments thereof (e.g., ALK2 binding fragments) described herein, or expression vectors containing said nucleic acids can also be administered according to any of the methods described herein. In any of the methods described herein, the polypeptide, nucleic acid, or vector can be administered as part of a pharmaceutical composition.

Kits

The compositions described herein can be provided in a kit for use in treating bone disease, anemia, FOP, Sjogren's syndrome (e.g., dry eye associated with Sjogren's syndrome), MO, DIPG, PCO, or cardiac hypertrophy and/or cardiac fibrosis. Compositions may include an ALK2 antibody or antigen binding fragment thereof (e.g., an ALK2 binding fragment) described herein, and may be provided in unit dosage form, optionally in a pharmaceutically acceptable excipient (e.g., saline), in an amount sufficient to treat bone disease, anemia, FOP, Sjogren's syndrome (e.g., dry eye associated with Sjogren's syndrome), MO, DIPG, PCO, or cardiac hypertrophy and/or cardiac fibrosis. The kit can further include a package insert that instructs a user of the kit, such as a physician, to perform the methods described herein. The kit may optionally include a syringe or other device for administering the composition.

EXAMPLES

The following examples are provided to further illustrate some embodiments of the present invention, but are not intended to limit the scope of the invention; it will be understood by their exemplary nature that other procedures, methodologies, or techniques known to those skilled in the art may alternatively be used.

Example 1—Generation of ALK2 Antibodies

Antibody was generated by panning the Human combinatorial phage library for antibodies recognizing ALK2, followed by 2 rounds of enrichment, and counter-selected against the closely-related antigens for depletion of unspecific antibodies. After the second round of enrichment, a Rapid Pool Maturation "RAPMAT®" (Prassler et al., Immunotherapy, 1(4), 571-583, 2009) was performed (RAPMAT® is a registered trademark of MorphoSys AG). A highly diverse set of CDR variability was cloned into the selected antibody pool, thus further expanding the diversity of the pre-selected antibody pool. The resultant expanded antibody library was panned against ALK2 with another 2 rounds of enrichment using high stringency washing conditions and reduction of antigen amount in the panning rounds, and counter-selected against closely-related antigens for depletion of unspecific antibodies. After the panning, the enriched antibody gene pool was subcloned from the phage display vector into a bacterial expression vector determining the final Fab antibody format as indicated in Table 2, below.

TABLE 2

Antibody CDR sequences

| | VL | | | VH | | |
|---|---|---|---|---|---|---|
| Antibody | CDR1 | CDR2 | CDR3 | CDR1 | CDR2 | CDR3 |
| 1 | SGSSSNIGSNYVS (SEQ ID NO: 1) | VLIYKNNHRPS (SEQ ID NO: 24) | ASWDHSDRFYV (SEQ ID NO: 4) | GGTFSSYGVS (SEQ ID NO: 31) | WMGGIIPHFGIANYAQKFQG (SEQ ID NO: 36) | EIGSLDI (SEQ ID NO: 13) |

TABLE 2-continued

Antibody CDR sequences

| Antibody | VL CDR1 | VL CDR2 | VL CDR3 | VH CDR1 | VH CDR2 | VH CDR3 |
|---|---|---|---|---|---|---|
| 2 | SGDSIPSFFAS (SEQ ID NO: 18) | LVIYRDSNRPS (SEQ ID NO: 25) | YVTAPWKSIW (SEQ ID NO: 5) | GFTFSSHAMS (SEQ ID NO: 32) | WVGRIKSKADSGTTDYAAPVKG (SEQ ID NO: 37) | DYGVAFAY (SEQ ID NO: 14) |
| 3 | SGDNIGTKYAY (SEQ ID NO: 19) | LVIYGDSDRPS (SEQ ID NO: 26) | YSADAQQMKA (SEQ ID NO: 6) | GFTFNSSAMS (SEQ ID NO: 33) | WVGRIKSKRDGYTTDYAAPVKG (SEQ ID NO: 38) | DYGGLKFDY (SEQ ID NO: 15) |
| 4 | SGDNLRKYSAH (SEQ ID NO: 20) | LVIYYDNKRPS (SEQ ID NO: 27) | QVYASVHRM (SEQ ID NO: 7) | GGTFSSYAIH (SEQ ID NO: 34) | WMGRIIPDFGTANYAQKFQG (SEQ ID NO: 39) | GPTQAIHYFAY (SEQ ID NO: 16) |
| 5 | SGDSLGSKSVH (SEQ ID NO: 21) | LVIYRDSKRPS (SEQ ID NO: 28) | QTYDWSHFGW (SEQ ID NO: 8) | GFTFSSAAMH (SEQ ID NO: 35) | WVSVISSDGGSTYYADSVKG (SEQ ID NO: 12) | AGFILGSLGVAWMDV (SEQ ID NO: 17) |
| 6 | RASQGISGNWLT (SEQ ID NO: 40) | LLIYDASNLQS (SEQ ID NO: 41) | HQSYRGPM (SEQ ID NO: 42) | GFTFGRFVMH (SEQ ID NO: 43) | WVSVIGYSGSSTYYADSVKG (SEQ ID NO: 44) | EPGYYYPSGYYRGPGYWMDV (SEQ ID NO: 45) |
| 7 | SGDNIRKKYVH (SEQ ID NO: 46) | LVIYRDSNRPS (SEQ ID NO: 47) | SSAGRDNY (SEQ ID NO: 48) | GFTFSSSAMH (SEQ ID NO: 49) | WVSVIHYDSSETYYADSVKG (SEQ ID NO: 50) | DRYFFDV (SEQ ID NO: 51) |
| 8 | SGDALRYYIAH (SEQ ID NO: 52) | LVIYYNNNRPS (SEQ ID NO: 53) | QSYGPGSV (SEQ ID NO: 54) | GFTFSDYAMH (SEQ ID NO: 55) | WVSSIFYSGSNTYYADSVKG (SEQ ID NO: 56) | PKSYASGPFAY (SEQ ID NO: 57) |
| 9 | SGSSSNIGQNYVS (SEQ ID NO: 58) | LLIYDNSKRPS (SEQ ID NO: 59) | SSWDLLSKSR (SEQ ID NO: 60) | GGTFSTHAIS (SEQ ID NO: 61) | WMGLIQPRFGTANYAQKFQR (SEQ ID NO: 62) | DYYGGMAY (SEQ ID NO: 63) |

Example 2—Evaluation of ALK2 Antibody Binding Affinity by Surface Plasmon Resonance (SPR)

The GE Biacore 3000 was used to measure the kinetics of the interactions between the Anti-ALK2 Antibodies (Ligands) and ALK2-His/ALK2-mFC (Analytes). Flow cells 1~4 were immobilized with anti-human capture antibodies from GE using the amine coupling kit. The Anti-ALK2 proteins were then captured on the chip in flow cells 2-4, with flow cell 1 being left empty as a reference cell to measure and subtract any nonspecific binding. When running kinetic assays on the Biacore, it is best to allow a maximum analyte binding response (RMax) of 100 resonance units (RU). This is achieved through the formula RMax 100=(kDa Analyte/kDa Ligand)×Immobilized ligand RU. If there is too high a density of ligand in the flow cell it will result in an artificially low concentration of unbound analyte close to the chip surface, and the resulting sensorgram will not represent the true binding between the ligand and analyte. This is referred to as the mass transport effect and it is prevented by calculating the appropriate level of ligand to bind to the chip surface, as well has using a high flow rate of 40 L/min. HBS-EP+ was used as running buffer and to dilute proteins. Each ligand was run in a duplicate concentration series. At the end of each cycle, the chip was regenerated to remove all bound Anti-ALK2 and analyte with 3M MgCl2. The kinetics of the interactions between the monovalent fAB antibodies in fAB-FH format and ALK2-FC were also measured using the ForteBio Octet RED384.

Shown in Table 3 below, are $K_D$ values for fABs for Antibody 1, Antibody 2, and Antibody 3 as measured by ForteBio Octet against ALK2-FC and $K_D$ values of complete antibodies measured by GE Biacore against ALK2-His. Table 4 shows the $K_D$ value of Antibody 2 measured by GE Biacore against ALK2-mFC. Table 5 shows the $k_a$, $k_d$, and $K_D$ values for the interactions between the monovalent fAB antibodies in fAB-FH format and ALK2-FC as measured using the ForteBio Octet RED384.

TABLE 3

$K_D$ values

| | $K_D$ (nM) | |
|---|---|---|
| Antibody | ForteBio Octet | GE Biacore |
| 1 | 4.0 | 3.1 |
| 2 | 0.7 | 0.4 |
| 3 | 4.4 | 3.9 |

TABLE 4

K$_D$ value against ALK2-mFC

| Antibody | K$_D$ (nM) GE Biacore |
|---|---|
| 2 | 0.145 |

TABLE 5

Kinetics of monovalent fAB antibodies in fAB-FH format measured by ForteBio Octet

| Sample ID (Antibody) | k$_a$ [1/s] | k$_d$ [1/s] | K$_D$ [nM] |
|---|---|---|---|
| 6 | 1.20E+06 | 3.49E-03 | 2.9 |
| 7 | 6.97E+04 | 1.63E-03 | 23 |
| 8 | 9.11E+05 | 5.76E-03 | 6.3 |
| 9 | 1.02E+06 | 1.49E-02 | 14 |
| 1 | 4.30E+05 | 1.72E-03 | 4.0 |
| 2 | 5.51E+05 | 3.57E-04 | 0.7 |
| 3 | 3.42E+05 | 1.49E-03 | 4.4 |
| 4 | 4.20E+05 | 7.59E-04 | 1.8 |
| 5 | 2.04E+05 | 3.64E-04 | 1.8 |

Example 3—Evaluation of ALK2 Antibody Using a Gene Luciferase Reporter Assay

C2C12-BRE-Luciferase (SMAD1 reporter) cells were plated on 96 well plates in DMEM supplemented with 2% FBS and placed in an incubator for no less than 3 hours to acclimate to the plate surface. For each fAb variant, a dilution series was made in 2% DMEM and dosed onto the cells. The remaining wells were used for replicates of positive controls and background. The cells were then placed in the incubator for 45 minutes at 37° C. Wells were treated with either vehicle (to determine background values), BMP6 (to determine ALK2 stimulation values) or with fAB followed by 40 ng/ml BMP6 (to determine the IC50 for the fAbs). The extent of BRE-stimulated luciferase was measured as a surrogate for SMAD1 phosphorylation. Plates were incubated overnight, and then read using Promega Steady Glo and the Molecular Devices Spectramax M5e. Inhibition was calculated as the percent of signal loss compared to the positive control wells. FIGS. 1A-1B show the BMP6 inhibition dose response curves of Anti-ALK2 fABs performed on C2C12 cells with a SMAD1 luciferase reporter. Fifty percent inhibition values (IC50) for both a three and four parameter curve fit in Graphpad Prism are displayed next to the curves. FIG. 1A shows the results from the first four fABs generated, and FIG. 1B shows the results from five second round fABs generated using Rapid Pool Maturation.

Example 4—Effect of ALK2 Antibody in a Mouse Model of IRIDA

Eight-week old, male C57BL/6 mice were treated with either vehicle or ALK2 antibody (5 mg/kg Antibody 2, twice weekly, intraperitoneal injections). Six days after dose initiation, vehicle-treated mice were dosed intravenously with a lipid encapsulated siRNA targeted against either Luciferase (control) or TMPRSS6 (0.3 mg/kg). TMPRSS6 encodes a transmembrane type II serine protease that suppresses hepcidin secretion by cleaving hemojuvelin, and mutations in TMPRSS6 have been observed in human subjects with IRIDA. ALK2 antibody treated mice were administered TMPRSS6 siRNA (0.3 mg/kg). Mice were euthanized at 48 hrs post siRNA administration. Whole blood was collected and assayed for hematological parameters. As shown in FIG. 2, treatment with an ALK2 antibody prevents the hemoglobin reduction associated with TMPRSS6 deficiency (*=p≤0.05; **=p≤0.01).

Figure 3A:
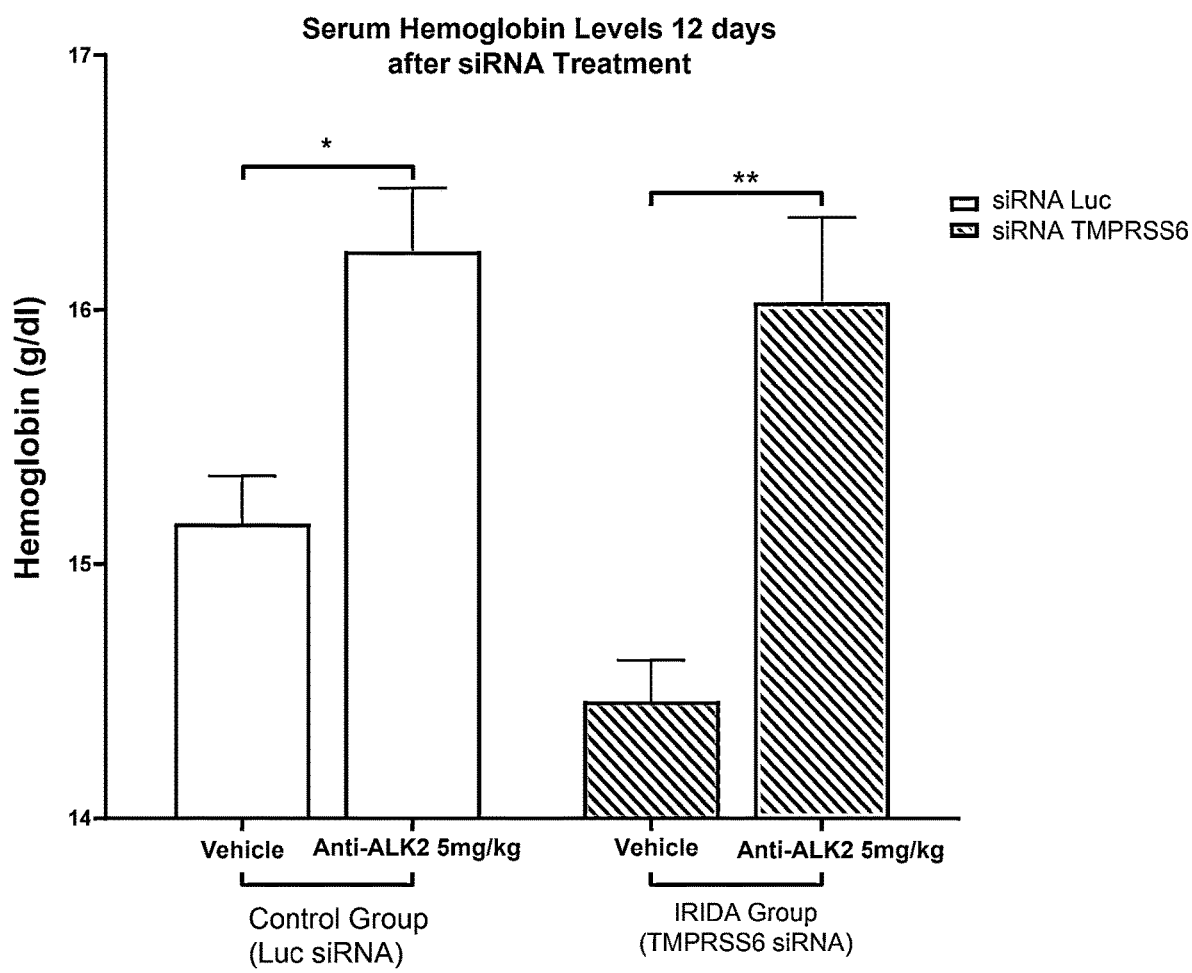
FIGS. 3A-3C are a series of graphs showing the effect of treatment with an ALK2 antibody on hemoglobin levels, hepcidin concentration, and iron levels in a mouse model of IRIDA. Treatment with an ALK2 antibody reverses the hemoglobin reduction associated with TMPRSS6 deficiency (*=p≤0.05; =p≤0.01, FIG. 3A), the increased serum hepcidin associated with TMPRSS6 deficiency (=p≤0.01, FIG. 3B), and the decreased serum iron associated with TMPRSS6 deficiency (*=p≤0.05; **=p≤0.01).
Figure 3B:
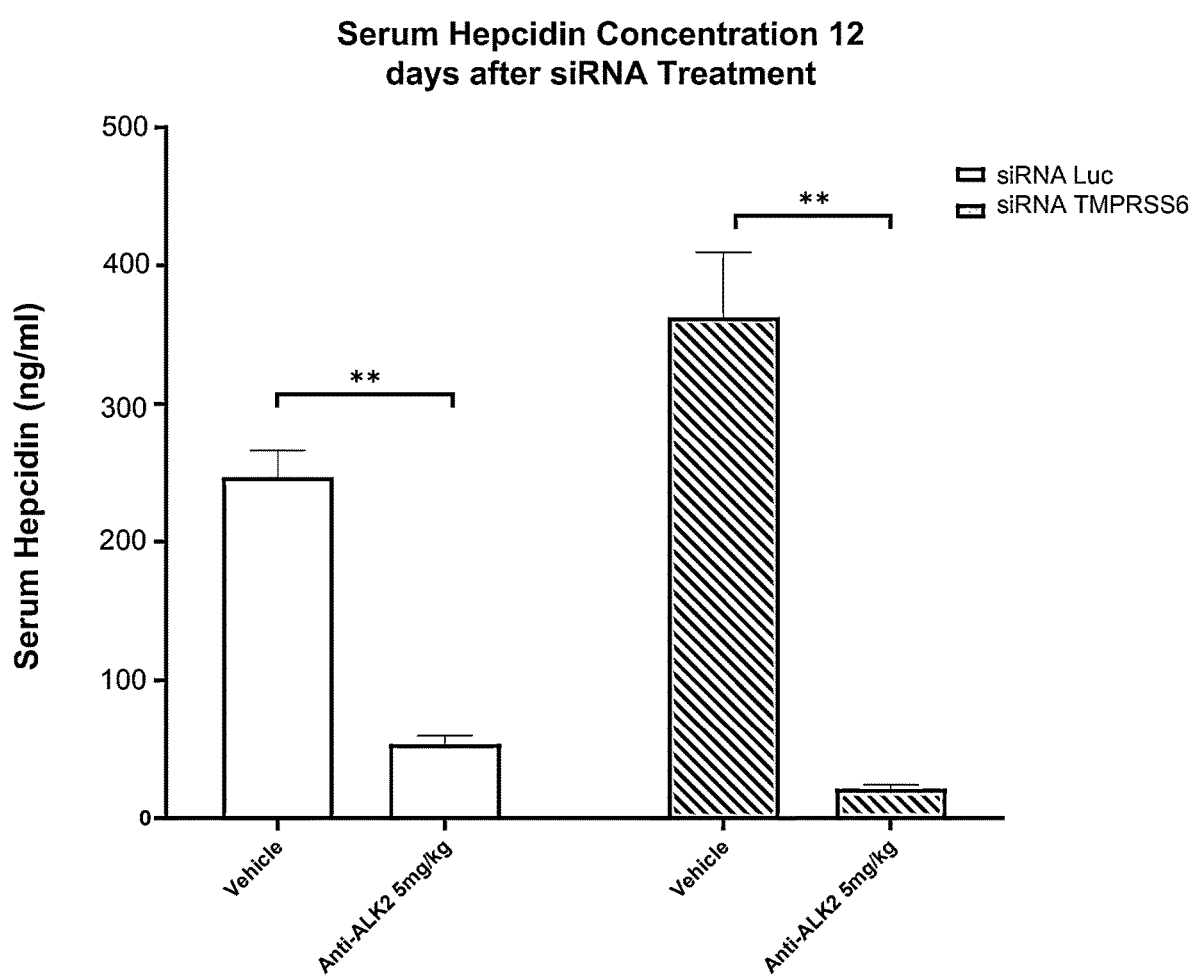
Figure 3C:
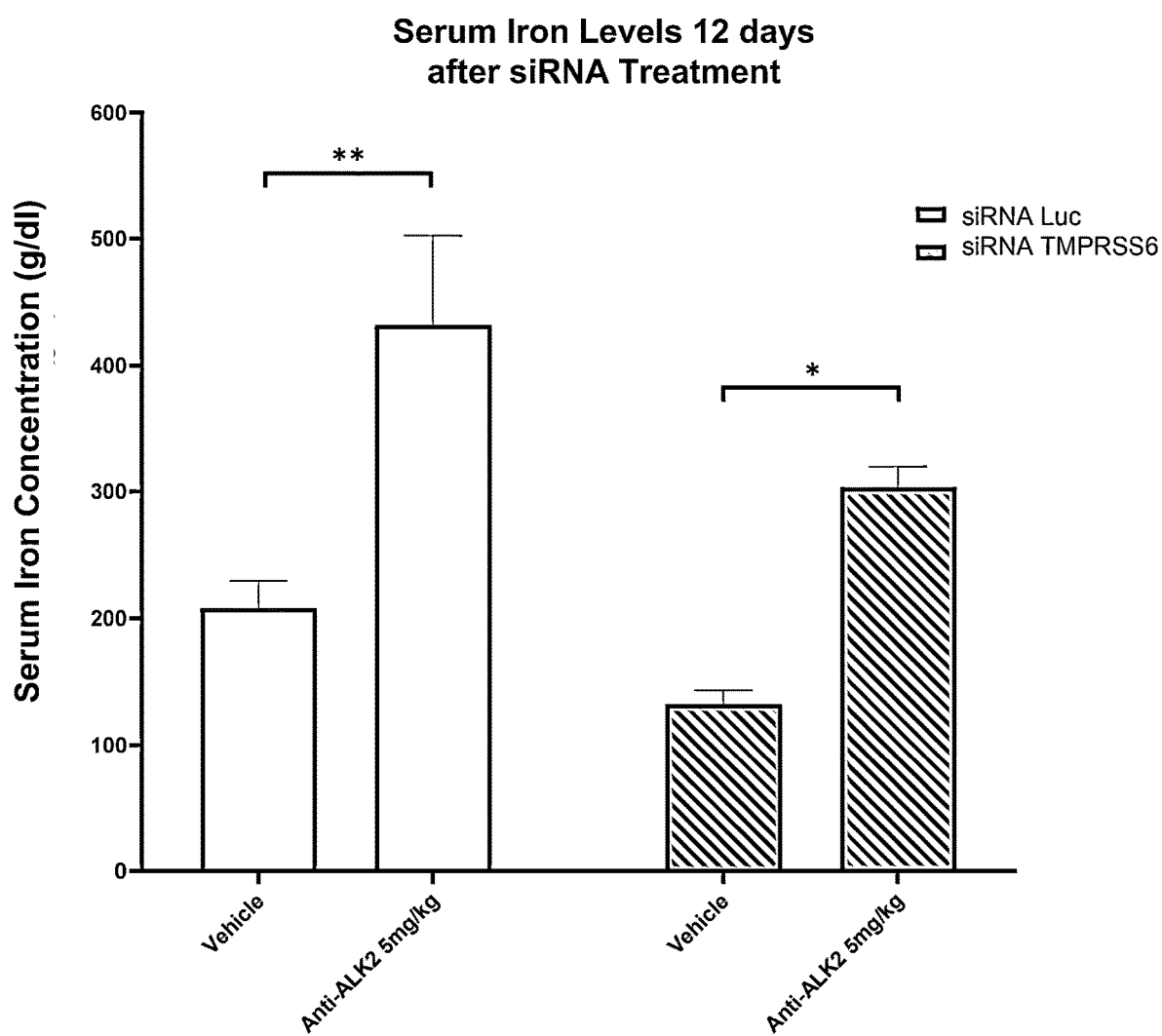

In a second experiment, eight-week old, female albino C57BL/6 mice were dosed intravenously every three days with a lipid encapsulated siRNA targeted against either Luciferase (control) or TMPRSS6 (0.75 mg/kg). Mice received siRNA treatment until the point that the cohort receiving TMPRSS6 siRNA had increased hepcidin and decreased serum hemoglobin and serum iron. At this point, mice were further randomized to receive either vehicle or an anti-ALK2 antibody (Antibody 2, 5 mg/kg, intraperitoneal administration). Mice were euthanized at 12 days after their first siRNA administration. Whole blood was collected and assayed for hematological parameters. Additionally, serum was collected and assayed for hepcidin concentration by ELISA and total iron content by colorimetric assay. As shown in FIG. 3A, treatment with the ALK2 antibody reversed the hemoglobin reduction associated with TMPRSS6 deficiency (*=p≤0.05; =p≤0.01). ALK2 antibody treatment also reversed the increased serum hepcidin associated with TMPRSS6 deficiency (=p≤0.01, FIG. 3B) and the decreased serum iron associated with TMPRSS6 deficiency (*=p≤0.05; **=p≤0.01, FIG. 3C).

Example 5—Effect of ALK2 Antibody in a Mouse Model of Osteoporosis

Figure 4:
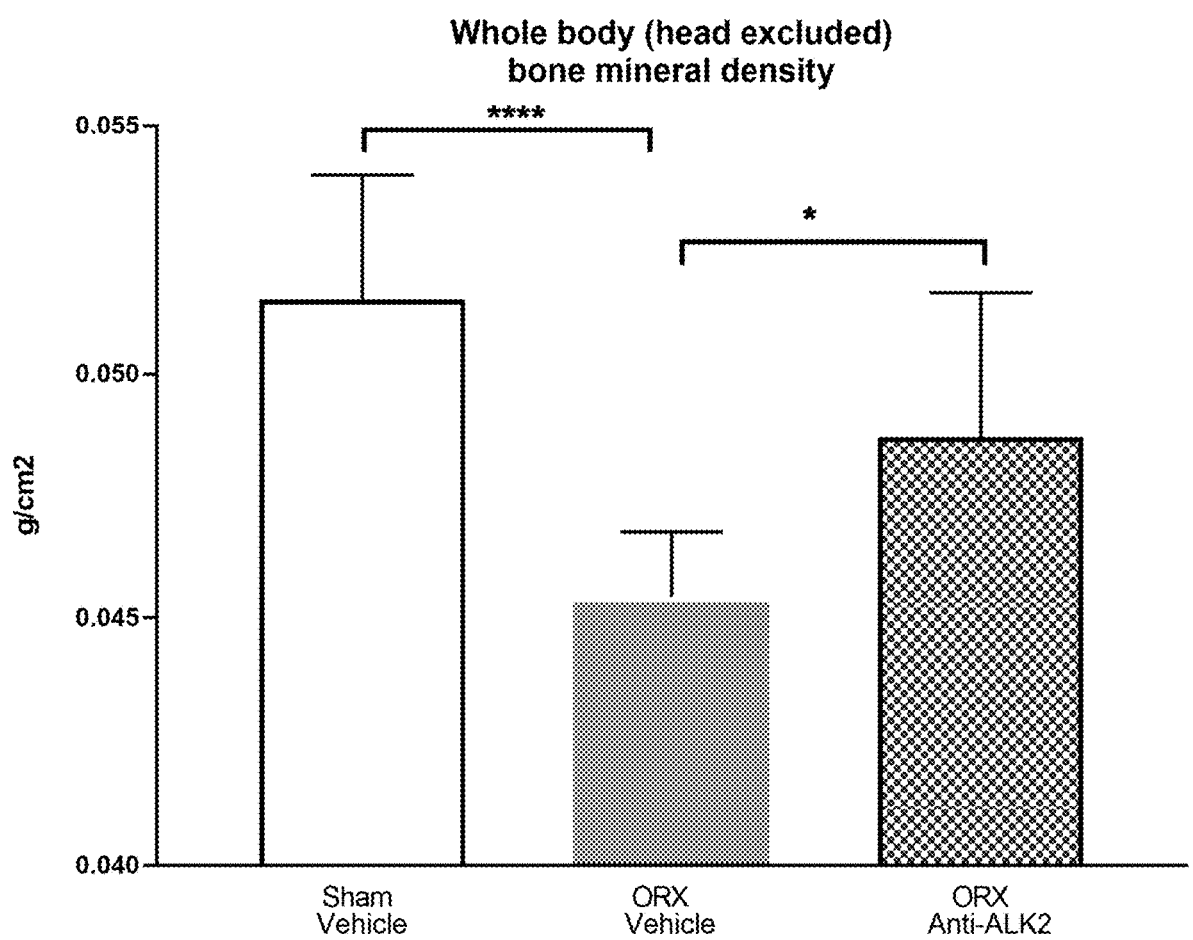
FIG. 4 is a graph showing the effect of treatment with an ALK2 antibody on bone mineral density in a mouse model of osteoporosis. Treatment with an ALK2 antibody increases bone mineral density (reduces bone loss) associated with orchiectomy (*=p≤0.05; ****=p≤0.0001).

C57BL/6 mice received orchiectomy (ORX) or sham surgery at nine weeks of age. Following a six-week recovery period, during which time the ORX mice developed an osteoporotic phenotype, ORX mice received intraperitoneal injections twice weekly of either vehicle or ALK2 antibody (5 mg/kg Antibody 2). Whole body dual X-ray absorptiometry (Lunar PIXImus, GE Lunar Corp.) was performed 16 weeks after dosing was initiated. A high-resolution digital picture was captured and referenced against a hydroxyapatite phantom to determine BMD (software version 2.10). As shown in FIG. 4, ORX mice treated with an ALK2 antibody had a greater BMD than vehicle treated mice, indicating that treatment with an ALK2 antibody improves BMD or reduces bone loss.

Example 6—Effect of ALK2 Antibody in a Mouse Model of MO

The effect of an ALK2 antibody on the formation of osteochondromas is determined using a mouse model of MO. This mouse has an inducible, chondrocyte-specific, homozygous disruption of the Ext1 gene and, after a single dose of doxycycline is administered to the lactating dam at P8, osteochondroma formation is observed in 100% of mutants. Mice are divided into two groups receiving twice-weekly intraperitoneal injections of either ALK2 antibody (5 mg/kg) or vehicle beginning at P8. Micro-CT imaging is performed weekly to monitor for osteochondromas at the knee joint and ribcage. Mice are sacrificed at the end of four weeks of treatment. In a subset of each group, skeletons are whole-mount prepared and stained with Alizarin red and Alcian blue for imaging purposes. In the remaining mice, the hindlimbs and samples of the chondro-osseous junction of the ribcage are harvested. The tissues are fixed in 4% paraformaldehyde, decalcified in EDTA, embedded in paraffin, and sectioned at 5 μm thickness. Safarin O/Fast Green staining is then used to determine alterations in cartilage morphology as well as the development of osteochondromas.

Example 7—Effect of ALK2 Antibody on Posterior Capsule Opacification

The effect of an ALK2 antibody on the formation of posterior capsule opacification (PCO) following cataract surgery is determined using a mouse model of injury-induced PCO. Briefly, ten- to sixteen-week-old mice are separated into two groups receiving either an ALK2 antibody (5 mg/kg) or vehicle twice-weekly for two weeks prior to surgery. Cataract surgery is performed under anesthesia and one of the pupils is dilated with 2.5% phenylephrine hydrochloride and 1% tropicamide. Using an ophthalmic scalpel, an incision is made in the central cornea extending into the lens capsule. Hydrodissection with balanced salt solution is used to separate the lens fiber mass from the lens capsule, the lens fiber mass is removed, the incision is closed and the anterior chamber is refilled with balanced salt solution. In each group, subsets of mice are euthanized immediately after surgery and at 1, 5, and 14 days after surgery. Mice continue to receive either ALK2 antibody or vehicle twice-weekly until they are euthanized. Immediately before dissection, animals are anesthetized, and the presence or absence of opacification of the cornea, neovascularization, and degree of pupil dilation is assessed. At dissection, both surgical and non-surgical eyes (control) are harvested and embedded, snap frozen and stored at −80° C. The degree of presence of inflammatory cells, fibrotic markers (aSMA, fibronectin) and lens fiber differentiation markers (Prox1, cMaf) are then evaluated using immunohistochemistry.

Example 8—Effect of ALK2 Antibody in a Murine Orthotopic Xenograft Model of DIPG The effect of an ALK2 antibody on inhibiting the growth of gliomas in diffuse intrinsic pontine glioma (DIPG) is assessed using a murine orthotopic xenograft model of DIPG. This model incorporates the transplantation of a patient derived cell line (HSJD-DIPG-007), containing mutations in the HK27M and ACRV1 genes, into the $4^{th}$ cerebral ventricle of immune deficient NOD-SCID mice. The primary outcome of the studies is the duration of the survival of the pups receiving transplantation. Briefly, 3-week old, female NOD-SCID mice are transplanted with HSJD-DIPG-007 cells via stereotactic surgery. Fourteen to twenty-one days post-inoculation the mice are randomized into two groups and administered either vehicle or ALK2 antibody (5 mg/kg) twice weekly. Mice are expected to become symptomatic within 21 days of inoculation, and without intervention, are expected to have an average lifespan of ~60 days. Over the duration of the study period, mice are monitored closely for body weight, health, and condition. Mice are euthanized and removed from the study if they lose more than 20% in body weight or show signs of poor health and distress. Post-termination, the brains of the mice are carefully dissected and fixed in formalin for future histological assessment and to determine the in vivo growth of the HSJD-DIPG-007 cells.

Example 9—Effect of ALK2 Antibody in a Murine Model of Sjogren's Syndrome

The effect of an ALK2 antibody on ameliorating symptoms of Sjogren's syndrome is determined in the non-obese diabetic (NOD) autoimmune mouse model. In addition to insulitis, the NOD mice develop immune infiltrates in the exocrine lacrimal and salivary glands leading to eventual secretory dysfunction. The primary phenotypic outcome measured in these mice is tear volume production. This is tested weekly to give a longitudinal analysis of the progression of disease and the efficacy of pharmacologic intervention. The antibody is dosed at 5 mg/kg twice weekly via intraperitoneal injections. Briefly, NOD mice (12 weeks of age) are assessed for tear production at baseline, then randomized into two groups to receive either vehicle or ALK2 antibody for 8 weeks. Throughout this duration, mice are tested weekly for tear production. At the termination of the study, lacrimal glands are harvested to assess mRNA expression of fibrotic (MMP9, MMP2, COL1A1, TIMP) and inflammatory (MCP1, IL6, TNF-alpha) markers. Contralateral lacrimal glands are dissected and fixed in formalin for histological analyses of inflammation and fibrosis.

Example 10—Effect of ALK2 Antibody in a Murine Model of Cardiac Hypertrophy

The effect of an ALK2 antibody on the development of cardiac hypertrophy and fibrosis is determined using the angiotensin II (A2)-induced cardiac hypertrophy mouse model. Mice are separated into groups receiving either an ALK2 antibody (5 mg/kg) or vehicle twice-weekly for either two weeks prior to surgery or groups that will begin dosing immediately post-surgery. Briefly, anesthetized mice are implanted with A2-filled osmotic minipumps which release a constant dose of A2 for two or four weeks to induce cardiac hypertrophy. At the end of two or four weeks, mice undergo echocardiographic analysis under sedation. The whole heart and left ventricle (LV) are weighed and the LV is divided in half and saved in liquid nitrogen or formalin. Tibial length (TL) is also determined. Changes in heart weight, the ratio of heart weight to TL ratio, LV weight, and the LV to TL ratio are assessed. Additionally, intraventricular septum and posterior wall thickness and cardiomyocyte area and fibrosis are determined.

Example 11—Treatment of Anemia by Administration of an ALK2 Antibody

According to the methods disclosed herein, a physician of skill in the art can treat a subject, such as a human patient, having anemia (e.g., IRIDA or anemia of inflammation) so as to increase hemoglobin levels, increase red blood cell counts, or reduce iron deficiency. The method of treatment can include diagnosing or identifying a subject as a candidate for treatment based on a blood test measuring hematological parameters. To treat the subject, a physician of kill in the art can administer to the subject a composition containing an ALK2 antibody or an antigen binding fragment thereof (e.g., an ALK2 binding fragment). The composition containing the ALK2 antibody or an antigen binding fragment thereof (e.g., an ALK2 binding fragment) may be administered to the subject, for example, by parenteral injection (e.g., intravenous injection) to treat anemia. The ALK2 antibody or an antigen binding fragment thereof (e.g., an ALK2 binding fragment) is administered in a therapeutically effective amount, such as from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg). In some embodiments, the ALK2 antibody or an antigen binding fragment thereof (e.g., an ALK2 binding fragment) is administered bimonthly, once a month, once every two weeks, or at least once a week or more (e.g., 1, 2, 3, 4, 5, 6, or 7 times a week or more). The ALK2 antibody or an antigen binding fragment thereof (e.g., an ALK2 binding fragment) is administered in an amount sufficient to increase hemoglobin levels, increase red blood cell counts, or reduce iron deficiency.

Following administration of the composition to a patient, a practitioner of skill in the art can monitor the patient's improvement in response to the therapy by a variety of methods. For example, a physician can monitor the patient's hemoglobin levels, red blood cell counts, or iron deficiency by performing a blood test. A finding that the patient exhibits improved hemoglobin levels, red blood cell counts, or iron deficiency following administration of the composition compared to test results prior to administration of the composition indicates that the patient is responding favorably to the treatment. Subsequent doses can be determined and administered as needed.

Example 12—Treatment of Bone Disease by Administration of an ALK2 Antibody

According to the methods disclosed herein, a physician of skill in the art can treat a subject, such as a human patient, having bone disease (e.g., osteoporosis or osteopenia) so as to increase bone mineral density, increase bone formation, reduce bone resorption (e.g., bone loss), or reduce the risk of bone fracture. The method of treatment can include diagnosing or identifying a subject as a candidate for treatment based on standard clinical tests for bone mineral density (e.g., dual X-ray absorptiometry). To treat the subject, a physician of kill in the art can administer to the subject a composition containing an ALK2 antibody or an antigen binding fragment thereof (e.g., an ALK2 binding fragment). The composition containing the ALK2 antibody or an antigen binding fragment thereof (e.g., an ALK2 binding fragment) may be administered to the subject, for example, by parenteral injection (e.g., intravenous injection) to treat bone disease. The ALK2 antibody or an antigen binding fragment thereof (e.g., an ALK2 binding fragment) is administered in a therapeutically effective amount, such as from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg). In some embodiments, the ALK2 antibody or an antigen binding fragment thereof (e.g., an ALK2 binding fragment) is administered bimonthly, once a month, once every two weeks, or at least once a week or more (e.g., 1, 2, 3, 4, 5, 6, or 7 times a week or more). The ALK2 antibody or an antigen binding fragment thereof (e.g., an ALK2 binding fragment) is administered in an amount sufficient to increase bone mineral density, increase bone formation, reduce bone resorption (e.g., bone loss), or reduce the risk of bone fracture.

Following administration of the composition to a patient, a practitioner of skill in the art can monitor the patient's improvement in response to the therapy by a variety of methods. For example, a physician can monitor the patient's bone mineral density by performing dual X-ray absorptiometry. A finding that the patient exhibits increased bone mineral density, increased bone formation, reduced bone resorption (e.g., bone loss), or a reduced risk of bone fracture following administration of the composition compared to test results prior to administration of the composition indicates that the patient is responding favorably to the treatment. Subsequent doses can be determined and administered as needed.

Example 13—Treatment of FOP by Administration of an ALK2 Antibody

According to the methods disclosed herein, a physician of skill in the art can treat a subject, such as a human patient, having FOP (e.g., a patient with a gain of function mutation in ALK2) so as to prevent or reduce heterotopic ossification, slow the progression of FOP, or delay the onset of FOP. The method of treatment can include diagnosing or identifying a subject as a candidate for treatment based on genetic testing for a mutation in ALK2 or performing radiographic imaging, a CT, or an MRI. To treat the subject, a physician of kill in the art can administer to the subject a composition containing an ALK2 antibody or an antigen binding fragment thereof (e.g., an ALK2 binding fragment). The composition containing the ALK2 antibody or an antigen binding fragment thereof (e.g., an ALK2 binding fragment) may be administered to the subject, for example, by parenteral injection (e.g., intravenous injection) to treat FOP. The ALK2 antibody or an antigen binding fragment thereof (e.g., an ALK2 binding fragment) is administered in a therapeutically effective amount, such as from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg). In some embodiments, the ALK2 antibody or an antigen binding fragment thereof (e.g., an ALK2 binding fragment) is administered bimonthly, once a month, once every two weeks, or at least once a week or more (e.g., 1, 2, 3, 4, 5, 6, or 7 times a week or more). The ALK2 antibody or an antigen binding fragment thereof (e.g., an ALK2 binding fragment) is administered in an amount sufficient to reduce heterotopic ossification, slow the progression of FOP, or delay the onset of FOP.

Following administration of the composition to a patient, a practitioner of skill in the art can monitor the patient's improvement in response to the therapy by a variety of methods. For example, a physician can monitor the patient's heterotopic ossification or disease progression using radiography, CT, and/or MRI. A finding that the patient exhibits reduced heterotopic ossification (e.g., a reduction in the amount of heterotopic ossification or the formation of additional heterotopic bone), a failure to develop heterotopic ossification, or delayed onset or slowed progression of FOP following administration of the composition compared to test results prior to administration of the composition or compared to an untreated subject indicates that the patient is responding favorably to the treatment. Subsequent doses can be determined and administered as needed.

Example 14—Treatment of Sjogren's Syndrome by Administration of an ALK2 Antibody According to the methods disclosed herein, a physician of skill in the art can treat a subject, such as a human patient, having Sjogren's syndrome so as to ameliorate or reduce one or more symptom of Sjogren's syndrome (e.g., dry eye, dry mouth, eye irritation, blurred vision, lacrimal gland fibrosis, lacrimal gland inflammation, joint pain, or fatigue). To treat the subject, a physician of kill in the art can administer to the subject a composition containing an ALK2 antibody or an antigen binding fragment thereof (e.g., an ALK2 binding fragment). The composition containing the ALK2 antibody or an antigen binding fragment thereof (e.g., an ALK2 binding fragment) may be administered to the subject, for example, by parenteral injection (e.g., intravenous injection) to treat Sjogren's syndrome. The ALK2 antibody or an antigen binding fragment thereof (e.g., an ALK2 binding fragment) is administered in a therapeutically effective amount, such as from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg). In some embodiments, the ALK2 antibody or an antigen binding fragment thereof (e.g., an ALK2 binding fragment) is administered bimonthly, once a month, once every two weeks, or at least once a week or more (e.g., 1, 2, 3, 4, 5, 6, or 7 times a week or more). The ALK2 antibody or an antigen binding fragment thereof (e.g., an ALK2 binding fragment) is administered in an amount sufficient to ameliorate or reduce one or more symptom of Sjogren's syndrome (e.g., dry eye, dry mouth, eye irritation, blurred vision, lacrimal gland fibrosis, lacrimal gland inflammation, joint pain, or fatigue, e.g., by increasing the production of tears or saliva).

Following administration of the composition to a patient, a practitioner of skill in the art can monitor the patient's improvement in response to the therapy by a variety of methods. For example, a physician can monitor the patient's symptoms of Sjogren's syndrome by evaluating the production of tears (e.g., tear volume production), the production of saliva, vision, eye irritation, inflammation or fibrosis of the lacrimal gland, or the patient's reports of joint pain or fatigue. A finding that the patient exhibits a reduction in one or more symptom of Sjogren's syndrome (e.g., dry eye, dry mouth, eye irritation, blurred vision, lacrimal gland fibrosis, lacrimal gland inflammation, joint pain, or fatigue) following administration of the composition compared to the symptom prior to administration of the composition or compared to an untreated subject indicates that the patient is responding favorably to the treatment. Subsequent doses can be determined and administered as needed.

Example 15—Treatment of MO by Administration of an ALK2 Antibody

According to the methods disclosed herein, a physician of skill in the art can treat a subject, such as a human patient, having MO so as to prevent or reduce the formation of an osteochondroma, reduce the size of an osteochondroma, reduce the number of osteochondromas, or slow the growth of an osteochondroma. The method of treatment can include diagnosing or identifying a subject as a candidate for treatment based on genetic testing for a mutation in EXT1 or EXT2 or performing radiographic imaging, a CT, or an MRI. To treat the subject, a physician of kill in the art can administer to the subject a composition containing an ALK2 antibody or an antigen binding fragment thereof (e.g., an ALK2 binding fragment). The composition containing the ALK2 antibody or an antigen binding fragment thereof (e.g., an ALK2 binding fragment) may be administered to the subject, for example, by parenteral injection (e.g., intravenous injection) to treat MO. The ALK2 antibody or an antigen binding fragment thereof (e.g., an ALK2 binding fragment) is administered in a therapeutically effective amount, such as from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg). In some embodiments, the ALK2 antibody or an antigen binding fragment thereof (e.g., an ALK2 binding fragment) is administered bimonthly, once a month, once every two weeks, or at least once a week or more (e.g., 1, 2, 3, 4, 5, 6, or 7 times a week or more). The ALK2 antibody or an antigen binding fragment thereof (e.g., an ALK2 binding fragment) is administered in an amount sufficient to reduce the formation of an osteochondroma, reduce the size of an osteochondroma, reduce the number of osteochondromas, or slow the growth of an osteochondroma.

Following administration of the composition to a patient, a practitioner of skill in the art can monitor the patient's improvement in response to the therapy by a variety of methods. For example, a physician can monitor the growth, number, or size of osteochondromas in the patient using radiography, CT, and/or MRI. A finding that the patient exhibits reduced osteochondroma formation (e.g., does not form new osteochondromas or forms fewer osteochondromas compared to an untreated subject or osteochondroma formation prior to treatment), reduced osteochondroma size, reduced osteochondroma number, or slower osteochondroma growth following administration of the composition compared to test results prior to administration of the composition or compared to an untreated subject indicates that the patient is responding favorably to the treatment. Subsequent doses can be determined and administered as needed.

Example 16—Treatment of DIPG by Administration of an ALK2 Antibody

According to the methods disclosed herein, a physician of skill in the art can treat a subject, such as a human patient, having DIPG so as to improve survival time, reduce tumor growth, reduce tumor size or volume, or prevent or reduce tumor metastasis. The method of treatment can include diagnosing or identifying a subject as a candidate for treatment based on genetic testing for an activating mutation in ALK2. To treat the subject, a physician of kill in the art can administer to the subject a composition containing an ALK2 antibody or an antigen binding fragment thereof (e.g., an ALK2 binding fragment). The composition containing the ALK2 antibody or an antigen binding fragment thereof (e.g., an ALK2 binding fragment) may be administered to the subject, for example, by parenteral injection (e.g., intravenous injection) or by local administration to the central nervous system (e.g., intracerebroventricular injection, intrathecal injection, or intra-cisternal injection). The ALK2 antibody or an antigen binding fragment thereof (e.g., an ALK2 binding fragment) is administered in a therapeutically effective amount, such as from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg). In some embodiments, the ALK2 antibody or an antigen binding fragment thereof (e.g., an ALK2 binding fragment) is administered bimonthly, once a month, once every two weeks, or at least once a week or more (e.g., 1, 2, 3, 4, 5, 6, or 7 times a week or more). The ALK2 antibody or an antigen binding fragment thereof (e.g., an ALK2 binding fragment) is administered in an amount sufficient to improve survival time, reduce tumor growth, reduce tumor size or volume, or prevent or reduce tumor metastasis.

Following administration of the composition to a patient, a practitioner of skill in the art can monitor the patient's improvement in response to the therapy by a variety of methods. For example, a physician can monitor the patient's survival time or tumor size, growth, or metastasis using imaging (e.g., MRI). A finding that the patient exhibits reduced tumor growth, reduced tumor size or volume, reduced tumor metastasis, or increased survival time compared to an untreated subject or compared to tumor growth, size, or metastasis in the subject prior to administration indicates that the patient is responding favorably to the treatment. Subsequent doses can be determined and administered as needed.

Example 17—Treatment or Prevention of PCO by Administration of an ALK2 Antibody

According to the methods disclosed herein, a physician of skill in the art can treat a subject, such as a human patient, having or at risk of developing PCO (e.g., a patient having PCO or a patient that has undergone cataract surgery or is soon to undergo cataract surgery, e.g., a patient that will undergo cataract surgery in 6 months, 5 months, 4 months, 3 months, 2 months, 1 month, 2 weeks, 1 week, or less) so as to prevent the development of PCO, reduce PCO, improve visual acuity (e.g., reduce blurry or cloudy vision), reduce light sensitivity or glare, reduce or prevent fibrosis (e.g., fibrosis on or near the posterior capsule, e.g., near the implanted lens), reduce or prevent lens fiber differentiation, reduce or inhibit lens epithelial cell proliferation, or reduce or prevent inflammation in the eye. To treat the subject, a physician of kill in the art can administer to the subject a composition containing an ALK2 antibody or an antigen binding fragment thereof (e.g., an ALK2 binding fragment). The composition containing the ALK2 antibody or an antigen binding fragment thereof (e.g., an ALK2 binding fragment) may be administered to the subject, for example, by parenteral injection (e.g., intravenous injection) or by administration to the eye (e.g., intraocular injection or topical administration) to treat PCO. The ALK2 antibody or an antigen binding fragment thereof (e.g., an ALK2 binding fragment) is administered in a therapeutically effective amount, such as from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg). In some embodiments, the ALK2 antibody or an antigen binding fragment thereof (e.g., an ALK2 binding fragment) is administered bimonthly, once a month, once every two weeks, or at least once a week or more (e.g., 1, 2, 3, 4, 5, 6, or 7 times a week or more). The ALK2 antibody or an antigen binding fragment thereof (e.g., an ALK2 binding fragment) is administered in an amount sufficient to prevent the development of PCO, reduce PCO, improve visual acuity (e.g., reduce blurry or cloudy vision), reduce light sensitivity or glare, reduce or prevent fibrosis (e.g., fibrosis on or near the posterior capsule, e.g., near the implanted lens), reduce or prevent lens fiber differentiation, reduce or inhibit lens epithelial cell proliferation, or reduce or prevent inflammation in the eye.

Following administration of the composition to a patient, a practitioner of skill in the art can monitor the patient's improvement in response to the therapy by a variety of methods. For example, a physician can monitor the patient's visual acuity, sensitivity to light or glare, opacity of the posterior capsule, or eye inflammation. A finding that the patient does not develop PCO or exhibits improved visual acuity, reduced sensitivity to light or glare, reduced fibrosis, or reduced inflammation in the eye following administration of the composition compared to an untreated subject or compared to measurements from the patient prior to treatment indicates that the patient is responding favorably to the treatment. Subsequent doses can be determined and administered as needed.

Example 18—Treatment of Cardiac Hypertrophy and/or Cardiac Fibrosis by Administration of an ALK2 Antibody According to the methods disclosed herein, a physician of skill in the art can treat a subject, such as a human patient, having cardiac hypertrophy and/or cardiac fibrosis so as to slow or prevent the development of cardiac hypertrophy or cardiac fibrosis, reverse cardiac fibrosis, reduce or inhibit cardiac scar formation, increase or induce cardiac regeneration, or improve one or more symptoms of cardiac hypertrophy or cardiac fibrosis (e.g., increase exercise capacity, increase blood ejection volume, reduce left ventricular end diastolic pressure, reduce pulmonary capillary wedge pressure, increase cardiac output, increase cardiac index, reduce pulmonary artery pressures, reduce left ventricular end systolic and diastolic dimensions, reduce left and right ventricular wall stress, reduce wall tension and/or wall thickness, increase myocardial contractility, reduce extracellular matrix deposition in the cardiac muscle, or reduce fibrosis). To treat the subject, a physician of kill in the art can administer to the subject a composition containing an ALK2 antibody or an antigen binding fragment thereof (e.g., an ALK2 binding fragment). The composition containing the ALK2 antibody or an antigen binding fragment thereof (e.g., an ALK2 binding fragment) may be administered to the subject, for example, by parenteral injection (e.g., intravenous injection) to treat cardiac hypertrophy and/or cardiac fibrosis. The ALK2 antibody or an antigen binding fragment thereof (e.g., an ALK2 binding fragment) is administered in a therapeutically effective amount, such as from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg). In some embodiments, the ALK2 antibody or an antigen binding fragment thereof (e.g., an ALK2 binding fragment) is administered bimonthly, once a month, once every two weeks, or at least once a week or more (e.g., 1, 2, 3, 4, 5, 6, or 7 times a week or more). The ALK2 antibody or an antigen binding fragment thereof (e.g., an ALK2 binding fragment) is administered in an amount sufficient to slow or prevent the development of cardiac hypertrophy or cardiac fibrosis, reverse cardiac fibrosis, reduce or inhibit cardiac scar formation, increase or induce cardiac regeneration, or improve one or more symptoms of cardiac hypertrophy or cardiac fibrosis (e.g., increase exercise capacity, increase blood ejection volume, reduce left ventricular end diastolic pressure, reduce pulmonary capillary wedge pressure, increase cardiac output, increase cardiac index, reduce pulmonary artery pressures, reduce left ventricular end systolic and diastolic dimensions, reduce left and right ventricular wall stress, reduce wall tension and/or wall thickness, increase myocardial contractility, reduce extracellular matrix deposition in the cardiac muscle, or reduce fibrosis).

Following administration of the composition to a patient, a practitioner of skill in the art can monitor the patient's improvement in response to the therapy by a variety of methods. For example, a physician can monitor the patient's symptoms of cardiac hypertrophy or cardiac fibrosis (e.g., exercise capacity, blood ejection volume, left ventricular end diastolic pressure, pulmonary capillary wedge pressure, cardiac output, cardiac index, pulmonary artery pressures, left ventricular end systolic and diastolic dimensions, left and right ventricular wall stress, wall tension and/or wall thickness, or myocardial contractility) using a stress test, echocardiogram, MRI, or other approaches. A finding that the patient exhibits reduced cardiac fibrosis, increased cardiac regeneration, or an improvement of one or more symptoms of cardiac hypertrophy or cardiac fibrosis (e.g., increase exercise capacity, increase blood ejection volume, reduce left ventricular end diastolic pressure, reduce pulmonary capillary wedge pressure, increase cardiac output, increase cardiac index, reduce pulmonary artery pressures, reduce left ventricular end systolic and diastolic dimensions, reduce left and right ventricular wall stress, reduce wall tension and/or wall thickness, increase myocardial contractility, reduce extracellular matrix deposition in the cardiac muscle, or reduce fibrosis) following administration of the composition compared to test results prior to administration of the composition or compared to an untreated subject indicates that the patient is responding favorably to the treatment. Subsequent doses can be determined and administered as needed.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety.

Other embodiments are within the following claims.

The invention claimed is:

1. An isolated ALK2 antibody, or an antigen binding fragment thereof, comprising:
   (a) a light chain complementarity determining region (CDR) 1 comprising the amino acid sequence SGSSSNIGSNYVS (SEQ ID NO: 1); a light chain CDR2 comprising the amino acid sequence VLIYKNNHRPS (SEQ ID NO: 24); a light chain CDR3 comprising the amino acid sequence ASWDHSDRFYV (SEQ ID NO: 4); a heavy chain CDR1 comprising the amino acid sequence GGTFSSYGVS (SEQ ID NO: 31); a heavy chain CDR2 comprising the amino acid sequence WMGGIIPHFGIANYAQKFQG (SEQ ID NO: 36); and a heavy chain CDR3 comprising the amino acid sequence EIGSLDI (SEQ ID NO: 13);
   (b) a light chain CDR1 comprising the amino acid sequence SGDSIPSFFAS (SEQ ID NO: 18); a light chain CDR2 comprising the amino acid sequence LVIYRDSNRPS (SEQ ID NO: 25); a light chain CDR3 comprising the amino acid sequence YVTAPWKSIW (SEQ ID NO: 5); a heavy chain CDR1 comprising the amino acid sequence GFTFSSHAMS (SEQ ID NO: 32); a heavy chain CDR2 comprising the amino acid sequence WVGRIKSKADSGTTDYAAPVKG (SEQ ID NO: 37); and a heavy chain CDR3 comprising the amino acid sequence DYGVAFAY (SEQ ID NO: 14);
   (c) a light chain CDR1 comprising the amino acid sequence SGDNIGTKYAY (SEQ ID NO: 19); a light chain CDR2 comprising the amino acid sequence LVIYGDSDRPS (SEQ ID NO: 26); a light chain CDR3 comprising the amino acid sequence YSADAQQMKA (SEQ ID NO: 6); a heavy chain CDR1 comprising the amino acid sequence GFTFNSSAMS (SEQ ID NO: 33); a heavy chain CDR2 comprising the amino acid sequence WVGRIKSKRDGYTTDYAAPVKG (SEQ ID NO: 38); and a heavy chain CDR3 comprising the amino acid sequence DYGGLKFDY (SEQ ID NO: 15);

(d) a light chain CDR1 comprising the amino acid sequence SGDNLRKYSAH (SEQ ID NO: 20); a light chain CDR2 comprising the amino acid sequence LVIYYDNKRPS (SEQ ID NO: 27); a light chain CDR3 comprising the amino acid sequence QVYASVHRM (SEQ ID NO: 7); a heavy chain CDR1 comprising the amino acid sequence GGTFSSYAIH (SEQ ID NO: 34); a heavy chain CDR2 comprising the amino acid sequence WMGRIIPDFGTANYAQKFQG (SEQ ID NO: 39); and a heavy chain CDR3 comprising the amino acid sequence GPTQAIHYFAY (SEQ ID NO: 16); or (e) a light chain CDR1 comprising the amino acid sequence SGDSLGSKSVH (SEQ ID NO: 21); a light chain CDR2 comprising the amino acid sequence LVIYRDSKRPS (SEQ ID NO: 28); a light chain CDR3 comprising the amino acid sequence QTYDWSHFGW (SEQ ID NO: 8); a heavy chain CDR1 comprising the amino acid sequence GFTFSSAAMH (SEQ ID NO: 35); a heavy chain CDR2 comprising the amino acid sequence WVSVISSDGGSTYYADSVKG (SEQ ID NO: 12); and a heavy chain CDR3 comprising the amino acid sequence AGFILGSLGVAWMDV (SEQ ID NO: 17).

2. The isolated ALK2 antibody, or antigen binding fragment thereof, of claim 1, wherein the light chain CDR1 comprises the amino acid sequence SGSSSNIGSNYVS (SEQ ID NO: 1); the light chain CDR2 comprises the amino acid sequence VLIYKNNHRPS (SEQ ID NO: 24); the light chain CDR3 comprises the amino acid sequence ASWDHSDRFYV (SEQ ID NO: 4); the heavy chain CDR1 comprises the amino acid sequence GGTFSSYGVS (SEQ ID NO: 31); the heavy chain CDR2 comprises the amino acid sequence WMGGIIPHFGIANYAQKFQG (SEQ ID NO: 36); and the heavy chain CDR3 comprises the amino acid sequence EIGSLDI (SEQ ID NO: 13).

3. The isolated ALK2 antibody, or antigen binding fragment thereof, of claim 1, wherein the light chain CDR1 comprises the amino acid sequence SGDSIPSFFAS (SEQ ID NO: 18); the light chain CDR2 comprises the amino acid sequence LVIYRDSNRPS (SEQ ID NO: 25); the light chain CDR3 comprises the amino acid sequence YVTAPWKSIW (SEQ ID NO: 5); the heavy chain CDR1 comprises the amino acid sequence GFTFSSHAMS (SEQ ID NO: 32); the heavy chain CDR2 comprises the amino acid sequence WVGRIKSKADSGTTDYAAPVKG (SEQ ID NO: 37); and the heavy chain CDR3 comprises the amino acid sequence DYGVAFAY (SEQ ID NO: 14).

4. The isolated ALK2 antibody, or antigen binding fragment thereof, of claim 1, wherein the light chain CDR1 comprises the amino acid sequence SGDNIGTKYAY (SEQ ID NO: 19); the light chain CDR2 comprises the amino acid sequence LVIYGDSDRPS (SEQ ID NO: 26); the light chain CDR3 comprises the amino acid sequence YSADAQQMKA (SEQ ID NO: 6); the heavy chain CDR1 comprises the amino acid sequence GFTFNSSAMS (SEQ ID NO: 33); the heavy chain CDR2 comprises the amino acid sequence WVGRIKSKRDGYTTDYAAPVKG (SEQ ID NO: 38); and the heavy chain CDR3 comprises the amino acid sequence DYGGLKFDY (SEQ ID NO: 15).

5. The isolated ALK2 antibody, or antigen binding fragment thereof, of claim 1, wherein the light chain CDR1 comprises the amino acid sequence SGDNLRKYSAH (SEQ ID NO: 20); the light chain CDR2 comprises the amino acid sequence LVIYYDNKRPS (SEQ ID NO: 27); the light chain CDR3 comprises the amino acid sequence QVYASVHRM (SEQ ID NO: 7); the heavy chain CDR1 comprises the amino acid sequence GGTFSSYAIH (SEQ ID NO: 34); the heavy chain CDR2 comprises the amino acid sequence WMGRIIPDFGTANYAQKFQG (SEQ ID NO: 39); and the heavy chain CDR3 comprises the amino acid sequence GPTQAIHYFAY (SEQ ID NO: 16).

6. The isolated ALK2 antibody, or antigen binding fragment thereof, of claim 1, wherein the light chain CDR1 comprises the amino acid sequence SGDSLGSKSVH (SEQ ID NO: 21); the light chain CDR2 comprises the amino acid sequence LVIYRDSKRPS (SEQ ID NO: 28); the light chain CDR3 comprises the amino acid sequence QTYDWSHFGW (SEQ ID NO: 8); and the heavy chain CDR1 comprises the amino acid sequence GFTFSSAAMH (SEQ ID NO: 35); the heavy chain CDR2 comprises the amino acid sequence WVSVISSDGGSTYYADSVKG (SEQ ID NO: 12); and the heavy chain CDR3 comprises the amino acid sequence AGFILGSLGVAWMDV (SEQ ID NO: 17).

7. The isolated ALK2 antibody of claim 1, wherein the antibody, apart from the light chain CDR1, CDR2, and CDR3 and the heavy chain CDR1, CDR2, and CDR3, has at least 90% sequence identity to amino acids 1 to 331 of the sequence of SEQ ID NO:67, amino acids 1 to 332 of the sequence of SEQ ID NO:68, amino acids 1 to 333 of the sequence of SEQ ID NO:69, amino acids 1 to 332 of the sequence of SEQ ID NO:70, or amino acids 1 to 337 of the sequence of SEQ ID NO:71.

8. The isolated ALK2 antibody of claim 1, wherein the antibody comprises amino acids 1 to 433 of the sequence of SEQ ID NO:67, amino acids 1 to 434 of the sequence of SEQ ID NO:68, amino acids 1 to 435 of the sequence of SEQ ID NO:69, amino acids 1 to 434 of the sequence of SEQ ID NO: 70, or amino acids 1 to 439 of the sequence of SEQ ID NO:71.

9. A nucleic acid molecule comprising a nucleotide sequence encoding the ALK2 antibody or antigen binding fragment thereof of claim 1.

10. An expression vector comprising the nucleic acid molecule of claim 9.

11. A cell comprising the expression vector of claim 10.

12. A pharmaceutical composition comprising the ALK2 antibody or antigen binding fragment thereof of claim 1 and one or more pharmaceutically acceptable carriers or excipients.

13. The isolated ALK2 antibody of claim 1, wherein the antibody comprises amino acids 1 to 112 and amino acids 216 to 331 of the sequence of SEQ ID NO:67, amino acids 1 to 110 and amino acids 214 to 332 of the sequence of SEQ ID NO:68, amino acids 1 to 110 and amino acids 214 to 333 of the sequence of SEQ ID NO: 69, amino acids 1 to 109 and amino acids 213 to 332 of the sequence of SEQ ID NO:70, or amino acids 1 to 110 and amino acids 214 to 337 of the sequence of SEQ ID NO:71.

\* \* \* \* \*

```
                              SEQUENCE LISTING

<160> NUMBER OF SEQ ID NOS: 76

<210> SEQ ID NO 1
<211> LENGTH: 13
<212> TYPE: PRT
<213> ORGANISM: Artificial Sequence
<220> FEATURE:
<223> OTHER INFORMATION: Synthetic Construct

<400> SEQUENCE: 1

Ser Gly Ser Ser Ser Asn Ile Gly Ser Asn Tyr Val Ser
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Ser or Asn
<220> FEATURE:
<221> NAME/KEY: MISC_FEATURE
<222> LOCATION: (5)..(5)
<223> OTHER INFORMATION: Xaa is Ile or Leu
<220> FEATURE:
<221> NAME/KEY: MISC_FEATURE
<222> LOCATION: (6)..(6)
<223> OTHER INFORMATION: Xaa is Pro, Gly, or Arg
<220> FEATURE:
<221> NAME/KEY: MISC_FEATURE
<222> LOCATION: (7)..(7)
<223> OTHER INFORMATION: Xaa is Ser, Thr, or Lys
<220> FEATURE:
<221> NAME/KEY: MISC_FEATURE
<222> LOCATION: (8)..(8)
<223> OTHER INFORMATION: Xaa is Phe, Lys, or Tyr
<220> FEATURE:
<221> NAME/KEY: MISC_FEATURE
<222> LOCATION: (9)..(9)
<223> OTHER INFORMATION: Xaa is Phe, Tyr, or Ser
<220> FEATURE:
<221> NAME/KEY: MISC_FEATURE
<222> LOCATION: (10)..(10)
<223> OTHER INFORMATION: Xaa is Ala or Val
<220> FEATURE:
<221> NAME/KEY: MISC_FEATURE
<222> LOCATION: (11)..(11)
<223> OTHER INFORMATION: Xaa is Ser, Tyr, or His

<400> SEQUENCE: 2

Ser Gly Asp Xaa Xaa Xaa Xaa Xaa Xaa Xaa Xaa
1               5                   10
```

```
<210> SEQ ID NO 3
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is Val or Leu
<220> FEATURE:
<221> NAME/KEY: MISC_FEATURE
<222> LOCATION: (5)..(5)
<223> OTHER INFORMATION: Xaa is Lys, Arg, Gly, or Tyr
<220> FEATURE:
<221> NAME/KEY: MISC_FEATURE
<222> LOCATION: (6)..(6)
<223> OTHER INFORMATION: Xaa is Asn or Asp
<220> FEATURE:
<221> NAME/KEY: MISC_FEATURE
<222> LOCATION: (7)..(7)
<223> OTHER INFORMATION: Xaa is Asn or Ser
<220> FEATURE:
<221> NAME/KEY: MISC_FEATURE
<222> LOCATION: (8)..(8)
<223> OTHER INFORMATION: Xaa is His, Asn, Asp, or Lys

<400> SEQUENCE: 3

Xaa Xaa Ile Tyr Xaa Xaa Xaa Xaa Arg Pro Ser
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct

<400> SEQUENCE: 4

Ala Ser Trp Asp His Ser Asp Arg Phe Tyr Val
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct

<400> SEQUENCE: 5

Tyr Val Thr Ala Pro Trp Lys Ser Ile Trp
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

<400> SEQUENCE: 6

Tyr Ser Ala Asp Ala Gln Gln Met Lys Ala
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct
```

<400> SEQUENCE: 7

Gln Val Tyr Ala Ser Val His Arg Met
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct

<400> SEQUENCE: 8

Gln Thr Tyr Asp Trp Ser His Phe Gly Trp
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Gly or Phe
<220> FEATURE:
<221> NAME/KEY: MISC_FEATURE
<222> LOCATION: (5)..(5)
<223> OTHER INFORMATION: Xaa is Ser or Asn
<220> FEATURE:
<221> NAME/KEY: MISC_FEATURE
<222> LOCATION: (7)..(7)
<223> OTHER INFORMATION: Xaa is Tyr, His, Ser, or Ala
<220> FEATURE:
<221> NAME/KEY: MISC_FEATURE
<222> LOCATION: (8)..(8)
<223> OTHER INFORMATION: Xaa is Gly or Ala
<220> FEATURE:
<221> NAME/KEY: MISC_FEATURE
<222> LOCATION: (9)..(9)
<223> OTHER INFORMATION: Xaa is Val, Met, or Ile
<220> FEATURE:
<221> NAME/KEY: MISC_FEATURE
<222> LOCATION: (10)..(10)
<223> OTHER INFORMATION: Xaa is Ser or His

<400> SEQUENCE: 9

Gly Xaa Thr Phe Xaa Ser Xaa Xaa Xaa Xaa
1               5                   10

<210> SEQ ID NO 10
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Gly or Arg
<220> FEATURE:
<221> NAME/KEY: MISC_FEATURE
<222> LOCATION: (8)..(8)
<223> OTHER INFORMATION: Xaa is His or Asp
<220> FEATURE:
<221> NAME/KEY: MISC_FEATURE
<222> LOCATION: (11)..(11)
<223> OTHER INFORMATION: Xaa is Ile or Thr

<400> SEQUENCE: 10

Trp Met Gly Xaa Ile Ile Pro Xaa Phe Gly Xaa Ala Asn Tyr Ala Gln

Lys Phe Gln Gly
            20

<210> SEQ ID NO 11
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (9)..(9)
<223> OTHER INFORMATION: Xaa is Ala or Arg
<220> FEATURE:
<221> NAME/KEY: MISC_FEATURE
<222> LOCATION: (11)..(11)
<223> OTHER INFORMATION: Xaa is Ser or Gly
<220> FEATURE:
<221> NAME/KEY: MISC_FEATURE
<222> LOCATION: (12)..(12)
<223> OTHER INFORMATION: Xaa is Gly or Tyr

<400> SEQUENCE: 11

Trp Val Gly Arg Ile Lys Ser Lys Xaa Asp Xaa Xaa Thr Thr Asp Tyr
1               5                   10                  15

Ala Ala Pro Val Lys Gly
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic Construct

<400> SEQUENCE: 12

Trp Val Ser Val Ile Ser Ser Asp Gly Gly Ser Thr Tyr Tyr Ala Asp
1               5                   10                  15

Ser Val Lys Gly
            20

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct

<400> SEQUENCE: 13

Glu Ile Gly Ser Leu Asp Ile
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Construct

<400> SEQUENCE: 14

Asp Tyr Gly Val Ala Phe Ala Tyr
1               5

<210> SEQ ID NO 15
<211> LENGTH: 9
<212> TYPE: PRT

```
<213> ORGANISM: Artificial Sequence
<220> FEATURE:
<223> OTHER INFORMATION: Synthetic Construct

<400> SEQUENCE: 15

Asp Tyr Gly Gly Leu Lys Phe Asp Tyr
1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic Construct

<400> SEQUENCE: 16

Gly Pro Thr Gln Ala Ile His Tyr Phe Ala Tyr
1               5                   10

<210> SEQ ID NO 17
<211> LENGTH: 15
<212> TYPE: PRT
<213> ORGANISM: Artificial Sequence
<220> FEATURE:
<223> OTHER INFORMATION: Synthetic Construct

<400> SEQUENCE: 17

Ala Gly Phe Ile Leu Gly Ser Leu Gly Val Ala Trp Met Asp Val
1               5                   10                  15

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct

<400> SEQUENCE: 18

Ser Gly Asp Ser Ile Pro Ser Phe Phe Ala Ser
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic Construct

<400> SEQUENCE: 19

Ser Gly Asp Asn Ile Gly Thr Lys Tyr Ala Tyr
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

Ser Gly Asp Asn Leu Arg Lys Tyr Ser Ala His
1               5                   10

<210> SEQ ID NO 21
<211> LENGTH: 11
<212> TYPE: PRT
<213> ORGANISM: Artificial Sequence
```

```
<220> FEATURE:
<223> OTHER INFORMATION: Synthetic Construct

<400> SEQUENCE: 21

Ser Gly Asp Ser Leu Gly Ser Lys Ser Val His
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Arg, Gly, or Tyr
<220> FEATURE:
<221> NAME/KEY: MISC_FEATURE
<222> LOCATION: (7)..(7)
<223> OTHER INFORMATION: Xaa is Ser or Asn
<220> FEATURE:
<221> NAME/KEY: MISC_FEATURE
<222> LOCATION: (8)..(8)
<223> OTHER INFORMATION: Xaa is Asn, Asp, or Lys

<400> SEQUENCE: 22

Leu Val Ile Tyr Xaa Asp Xaa Xaa Arg Pro Ser
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Asn or Lys

<400> SEQUENCE: 23

Leu Val Ile Tyr Arg Asp Ser Xaa Arg Pro Ser
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic Construct

<400> SEQUENCE: 24

Val Leu Ile Tyr Lys Asn Asn His Arg Pro Ser
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthetic Construct

<400> SEQUENCE: 25

Leu Val Ile Tyr Arg Asp Ser Asn Arg Pro Ser
1               5                   10

<210> SEQ ID NO 26
<211> LENGTH: 11
```

```
<212> TYPE: PRT
<213> ORGANISM: Artificial Sequence
<220> FEATURE:
<223> OTHER INFORMATION: Synthetic Construct

<400> SEQUENCE: 26

Leu Val Ile Tyr Gly Asp Ser Asp Arg Pro Ser
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic Construct

<400> SEQUENCE: 27

Leu Val Ile Tyr Tyr Asp Asn Lys Arg Pro Ser
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

Leu Val Ile Tyr Arg Asp Ser Lys Arg Pro Ser
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is His or Ala
<220> FEATURE:
<221> NAME/KEY: MISC_FEATURE
<222> LOCATION: (10)..(10)
<223> OTHER INFORMATION: Xaa is Ser or His

<400> SEQUENCE: 29

Gly Phe Thr Phe Ser Ser Xaa Ala Met Xaa
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Ser or Asn
<220> FEATURE:
<221> NAME/KEY: MISC_FEATURE
<222> LOCATION: (7)..(7)
<223> OTHER INFORMATION: Xaa His or Ser

<400> SEQUENCE: 30

Gly Phe Thr Phe Xaa Ser Xaa Ala Met Ser
1               5                   10
```

```
<210> SEQ ID NO 31
<211> LENGTH: 10
<212> TYPE: PRT
<213> ORGANISM: Artificial Sequence
<220> FEATURE:
<223> OTHER INFORMATION: Synthetic Construct

<400> SEQUENCE: 31

Gly Gly Thr Phe Ser Ser Tyr Gly Val Ser
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Gly Phe Thr Phe Ser Ser His Ala Met Ser
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct

<400> SEQUENCE: 33

Gly Phe Thr Phe Asn Ser Ser Ala Met Ser
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic Construct

<400> SEQUENCE: 34

Gly Gly Thr Phe Ser Ser Tyr Ala Ile His
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic Construct

<400> SEQUENCE: 35

Gly Phe Thr Phe Ser Ser Ala Ala Met His
1               5                   10

<210> SEQ ID NO 36
<211> LENGTH: 20
<212> TYPE: PRT
<213> ORGANISM: Artificial Sequence
<220> FEATURE:
<223> OTHER INFORMATION: Synthetic Construct

<400> SEQUENCE: 36

Trp Met Gly Gly Ile Ile Pro His Phe Gly Ile Ala Asn Tyr Ala Gln
1               5                   10                  15

Lys Phe Gln Gly
            20
```

```
<210> SEQ ID NO 37
<211> LENGTH: 22
<212> TYPE: PRT
<213> ORGANISM: Artificial Sequence
<220> FEATURE:
<223> OTHER INFORMATION: Synthetic Construct

<400> SEQUENCE: 37

Trp Val Gly Arg Ile Lys Ser Lys Ala Asp Ser Gly Thr Thr Asp Tyr
1               5                   10                  15

Ala Ala Pro Val Lys Gly
            20

<210> SEQ ID NO 38
<211> LENGTH: 22
<212> TYPE: PRT
<213> ORGANISM: Artificial Sequence
<220> FEATURE:
<223> OTHER INFORMATION: Synthetic Construct

<400> SEQUENCE: 38

Trp Val Gly Arg Ile Lys Ser Lys Arg Asp Gly Tyr Thr Thr Asp Tyr
1               5                   10                  15

Ala Ala Pro Val Lys Gly
            20

<210> SEQ ID NO 39
<211> LENGTH: 20
<212> TYPE: PRT
<213> ORGANISM: Artificial Sequence
<220> FEATURE:
<223> OTHER INFORMATION: Synthetic Construct

<400> SEQUENCE: 39

Trp Met Gly Arg Ile Ile Pro Asp Phe Gly Thr Ala Asn Tyr Ala Gln
1               5                   10                  15

Lys Phe Gln Gly
            20

<210> SEQ ID NO 40
<211> LENGTH: 12
<212> TYPE: PRT
<213> ORGANISM: Artificial Sequence
<220> FEATURE:
<223> OTHER INFORMATION: Synthetic Construct

<400> SEQUENCE: 40

Arg Ala Ser Gln Gly Ile Ser Gly Asn Trp Leu Thr
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic Construct

<400> SEQUENCE: 41

Leu Leu Ile Tyr Asp Ala Ser Asn Leu Gln Ser
1               5                   10

<210> SEQ ID NO 42
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 42

His Gln Ser Tyr Arg Gly Pro Met
1               5

<210> SEQ ID NO 43
<211> LENGTH: 10
<212> TYPE: PRT
<213> ORGANISM: Artificial Sequence
<220> FEATURE:
<223> OTHER INFORMATION: Synthetic Construct

<400> SEQUENCE: 43

Gly Phe Thr Phe Gly Arg Phe Val Met His
1               5                   10

<210> SEQ ID NO 44
<211> LENGTH: 20
<212> TYPE: PRT
<213> ORGANISM: Artificial Sequence
<220> FEATURE:
<223> OTHER INFORMATION: Synthetic Construct

<400> SEQUENCE: 44

Trp Val Ser Val Ile Gly Tyr Ser Gly Ser Thr Tyr Tyr Ala Asp
1               5                   10                  15

Ser Val Lys Gly
            20

<210> SEQ ID NO 45
<211> LENGTH: 20
<212> TYPE: PRT
<213> ORGANISM: Artificial Sequence
<220> FEATURE:
<223> OTHER INFORMATION: Synthetic Construct

<400> SEQUENCE: 45

Glu Pro Gly Tyr Tyr Tyr Pro Ser Gly Tyr Tyr Arg Gly Pro Gly Tyr
1               5                   10                  15

Trp Met Asp Val
            20

<210> SEQ ID NO 46
<211> LENGTH: 11
<212> TYPE: PRT
<213> ORGANISM: Artificial Sequence
<220> FEATURE:
<223> OTHER INFORMATION: Synthetic Construct

<400> SEQUENCE: 46

Ser Gly Asp Asn Ile Arg Lys Lys Tyr Val His
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Synthetic Construct

<400> SEQUENCE: 47

Leu Val Ile Tyr Arg Asp Ser Asn Arg Pro Ser
1               5                   10
```

<210> SEQ ID NO 48
<211> LENGTH: 8
<212> TYPE: PRT
<213> ORGANISM: Artificial Sequence
<220> FEATURE:
<223> OTHER INFORMATION: Synthetic Construct

<400> SEQUENCE: 48

Ser Ser Ala Gly Arg Asp Asn Tyr
1               5

<210> SEQ ID NO 49
<211> LENGTH: 10
<212> TYPE: PRT
<213> ORGANISM: Artificial Sequence
<220> FEATURE:
<223> OTHER INFORMATION: Synthetic Construct

<400> SEQUENCE: 49

Gly Phe Thr Phe Ser Ser Ser Ala Met His
1               5                   10

<210> SEQ ID NO 50
<211> LENGTH: 20
<212> TYPE: PRT
<213> ORGANISM: Artificial Sequence
<220> FEATURE:
<223> OTHER INFORMATION: Synthetic Construct

<400> SEQUENCE: 50

Trp Val Ser Val Ile His Tyr Asp Ser Ser Glu Thr Tyr Tyr Ala Asp
1               5                   10                  15

Ser Val Lys Gly
            20

<210> SEQ ID NO 51
<211> LENGTH: 7
<212> TYPE: PRT
<213> ORGANISM: Artificial Sequence
<220> FEATURE:
<223> OTHER INFORMATION: Synthetic Construct

<400> SEQUENCE: 51

Asp Arg Tyr Phe Phe Asp Val
1               5

<210> SEQ ID NO 52
<211> LENGTH: 11
<212> TYPE: PRT
<213> ORGANISM: Artificial Sequence
<220> FEATURE:
<223> OTHER INFORMATION: Synthetic Construct

<400> SEQUENCE: 52

Ser Gly Asp Ala Leu Arg Tyr Tyr Ile Ala His
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic Construct

<400> SEQUENCE: 53

```
Leu Val Ile Tyr Tyr Asn Asn Asn Arg Pro Ser
1               5                   10

<210> SEQ ID NO 54
<211> LENGTH: 8
<212> TYPE: PRT
<213> ORGANISM: Artificial Sequence
<220> FEATURE:
<223> OTHER INFORMATION: Synthetic Construct

<400> SEQUENCE: 54

Gln Ser Tyr Gly Pro Gly Ser Val
1               5

<210> SEQ ID NO 55
<211> LENGTH: 10
<212> TYPE: PRT
<213> ORGANISM: Artificial Sequence
<220> FEATURE:
<223> OTHER INFORMATION: Synthetic Construct

<400> SEQUENCE: 55

Gly Phe Thr Phe Ser Asp Tyr Ala Met His
1               5                   10

<210> SEQ ID NO 56
<211> LENGTH: 20
<212> TYPE: PRT
<213> ORGANISM: Artificial Sequence
<220> FEATURE:
<223> OTHER INFORMATION: Synthetic Construct

<400> SEQUENCE: 56

Trp Val Ser Ser Ile Phe Tyr Ser Gly Ser Asn Thr Tyr Tyr Ala Asp
1               5                   10                  15

Ser Val Lys Gly
            20

<210> SEQ ID NO 57
<211> LENGTH: 11
<212> TYPE: PRT
<213> ORGANISM: Artificial Sequence
<220> FEATURE:
<223> OTHER INFORMATION: Synthetic Construct

<400> SEQUENCE: 57

Pro Lys Ser Tyr Ala Ser Gly Pro Phe Ala Tyr
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Synthetic Construct

<400> SEQUENCE: 58

Ser Gly Ser Ser Ser Asn Ile Gly Gln Asn Tyr Val Ser
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Synthetic Construct
```

```
<400> SEQUENCE: 59

Leu Leu Ile Tyr Asp Asn Ser Lys Arg Pro Ser
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic Construct

<400> SEQUENCE: 60

Ser Ser Trp Asp Leu Leu Ser Lys Ser Arg
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic Construct

<400> SEQUENCE: 61

Gly Gly Thr Phe Ser Thr His Ala Ile Ser
1               5                   10

<210> SEQ ID NO 62
<211> LENGTH: 20
<212> TYPE: PRT
<213> ORGANISM: Artificial Sequence
<220> FEATURE:
<223> OTHER INFORMATION: Synthetic Construct

<400> SEQUENCE: 62

Trp Met Gly Leu Ile Gln Pro Arg Phe Gly Thr Ala Asn Tyr Ala Gln
1               5                   10                  15

Lys Phe Gln Arg
            20

<210> SEQ ID NO 63
<211> LENGTH: 8
<212> TYPE: PRT
<213> ORGANISM: Artificial Sequence
<220> FEATURE:
<223> OTHER INFORMATION: Synthetic Construct

<400> SEQUENCE: 63

Asp Tyr Tyr Gly Gly Met Ala Tyr
1               5

<210> SEQ ID NO 64
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Asn or Ala
<220> FEATURE:
<221> NAME/KEY: MISC_FEATURE
<222> LOCATION: (5)..(5)
<223> OTHER INFORMATION: Xaa is Ile or Leu
<220> FEATURE:
<221> NAME/KEY: MISC_FEATURE
<222> LOCATION: (7)..(8)
<223> OTHER INFORMATION: Xaa is Lys or Tyr
```

```
<220> FEATURE:
<221> NAME/KEY: MISC_FEATURE
<222> LOCATION: (9)..(9)
<223> OTHER INFORMATION: Xaa is Tyr or Ile
<220> FEATURE:
<221> NAME/KEY: MISC_FEATURE
<222> LOCATION: (10)..(10)
<223> OTHER INFORMATION: Xaa is Val or Ala

<400> SEQUENCE: 64

Ser Gly Asp Xaa Xaa Arg Xaa Xaa Xaa Xaa His
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Val or Leu
<220> FEATURE:
<221> NAME/KEY: MISC_FEATURE
<222> LOCATION: (5)..(5)
<223> OTHER INFORMATION: Xaa is Asp, Arg, or Tyr
<220> FEATURE:
<221> NAME/KEY: MISC_FEATURE
<222> LOCATION: (6)..(6)
<223> OTHER INFORMATION: Xaa is Ala, Asp, or Asn
<220> FEATURE:
<221> NAME/KEY: MISC_FEATURE
<222> LOCATION: (7)..(7)
<223> OTHER INFORMATION: Xaa is Ser or Asn
<220> FEATURE:
<221> NAME/KEY: MISC_FEATURE
<222> LOCATION: (8)..(8)
<223> OTHER INFORMATION: Xaa is Lys or Asn
<220> FEATURE:
<221> NAME/KEY: MISC_FEATURE
<222> LOCATION: (9)..(9)
<223> OTHER INFORMATION: Xaa is Leu or Arg
<220> FEATURE:
<221> NAME/KEY: MISC_FEATURE
<222> LOCATION: (10)..(10)
<223> OTHER INFORMATION: Xaa is Gln or Pro

<400> SEQUENCE: 65

Leu Xaa Ile Tyr Xaa Xaa Xaa Xaa Xaa Xaa Ser
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Phe or Gly
<220> FEATURE:
<221> NAME/KEY: MISC_FEATURE
<222> LOCATION: (5)..(5)
<223> OTHER INFORMATION: Xaa is Gly or Ser
<220> FEATURE:
<221> NAME/KEY: MISC_FEATURE
<222> LOCATION: (6)..(6)
<223> OTHER INFORMATION: Xaa is Arg, Ser, Asp, or Thr
<220> FEATURE:
<221> NAME/KEY: MISC_FEATURE
<222> LOCATION: (7)..(7)
<223> OTHER INFORMATION: Xaa is Phe, Ser, Tyr, or His
<220> FEATURE:
```

```
<221> NAME/KEY: MISC_FEATURE
<222> LOCATION: (8)..(8)
<223> OTHER INFORMATION: Xaa is Val or Ala
<220> FEATURE:
<221> NAME/KEY: MISC_FEATURE
<222> LOCATION: (9)..(9)
<223> OTHER INFORMATION: Xaa is Met or Ile
<220> FEATURE:
<221> NAME/KEY: MISC_FEATURE
<222> LOCATION: (10)..(10)
<223> OTHER INFORMATION: Xaa is His or Ser

<400> SEQUENCE: 66

Gly Xaa Thr Phe Xaa Xaa Xaa Xaa Xaa Xaa
1               5                   10

<210> SEQ ID NO 67
<211> LENGTH: 452
<212> TYPE: PRT
<213> ORGANISM: Artificial Sequence
<220> FEATURE:
<223> OTHER INFORMATION: Synthetic Construct

<400> SEQUENCE: 67

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Val Leu
        35                  40                  45

Ile Tyr Lys Asn Asn His Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ala Ser Trp Asp His Ser Asp
                85                  90                  95

Arg Phe Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Ala Gln Val Gln Leu Val Gln Ser Gly Ala
    210                 215                 220

Glu Val Lys Lys Pro Gly Ser Ser Val Lys Val Ser Cys Lys Ala Ser
225                 230                 235                 240

Gly Gly Thr Phe Ser Ser Tyr Gly Val Ser Trp Val Arg Gln Ala Pro
                245                 250                 255

Gly Gln Gly Leu Glu Trp Met Gly Gly Ile Ile Pro His Phe Gly Ile
            260                 265                 270

Ala Asn Tyr Ala Gln Lys Phe Gln Gly Arg Val Thr Ile Thr Ala Asp
```

275                 280                 285
Glu Ser Thr Ser Thr Ala Tyr Met Glu Leu Ser Ser Leu Arg Ser Glu
    290                 295                 300

Asp Thr Ala Val Tyr Tyr Cys Ala Arg Glu Ile Gly Ser Leu Asp Ile
305                 310                 315                 320

Trp Gly Gln Gly Thr Leu Val Thr Val Ser Ala Ser Thr Lys Gly
                    325                 330                 335

Pro Ser Val Phe Pro Leu Ala Pro Ser Ser Lys Ser Thr Ser Gly Gly
                340                 345                 350

Thr Ala Ala Leu Gly Cys Leu Val Lys Asp Tyr Phe Pro Glu Pro Val
                355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Lys Val Glu Pro Lys
                420                 425                 430

Ser Glu Phe Asp Tyr Lys Asp Asp Asp Lys Gly Ala Pro His His
            435                 440                 445

His His His His
        450

<210> SEQ ID NO 68
<211> LENGTH: 453
<212> TYPE: PRT
<213> ORGANISM: Artificial Sequence
<220> FEATURE:
<223> OTHER INFORMATION: Synthetic Construct

<400> SEQUENCE: 68

Asp Ile Glu Leu Thr Gln Pro Pro Ser Val Ser Val Ser Pro Gly Gln
1               5                   10                  15

Thr Ala Ser Ile Thr Cys Ser Gly Asp Ser Ile Pro Ser Phe Phe Ala
                20                  25                  30

Ser Trp Tyr Gln Gln Lys Pro Gly Gln Ala Pro Val Leu Val Ile Tyr
            35                  40                  45

Arg Asp Ser Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Tyr Val Thr Ala Pro Trp Lys Ser Ile
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser

```
                180                 185                 190
Tyr Ser Cys Gln Val Thr His Glu Gly Ser Thr Val Glu Lys Thr Val
            195                 200                 205

Ala Pro Thr Glu Ala Glu Val Gln Leu Val Glu Ser Gly Gly Gly Leu
    210                 215                 220

Val Lys Pro Gly Gly Ser Leu Arg Leu Ser Cys Ala Ala Ser Gly Phe
225                 230                 235                 240

Thr Phe Ser Ser His Ala Met Ser Trp Val Arg Gln Ala Pro Gly Lys
                245                 250                 255

Gly Leu Glu Trp Val Gly Arg Ile Lys Ser Lys Ala Asp Ser Gly Thr
            260                 265                 270

Thr Asp Tyr Ala Ala Pro Val Lys Gly Arg Phe Thr Ile Ser Arg Asp
        275                 280                 285

Asp Ser Lys Asn Thr Leu Tyr Leu Gln Met Asn Ser Leu Lys Thr Glu
    290                 295                 300

Asp Thr Ala Val Tyr Tyr Cys Ala Arg Asp Tyr Gly Val Ala Phe Ala
305                 310                 315                 320

Tyr Trp Gly Gln Gly Thr Leu Val Thr Val Ser Ser Ala Ser Thr Lys
                325                 330                 335

Gly Pro Ser Val Phe Pro Leu Ala Pro Ser Ser Lys Ser Thr Ser Gly
            340                 345                 350

Gly Thr Ala Ala Leu Gly Cys Leu Val Lys Asp Tyr Phe Pro Glu Pro
        355                 360                 365

Val Thr Val Ser Trp Asn Ser Gly Ala Leu Thr Ser Gly Val His Thr
    370                 375                 380

Phe Pro Ala Val Leu Gln Ser Ser Gly Leu Tyr Ser Leu Ser Ser Val
385                 390                 395                 400

Val Thr Val Pro Ser Ser Leu Gly Thr Gln Thr Tyr Ile Cys Asn
                405                 410                 415

Val Asn His Lys Pro Ser Asn Thr Lys Val Asp Lys Lys Val Glu Pro
            420                 425                 430

Lys Ser Glu Phe Asp Tyr Lys Asp Asp Asp Lys Gly Ala Pro His
        435                 440                 445

His His His His
    450

<210> SEQ ID NO 69
<211> LENGTH: 454
<212> TYPE: PRT
<213> ORGANISM: Artificial Sequence
<220> FEATURE:
<223> OTHER INFORMATION: Synthetic Construct

<400> SEQUENCE: 69

Asp Ile Glu Leu Thr Gln Pro Pro Ser Val Ser Val Ser Pro Gly Gln
1               5                   10                  15

Thr Ala Ser Ile Thr Cys Ser Gly Asp Asn Ile Gly Thr Lys Tyr Ala
            20                  25                  30

Tyr Trp Tyr Gln Gln Lys Pro Gly Gln Ala Pro Val Leu Val Ile Tyr
        35                  40                  45

Gly Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Tyr Ser Ala Asp Ala Gln Gln Met Lys
```

```
            85                  90                  95
Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                    165                 170                 175

Ser Ser Tyr Leu Ser Leu Thr Pro Glu Gln Trp Lys Ser His Arg Ser
                    180                 185                 190

Tyr Ser Cys Gln Val Thr His Glu Gly Ser Thr Val Glu Lys Thr Val
            195                 200                 205

Ala Pro Thr Glu Ala Glu Val Gln Leu Val Glu Ser Gly Gly Gly Leu
            210                 215                 220

Val Lys Pro Gly Gly Ser Leu Arg Leu Ser Cys Ala Ala Ser Gly Phe
225                 230                 235                 240

Thr Phe Asn Ser Ser Ala Met Ser Trp Val Arg Gln Ala Pro Gly Lys
                    245                 250                 255

Gly Leu Glu Trp Val Gly Arg Ile Lys Ser Lys Arg Asp Gly Tyr Thr
                    260                 265                 270

Thr Asp Tyr Ala Ala Pro Val Lys Gly Arg Phe Thr Ile Ser Arg Asp
            275                 280                 285

Asp Ser Lys Asn Thr Leu Tyr Leu Gln Met Asn Ser Leu Lys Thr Glu
            290                 295                 300

Asp Thr Ala Val Tyr Tyr Cys Ala Arg Asp Tyr Gly Gly Leu Lys Phe
305                 310                 315                 320

Asp Tyr Trp Gly Gln Gly Thr Leu Val Thr Val Ser Ser Ala Ser Thr
                    325                 330                 335

Lys Gly Pro Ser Val Phe Pro Leu Ala Pro Ser Ser Lys Ser Thr Ser
                    340                 345                 350

Gly Gly Thr Ala Ala Leu Gly Cys Leu Val Lys Asp Tyr Phe Pro Glu
            355                 360                 365

Pro Val Thr Val Ser Trp Asn Ser Gly Ala Leu Thr Ser Gly Val His
            370                 375                 380

Thr Phe Pro Ala Val Leu Gln Ser Ser Gly Leu Tyr Ser Leu Ser Ser
385                 390                 395                 400

Val Val Thr Val Pro Ser Ser Ser Leu Gly Thr Gln Thr Tyr Ile Cys
                    405                 410                 415

Asn Val Asn His Lys Pro Ser Asn Thr Lys Val Asp Lys Lys Val Glu
                    420                 425                 430

Pro Lys Ser Glu Phe Asp Tyr Lys Asp Asp Asp Lys Gly Ala Pro
            435                 440                 445

His His His His His His
        450

<210> SEQ ID NO 70
<211> LENGTH: 453
<212> TYPE: PRT
<213> ORGANISM: Artificial Sequence
<220> FEATURE:
<223> OTHER INFORMATION: Synthetic Construct
```

```
<400> SEQUENCE: 70

Asp Ile Glu Leu Thr Gln Pro Pro Ser Val Ser Val Ser Pro Gly Gln
1               5                   10                  15

Thr Ala Ser Ile Thr Cys Ser Gly Asp Asn Leu Arg Lys Tyr Ser Ala
            20                  25                  30

His Trp Tyr Gln Gln Lys Pro Gly Gln Ala Pro Val Leu Val Ile Tyr
        35                  40                  45

Tyr Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Val Tyr Ala Ser Val His Arg Met
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Ala Gln Val Gln Leu Val Gln Ser Gly Ala Glu Val Lys
    210                 215                 220

Lys Pro Gly Ser Ser Val Lys Val Ser Cys Lys Ala Ser Gly Gly Thr
225                 230                 235                 240

Phe Ser Ser Tyr Ala Ile His Trp Val Arg Gln Ala Pro Gly Gln Gly
                245                 250                 255

Leu Glu Trp Met Gly Arg Ile Ile Pro Asp Phe Gly Thr Ala Asn Tyr
            260                 265                 270

Ala Gln Lys Phe Gln Gly Arg Val Thr Ile Thr Ala Asp Glu Ser Thr
        275                 280                 285

Ser Thr Ala Tyr Met Glu Leu Ser Ser Leu Arg Ser Glu Asp Thr Ala
    290                 295                 300

Val Tyr Tyr Cys Ala Arg Gly Pro Thr Gln Ala Ile His Tyr Phe Ala
305                 310                 315                 320

Tyr Trp Gly Gln Gly Thr Leu Val Thr Val Ser Ser Ala Ser Thr Lys
                325                 330                 335

Gly Pro Ser Val Phe Pro Leu Ala Pro Ser Ser Lys Ser Thr Ser Gly
            340                 345                 350

Gly Thr Ala Ala Leu Gly Cys Leu Val Lys Asp Tyr Phe Pro Glu Pro
        355                 360                 365

Val Thr Val Ser Trp Asn Ser Gly Ala Leu Thr Ser Gly Val His Thr
370                 375                 380

Phe Pro Ala Val Leu Gln Ser Ser Gly Leu Tyr Ser Leu Ser Ser Val
385                 390                 395                 400

Val Thr Val Pro Ser Ser Ser Leu Gly Thr Gln Thr Tyr Ile Cys Asn
                405                 410                 415
```

Val Asn His Lys Pro Ser Asn Thr Lys Val Asp Lys Val Glu Pro
                420                 425                 430

Lys Ser Glu Phe Asp Tyr Lys Asp Asp Asp Lys Gly Ala Pro His
        435                 440                 445

His His His His His
        450

<210> SEQ ID NO 71
<211> LENGTH: 458
<212> TYPE: PRT
<213> ORGANISM: Artificial Sequence
<220> FEATURE:
<223> OTHER INFORMATION: Synthetic Construct

<400> SEQUENCE: 71

Asp Ile Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Lys Ser Val
            20                  25                  30

His Trp Tyr Gln Gln Lys Pro Gly Gln Ala Pro Val Leu Val Ile Tyr
        35                  40                  45

Arg Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Asp Trp Ser His Phe Gly
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ala Glu Val Gln Leu Leu Glu Ser Gly Gly Gly Leu
    210                 215                 220

Val Gln Pro Gly Gly Ser Leu Arg Leu Ser Cys Ala Ala Ser Gly Phe
225                 230                 235                 240

Thr Phe Ser Ser Ala Ala Met His Trp Val Arg Gln Ala Pro Gly Lys
                245                 250                 255

Gly Leu Glu Trp Val Ser Val Ile Ser Ser Asp Gly Gly Ser Thr Tyr
            260                 265                 270

Tyr Ala Asp Ser Val Lys Gly Arg Phe Thr Ile Ser Arg Asp Asn Ser
        275                 280                 285

Lys Asn Thr Leu Tyr Leu Gln Met Asn Ser Leu Arg Ala Glu Asp Thr
    290                 295                 300

Ala Val Tyr Tyr Cys Ala Arg Ala Gly Phe Ile Leu Gly Ser Leu Gly
305                 310                 315                 320

```
Val Ala Trp Met Asp Val Trp Gly Gln Gly Thr Leu Val Thr Val Ser
            325                 330                 335

Ser Ala Ser Thr Lys Gly Pro Ser Val Phe Pro Leu Ala Pro Ser Ser
            340                 345                 350

Lys Ser Thr Ser Gly Gly Thr Ala Ala Leu Gly Cys Leu Val Lys Asp
            355                 360                 365

Tyr Phe Pro Glu Pro Val Thr Val Ser Trp Asn Ser Gly Ala Leu Thr
            370                 375                 380

Ser Gly Val His Thr Phe Pro Ala Val Leu Gln Ser Ser Gly Leu Tyr
385                 390                 395                 400

Ser Leu Ser Ser Val Val Thr Val Pro Ser Ser Ser Leu Gly Thr Gln
            405                 410                 415

Thr Tyr Ile Cys Asn Val Asn His Lys Pro Ser Asn Thr Lys Val Asp
            420                 425                 430

Lys Lys Val Glu Pro Lys Ser Glu Phe Asp Tyr Lys Asp Asp Asp Asp
            435                 440                 445

Lys Gly Ala Pro His His His His His His
            450                 455

<210> SEQ ID NO 72
<211> LENGTH: 465
<212> TYPE: PRT
<213> ORGANISM: Artificial Sequence
<220> FEATURE:
<223> OTHER INFORMATION: Synthetic Construct

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Gly Asn
            20                  25                  30

Trp Leu Thr Trp Tyr Gln Gln Lys Pro Gly Lys Ala Pro Lys Leu Leu
            35                  40                  45

Ile Tyr Asp Ala Ser Asn Leu Gln Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys His Gln Ser Tyr Arg Gly Pro
                85                  90                  95

Met Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Ala Glu Val Gln Leu Leu Glu Ser Gly Gly
            210                 215                 220
```

```
Gly Leu Val Gln Pro Gly Gly Ser Leu Arg Leu Ser Cys Ala Ala Ser
225                 230                 235                 240

Gly Phe Thr Phe Gly Arg Phe Val Met His Trp Val Arg Gln Ala Pro
            245                 250                 255

Gly Lys Gly Leu Glu Trp Val Ser Val Ile Gly Tyr Ser Gly Ser Ser
        260                 265                 270

Thr Tyr Tyr Ala Asp Ser Val Lys Gly Arg Phe Thr Ile Ser Arg Asp
    275                 280                 285

Asn Ser Lys Asn Thr Leu Tyr Leu Gln Met Asn Ser Leu Arg Ala Glu
290                 295                 300

Asp Thr Ala Val Tyr Tyr Cys Ala Arg Glu Pro Gly Tyr Tyr Tyr Pro
305                 310                 315                 320

Ser Gly Tyr Tyr Arg Gly Pro Gly Tyr Trp Met Asp Val Trp Gly Gln
                325                 330                 335

Gly Thr Leu Val Thr Val Ser Ser Ala Ser Thr Lys Gly Pro Ser Val
            340                 345                 350

Phe Pro Leu Ala Pro Ser Ser Lys Ser Thr Ser Gly Gly Thr Ala Ala
        355                 360                 365

Leu Gly Cys Leu Val Lys Asp Tyr Phe Pro Glu Pro Val Thr Val Ser
370                 375                 380

Trp Asn Ser Gly Ala Leu Thr Ser Gly Val His Thr Phe Pro Ala Val
385                 390                 395                 400

Leu Gln Ser Ser Gly Leu Tyr Ser Leu Ser Ser Val Val Thr Val Pro
                405                 410                 415

Ser Ser Ser Leu Gly Thr Gln Thr Tyr Ile Cys Asn Val Asn His Lys
            420                 425                 430

Pro Ser Asn Thr Lys Val Asp Lys Lys Val Glu Pro Lys Ser Glu Phe
        435                 440                 445

Asp Tyr Lys Asp Asp Asp Asp Lys Gly Ala Pro His His His His His
    450                 455                 460

His
465

<210> SEQ ID NO 73
<211> LENGTH: 448
<212> TYPE: PRT
<213> ORGANISM: Artificial Sequence
<220> FEATURE:
<223> OTHER INFORMATION: Synthetic Construct

<400> SEQUENCE: 73

Asp Ile Glu Leu Thr Gln Pro Pro Ser Val Ser Val Ser Pro Gly Gln
1               5                   10                  15

Thr Ala Ser Ile Thr Cys Ser Gly Asp Asn Ile Arg Lys Lys Tyr Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Ala Gly Arg Asp Asn Tyr Val
                85                  90                  95

Phe Gly Gly Gly Thr Lys Leu Thr Val Leu Gly Gln Pro Lys Ala Ala
            100                 105                 110
```

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
        130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Ala Glu Val Gln Leu Leu Glu Ser Gly Gly Gly Leu Val Gln
210                 215                 220

Pro Gly Gly Ser Leu Arg Leu Ser Cys Ala Ala Ser Gly Phe Thr Phe
225                 230                 235                 240

Ser Ser Ser Ala Met His Trp Val Arg Gln Ala Pro Gly Lys Gly Leu
                245                 250                 255

Glu Trp Val Ser Val Ile His Tyr Asp Ser Ser Glu Thr Tyr Tyr Ala
            260                 265                 270

Asp Ser Val Lys Gly Arg Phe Thr Ile Ser Arg Asp Asn Ser Lys Asn
        275                 280                 285

Thr Leu Tyr Leu Gln Met Asn Ser Leu Arg Ala Glu Asp Thr Ala Val
290                 295                 300

Tyr Tyr Cys Ala Arg Asp Arg Tyr Phe Phe Asp Val Trp Gly Gln Gly
305                 310                 315                 320

Thr Leu Val Thr Val Ser Ser Ala Ser Thr Lys Gly Pro Ser Val Phe
                325                 330                 335

Pro Leu Ala Pro Ser Ser Lys Ser Thr Ser Gly Gly Thr Ala Ala Leu
            340                 345                 350

Gly Cys Leu Val Lys Asp Tyr Phe Pro Glu Pro Val Thr Val Ser Trp
        355                 360                 365

Asn Ser Gly Ala Leu Thr Ser Gly Val His Thr Phe Pro Ala Val Leu
370                 375                 380

Gln Ser Ser Gly Leu Tyr Ser Leu Ser Ser Val Val Thr Val Pro Ser
385                 390                 395                 400

Ser Ser Leu Gly Thr Gln Thr Tyr Ile Cys Asn Val Asn His Lys Pro
                405                 410                 415

Ser Asn Thr Lys Val Asp Lys Lys Val Glu Pro Lys Ser Glu Phe Asp
            420                 425                 430

Tyr Lys Asp Asp Asp Lys Gly Ala Pro His His His His His His
        435                 440                 445

<210> SEQ ID NO 74
<211> LENGTH: 452
<212> TYPE: PRT
<213> ORGANISM: Artificial Sequence
<220> FEATURE:
<223> OTHER INFORMATION: Synthetic Construct

<400> SEQUENCE: 74

Asp Ile Glu Leu Thr Gln Pro Pro Ser Val Ser Val Ser Pro Gly Gln
1               5                   10                  15

Thr Ala Ser Ile Thr Cys Ser Gly Asp Ala Leu Arg Tyr Tyr Ile Ala
            20                  25                  30

```
His Trp Tyr Gln Gln Lys Pro Gly Gln Ala Pro Val Leu Val Ile Tyr
            35                  40                  45

Tyr Asn Asn Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Tyr Gly Pro Gly Ser Val Val
                 85                  90                  95

Phe Gly Gly Gly Thr Lys Leu Thr Val Leu Gly Gln Pro Lys Ala Ala
                100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
            130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
            195                 200                 205

Thr Glu Ala Glu Val Gln Leu Leu Glu Ser Gly Gly Gly Leu Val Gln
        210                 215                 220

Pro Gly Gly Ser Leu Arg Leu Ser Cys Ala Ala Ser Gly Phe Thr Phe
225                 230                 235                 240

Ser Asp Tyr Ala Met His Trp Val Arg Gln Ala Pro Gly Lys Gly Leu
                245                 250                 255

Glu Trp Val Ser Ser Ile Phe Tyr Ser Gly Ser Asn Thr Tyr Tyr Ala
            260                 265                 270

Asp Ser Val Lys Gly Arg Phe Thr Ile Ser Arg Asp Asn Ser Lys Asn
        275                 280                 285

Thr Leu Tyr Leu Gln Met Asn Ser Leu Arg Ala Glu Asp Thr Ala Val
        290                 295                 300

Tyr Tyr Cys Ala Arg Pro Lys Ser Tyr Ala Ser Gly Pro Phe Ala Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
            355                 360                 365

Thr Val Ser Trp Asn Ser Gly Ala Leu Thr Ser Gly Val His Thr Phe
        370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Lys Val Glu Pro Lys
            420                 425                 430

Ser Glu Phe Asp Tyr Lys Asp Asp Asp Lys Gly Ala Pro His His
            435                 440                 445
```

His His His His
    450

<210> SEQ ID NO 75
<211> LENGTH: 453
<212> TYPE: PRT
<213> ORGANISM: Artificial Sequence
<220> FEATURE:
<223> OTHER INFORMATION: Synthetic Construct

<400> SEQUENCE: 75

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Gln Asn
            20                  25                  30

Tyr Val Ser Trp Tyr Gln Gln Leu Pro Gly Thr Ala Pro Lys Leu Leu
        35                  40                  45

Ile Tyr Asp Asn Ser Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ser Trp Asp Leu Leu Ser
                85                  90                  95

Lys Ser Arg Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Ala Gln Val Gln Leu Val Gln Ser Gly Ala
    210                 215                 220

Glu Val Lys Lys Pro Gly Ser Ser Val Lys Val Ser Cys Lys Ala Ser
225                 230                 235                 240

Gly Gly Thr Phe Ser Thr His Ala Ile Ser Trp Val Arg Gln Ala Pro
                245                 250                 255

Gly Gln Gly Leu Glu Trp Met Gly Leu Ile Gln Pro Arg Phe Gly Thr
            260                 265                 270

Ala Asn Tyr Ala Gln Lys Phe Gln Gly Arg Val Thr Ile Thr Ala Asp
        275                 280                 285

Glu Ser Thr Ser Thr Ala Tyr Met Glu Leu Ser Ser Leu Arg Ser Glu
    290                 295                 300

Asp Thr Ala Val Tyr Tyr Cys Ala Arg Asp Tyr Tyr Gly Gly Met Ala
305                 310                 315                 320

Tyr Trp Gly Gln Gly Thr Leu Val Thr Val Ser Ser Ala Ser Thr Lys
                325                 330                 335

Gly Pro Ser Val Phe Pro Leu Ala Pro Ser Ser Lys Ser Thr Ser Gly
            340                 345                 350

```
Gly Thr Ala Ala Leu Gly Cys Leu Val Lys Asp Tyr Phe Pro Glu Pro
            355                 360                 365

Val Thr Val Ser Trp Asn Ser Gly Ala Leu Thr Ser Gly Val His Thr
    370                 375                 380

Phe Pro Ala Val Leu Gln Ser Ser Gly Leu Tyr Ser Leu Ser Ser Val
385                 390                 395                 400

Val Thr Val Pro Ser Ser Ser Leu Gly Thr Gln Thr Tyr Ile Cys Asn
                405                 410                 415

Val Asn His Lys Pro Ser Asn Thr Lys Val Asp Lys Lys Val Glu Pro
            420                 425                 430

Lys Ser Glu Phe Asp Tyr Lys Asp Asp Asp Lys Gly Ala Pro His
            435                 440                 445

His His His His His
        450

<210> SEQ ID NO 76
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Val or Ser
<220> FEATURE:
<221> NAME/KEY: MISC_FEATURE
<222> LOCATION: (6)..(6)
<223> OTHER INFORMATION: Xaa is Gly, His, or Phe
<220> FEATURE:
<221> NAME/KEY: MISC_FEATURE
<222> LOCATION: (8)..(8)
<223> OTHER INFORMATION: Xaa is Ser or Asp
<220> FEATURE:
<221> NAME/KEY: MISC_FEATURE
<222> LOCATION: (9)..(9)
<223> OTHER INFORMATION: Xaa is Gly or Ser
<220> FEATURE:
<221> NAME/KEY: MISC_FEATURE
<222> LOCATION: (11)..(11)
<223> OTHER INFORMATION: Xaa is Ser, Glu, or Asn

<400> SEQUENCE: 76

Trp Val Ser Xaa Ile Xaa Tyr Xaa Xaa Ser Xaa Thr Tyr Tyr Ala Asp
1               5                   10                  15

Ser Val Lys Gly
        20
```